US012773332B2

(12) United States Patent
Horzewski

(10) Patent No.: US 12,773,332 B2
(45) Date of Patent: Oct. 27, 2026

(54) INTRAVASCULAR DELIVERY SYSTEMS, DEVICES AND METHOD

(71) Applicant: VS3 Medical, Inc., San Jose, CA (US)

(72) Inventor: Michael J. Horzewski, San Jose, CA (US)

(73) Assignee: VS3 MEDICAL, INC., San Jose, CA (US)

( * ) Notice: Subject to any disclaimer, the term of this patent is extended or adjusted under 35 U.S.C. 154(b) by 0 days.

(21) Appl. No.: 19/253,524

(22) Filed: Jun. 27, 2025

(65) Prior Publication Data

US 2025/0318940 A1 Oct. 16, 2025

Related U.S. Application Data

(63) Continuation of application No. 18/680,773, filed on May 31, 2024, now Pat. No. 12,364,614.

(Continued)

(51) Int. Cl.

*A61F 2/962* (2013.01)
*A61F 2/95* (2013.01)
*A61F 2/966* (2013.01)

(52) U.S. Cl.

CPC ...... *A61F 2/962* (2013.01); *A61F 2002/9505* (2013.01); *A61F 2002/9528* (2013.01); *A61F 2002/9665* (2013.01)

(58) Field of Classification Search

CPC .......... A61F 2/962; A61F 2/964; A61F 2/965; A61F 2/966; A61F 2002/9505;

(Continued)

(56) References Cited

U.S. PATENT DOCUMENTS 5,681,322 A * 10/1997 Hartigan, Jr. .......... A61F 2/0095 604/93.01
8,715,315 B1 5/2014 Janardhan et al.

(Continued)

FOREIGN PATENT DOCUMENTS

AU 1085892 A * 8/1992 .......... A61B 18/1492
AU 2008345596 A1 * 7/2009 .......... G06Q 30/0261

(Continued)

OTHER PUBLICATIONS

International Search Report and Written Opinion for International App. No. PCT/US2021/020458, Mailed Jun. 25, 2021, 17 pages.

(Continued)

*Primary Examiner* — Christie Bahena

(74) *Attorney, Agent, or Firm* — Ashurst Perkins Coie US LLP

(57) ABSTRACT

Intravascular delivery systems, devices, and methods are disclosed herein. A representative delivery device can include an inner shaft defining a lumen extending along a length of the delivery device, an outer shaft surrounding the inner shaft along at least a portion of the length of the delivery device, and a tip portion distal to the outer shaft. The inner shaft can include a recess configured to receive a self-expandable implant. The outer shaft can be retractable relative to the inner shaft, and can include a functional member that provides increased tensile strength to the outer shaft, and a coil. The tip portion can extend to a distal terminus of the delivery device and include a cross-sectional dimension that tapers in a distal direction.

23 Claims, 31 Drawing Sheets

Related U.S. Application Data

(60) Provisional application No. 63/505,349, filed on May 31, 2023.

(58) Field of Classification Search
CPC ...... A61F 2002/9528; A61F 2002/9665; A61F 2230/0023; A61F 2230/0067; A61F 2230/0039; A61M 25/0012; A61M 25/005; A61M 25/0051; A61M 25/0053
See application file for complete search history.

(56) References Cited

U.S. PATENT DOCUMENTS

| | | | | |
|---|---|---|---|---|
| 2002/0099435 | A1* | 7/2002 | Stinson | A61F 2/97 623/1.12 |
| 2003/0097172 | A1 | 5/2003 | Shalev et al. | |
| 2004/0167635 | A1 | 8/2004 | Yachia et al. | |
| 2007/0059435 | A1 | 3/2007 | Santos et al. | |
| 2009/0105747 | A1 | 4/2009 | Chanduszko et al. | |
| 2009/0287293 | A1 | 11/2009 | Mailhot, Jr. | |
| 2011/0137402 | A1* | 6/2011 | Dorn | A61F 2/966 156/70 |
| 2012/0239133 | A1 | 9/2012 | Cartledge et al. | |
| 2012/0239142 | A1* | 9/2012 | Liu | A61F 2/2439 623/2.11 |
| 2012/0271232 | A1* | 10/2012 | Katsurada | A61M 25/008 604/524 |
| 2013/0268044 | A1 | 10/2013 | Parsons et al. | |
| 2013/0325141 | A1 | 12/2013 | Gill et al. | |
| 2014/0257460 | A1* | 9/2014 | Gibbons, Jr. | A61F 2/966 623/1.12 |
| 2014/0265030 | A1* | 9/2014 | Janardhan | A61B 17/12172 219/121.64 |
| 2016/0135941 | A1 | 5/2016 | Binmoeller et al. | |
| 2017/0128187 | A1 | 5/2017 | Ziapour | |
| 2017/0281381 | A1* | 10/2017 | Harris | A61F 2/966 |
| 2017/0340460 | A1 | 11/2017 | Rosen et al. | |
| 2018/0235745 | A1 | 8/2018 | Seybold et al. | |
| 2019/0099589 | A1 | 4/2019 | Walsh et al. | |
| 2019/0247209 | A1 | 8/2019 | Longo et al. | |
| 2020/0155332 | A1* | 5/2020 | Longo | A61F 2/958 |
| 2020/0268535 | A1 | 8/2020 | Carpenter et al. | |
| 2022/0125608 | A1 | 4/2022 | Ethridge et al. | |
| 2022/0378590 | A1 | 12/2022 | Knoepp | |
| 2023/0097980 | A1 | 3/2023 | Amans | |

FOREIGN PATENT DOCUMENTS

| | | | | | |
|---|---|---|---|---|---|
| AU | 2021229505 | A1 | | 10/2022 | |
| CN | 110573115 | A | | 12/2019 | |
| EP | 4114325 | A1 | | 1/2023 | |
| JP | 2016523118 | A | * | 8/2016 | A61B 10/0266 |
| JP | 2023516695 | A | | 4/2023 | |
| KR | 20130076868 | A | | 7/2013 | |
| WO | 2016003470 | A1 | | 1/2016 | |
| WO | 2018112118 | A1 | | 6/2018 | |
| WO | 2018163055 | A1 | | 9/2018 | |
| WO | 2021178401 | A1 | | 9/2021 | |

OTHER PUBLICATIONS

Canadian Office Action issued in corresponding application CA 3170546 dated Jan. 8, 2026 (4 pages).
Canadian Office Action issued in corresponding application CA 3170546 dated Nov. 8, 2023 (6 pages).
Examination Report No. 1 issued in corresponding application AU2021229505 dated Jan. 15, 2024 (3 pages).
Examination Report No. 1 issued in corresponding application AU2024216493 dated Feb. 4, 2026 (4 pages).
Japanese Office Action issued in corresponding application JP 2025-061781 dated Feb. 3, 2026 (4 pages).
Korean Office Action issued in corresponding application KR 10-2022-7034127 dated Nov. 11, 2025 (10 pages).
Office Action issued in corresponding application U.S. Appl. No. 17/908,623 dated Oct. 1, 2025 (15 pages).
Office Action issued in corresponding application U.S. Appl. No. 19/253,524 dated Nov. 3, 2025 (26 pages).
Office Action issued in corresponding application U.S. Appl. No. 19/296,724 dated Feb. 17, 2026 (15 pages).
CN: Chinese Office Action issued in corresponding application CN 202180019137X dated May 1, 2026, 11 pages.
EP: Communication pursuant to Article 94(3) EPC dated May 28, 2026 for European Patent Application 21 764 350.1, 7 pages.

* cited by examiner

INTRAVASCULAR DELIVERY SYSTEMS, DEVICES AND METHOD

CROSS-REFERENCE TO RELATED APPLICATIONS

This application is a continuation of U.S. patent application Ser. No. 18/680,773, filed May 31, 2024, which claims the benefit of priority to U.S. Provisional Patent Application No. 63/505,349, filed May 31, 2023 and titled IMPLANTS AND IMPLANT DELIVERY DEVICES, the disclosure of each of which is incorporated herein by reference in its entirety.

TECHNICAL FIELD

This present technology relates to delivery systems, devices and methods for delivering intravascular implants. In some embodiments, the implants are used to maintain a desired patency of a target vasculature.

BRIEF DESCRIPTION OF THE DRAWINGS

Features, aspects, and advantages of the presently disclosed technology can be better understood with regard to the following drawings.

DETAILED DESCRIPTION

I. Overview

Figure 1:
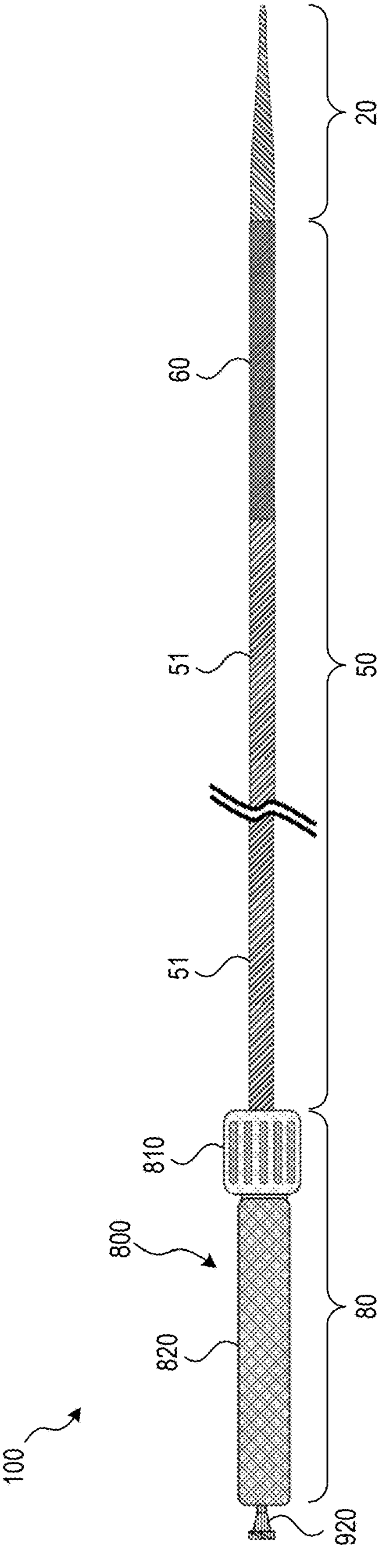
FIG. 1 shows an implant delivery device, in accordance with embodiments of the present technology.

Embodiments of the present technology relate to intravascular implants ("implants") and associated implant delivery devices for treatment of medical conditions stemming from vascular issues. Vascular issues can include blockages or abnormalities in arteries, veins, or vessels of a patient. Implants used to treat these conditions depend on the anatomical location of the vascular issue, or target vasculature. For example, multiple implants (e.g., stents) are generally used to treat medical conditions deriving from issues in the cardiothoracic, neurovasculature, abdominopelvic, and peripheral vasculature, since these anatomical locations consist of networks that are greater in length and highly branched. For example, excessive intercranial pressure, or more specifically the pressure of cerebrospinal fluid on vessel walls of the neurovasculature, can cause vessel walls to collapse and/or form arachnoid granulations, which reduce blood flow. As cerebrospinal fluid is absorbed into the neurovasculature through a pressure gradient, the cerebrospinal fluid pressure becomes greater than the intravascular pressure, reducing blood flow through the vessel. The reduced blood flow can cause a further increase in intravascular pressure, requiring an even higher amount of intracranial pressure for the cerebrospinal fluid to be absorbed, creating a vicious cycle of reduced blood flow and higher intracranial pressure. One or more shorter, circular in cross-section implants can be implanted into the vessel to restore drainage of the cerebrospinal fluid and alleviate pressure. However, in part due to implant/vessel flow mismatch, these implants can create turbulence and low-pressure zones within the implant and adjacent upstream or downstream areas of the vasculature, causing the vessel to collapse in these areas.

Technologies used to treat conditions in more complex anatomical regions can also include combining multiple implants of different lengths, diameters, or cross-sections. Although multiple implant constructs increase the area of coverage, delivery of implants of discrepant sizes with currently available delivery methods requires each implant be delivered one at a time, increasing the likelihood of mismatching implant size to the anatomical location and exposing patients to increased procedural risks. For example, delivery of an undersized implant can lead to implant migration, and delivery of an oversized implant can lead to vessel injury (e.g., vessel wall tears) and/or increased potential for implant adjacent vessel collapse.

Embodiments of the present technology include delivery devices having an implant used to maintain a desired patency of a target vasculature. The effect of the implant on patency of a target vasculature depends on various factors, including, the implant length, diameter, cross-sectional profile, flexibility, and ability to withstand different radial forces at one or more anatomical locations. For example, implants can have one or more zones that cover one or more anatomical locations within the target vasculature. The one or more zones can have varying parameters, such as radial forces, diameters, cross-sectional profiles, or flexibilities along the length of the implants. For example, the implants can have a patency zone that is less flexible and can conform in part to the vessel, and an inlet zone that is more flexible and conforms completely (or at least more than that of the patency zone) to the vessel. The inlet zone can be preshaped or conformable to provide less stress on the healthy portion of the vessel, preventing turbulence at the inlet of the implant and/or a low-pressure zone from forming, thereby reducing and/or eliminating vessel collapse upstream, and thus enabling better fluid flow through the implant. In some embodiments, the implants include one or more additional zones. For example, the implants can include an outlet zone that differs from one or both the inlet and patency zones.

In some embodiments, individual implants, each with one or more zones, are coupled together creating a longer implant. It can be advantageous to implant a singular longer implant, as opposed to multiple individual implants, since the longer implant can provide and/or resist the radial forces along a greater length of the target vasculature after one implantation, reducing procedure complexity and increasing patient safety. However, implants of greater length and/or varying flexibility are incompatible with current delivery devices. Thus, without compatible complex delivery devices, similar delivery complications described herein persist. Therefore, there is a need for safer and more efficient implant delivery devices configured to deliver and deploy one or more implants at various anatomical locations.

Embodiments of the present technology further include associated implant delivery devices, systems and methods that mitigate many of the issues described above and herein. An implant delivery system can include one or more implants and a compatible implant delivery device configured to maintain and deploy the implants. The system can be used to deliver and deploy implants within the body of a patient (e.g., a human or animal subject), or more specifically, along the length of a target vasculature. The delivery device can include an inner shaft and an outer shaft surrounding the inner shaft. The outer shaft can include a depression or recess configured to maintain the implants described above and herein. The delivery device can be customized to the target vasculature and/or to the implants by varying the lengths, diameters, cross-sectional profiles, or flexibilities of the inner and outer shafts. For example, the flexibility of the delivery device adjacent to the region containing the implant can closely match that of the region containing the implant, increasing maneuverability of the delivery device throughout the vasculature. Additionally or alternatively, the flexibility of the delivery device can be variable along the length of the delivery devices, enabling the implant delivery device to be adaptable to different anatomical regions encountered throughout the vasculature, from the insertion site to the target vasculature. In some embodiments, the delivery device is compatible with longer implants or multiple implants to treat portions of the vasculature including longer lesions and/or narrowing areas.

In some embodiments, the delivery device includes a lumen along an entire length of the delivery device configured to maintain a guide wire. The delivery device can further include one or more vents that expel air from within the delivery device during procedure preparation (i.e., prior to insertion of the delivery device into the vasculature). In some embodiments, the delivery device includes a deflectable and/or steerable distal tip portion. The distal portion can be controllable by a user via a proximal handle, further increasing maneuverability of the delivery device through the target vasculature. In some embodiments, the delivery device can include one or more sensors or electrical components to monitor navigation of the delivery device throughout the vasculature and deployment of the implants at the target anatomical region. For example, the delivery device can include sensors to monitor/measure physiological parameters, such as blood pressure and flow rates prior to, during, and/or after implant deployment. The delivery device can further be configured to rotationally orient the implants within the target vasculature. In some embodiments, the delivery device is configured to self-orient at the target anatomical region, enabling the implants to be deployed at a desired rotational orientation. In some embodiments, the handle is used to deploy or recapture the implants, allowing the user to adjust or reposition the implants if necessary.

In some embodiments, the system is used to deploy implants and treat conditions within the venous sinuses. For example, the delivery device can deliver and deploy implants to one or more of the transverse sinus, sigmoid sinus, and superior sagittal sinus while being atraumatic to fragile cortical veins that are easily damaged. In some embodiments, the delivery device includes a distal tip suitable for atraumatically navigating the target vasculature. The distal tip portion can have a high degree of flexibility such that throughout navigation, the distal tip does not puncture or disrupt the surrounding anatomy. For example, a delivery system used to deploy an implant in the venous sinuses can include a distal tip with the required flexibility to reduce the likelihood of damaging cortical veins throughout navigation.

The delivery device can also include one or more functional members that reduce the likelihood of delivery device elongation, provide compression/longitudinal resistance within the delivery device, and increase the tensile strength of the outer shaft. For example, the functional member can be a coil positioned within the outer shaft to provide compressive force across the implant, thereby reducing the likelihood of implant swelling and associated delivery risks. Additionally or alternatively, the functional member can be a braid positioned within the inner shaft and/or the outer shaft to increase the longitudinal stiffness of the delivery device and prevent elongation. In some embodiments, the delivery device includes one or more tensile members, such as one or more tensile fibers comprising aramid (e.g., Kevlar) and/or liquid crystal fibers (e.g., Vectran) positioned within the outer shaft to increase the total tensile strength of the outer shaft and prevent elongation. The tensile fiber can also be used in addition to one or more of the functional members described herein to increase tensile strength and/or reduce compression/elongation of the delivery device.

In some embodiments, implants and associated delivery devices of the present technology are related to treating disorders associated with narrowing of a blood vessel. As forementioned, in some embodiments, the present technology described herein is directed to delivering and positioning an implant in a venous sinus to maintain a desired patency of the venous sinus. However, the disclosed embodiments are merely examples of various embodiments of the present technology, and thus the disclosed embodiments can be used in other types of openings, channels, and/or vessels, such as cardiovascular, pulmonary vascular, and/or peripheral vascular blood vessels. Therefore, specific structural and functional details disclosed herein are not to be interpreted as limiting, but merely as a basis for the claims and as a representative basis for teaching one skilled in the art to make and use the systems, apparatuses, and methods in appropriately detailed structure. Furthermore, the terms and phrases used herein are not intended to be limiting, but rather they provide an understandable description of the systems, apparatuses, and methods.

In the Figures, identical reference numbers identify generally similar, and/or identical, elements. Many of the details, dimensions, and other features shown in the Figures are merely illustrative of particular embodiments of the present technology. Accordingly, other embodiments can have other details, dimensions, and features without departing from the spirit or scope of the disclosure. In addition, those of ordinary skill in the art will appreciate that further embodiments of the various disclosed technologies can be practiced without several of the details described below.

II. Devices, Systems and Methods for Delivery of Implants

FIG. 1 shows an implant delivery device 100 configured to deliver and deploy one or more implants (e.g., implants 1000 of FIGS. 5A-8B) to one or more target location in the vasculature. The delivery device 100 includes a handle region 80 used to maneuver the delivery device 100 throughout the vasculature, a shaft region 50 distal to and extending from the handle region 80, and a distal tip region 20 distal to and extending from the shaft region 50. The handle region 80 can include a handle 800 having a handle base 820 and a rotator 810, and the shaft region 50 can include a proximal shaft region 51 and an implant region 60 distal to the proximal shaft region 50. The rotator 810 can be coupled to a distal end of the handle base 820 and a proximal end of the shaft region 50, which includes an inner shaft (e.g., the inner shaft 120 of FIGS. 11-18B, 24, and 25) and an outer shaft (e.g., the outer shaft 500 of FIGS. 19-25), and as described herein. In operation, the rotator 810 can be actuated (e.g., rotated) to retract the outer shaft and deploy an implant, as described in more detail with reference to FIGS. 2A-2C. The proximal shaft region 51 and the implant region 60 can include one or more components (e.g., functional members) or configurations used to provide the delivery device with one or more of a desired flexibility, resistance to compression/elongation/swelling, and/or other general delivery device properties. In some embodiments, the delivery device 100 is also able to recapture the implant 1000 using the handle region 80 following deployment, as described in more detail with reference to FIGS. 29A-31. The delivery device 100 can further include a lumen port 920 that extends into a lumen (e.g., the lumen 205 of FIGS. 2A-2D) that spans an entire length of the delivery device 100. In some embodiments, the lumen port 920 is used to deliver a guide wire and/or to flush air from within the lumen 205.

Figure 2A:
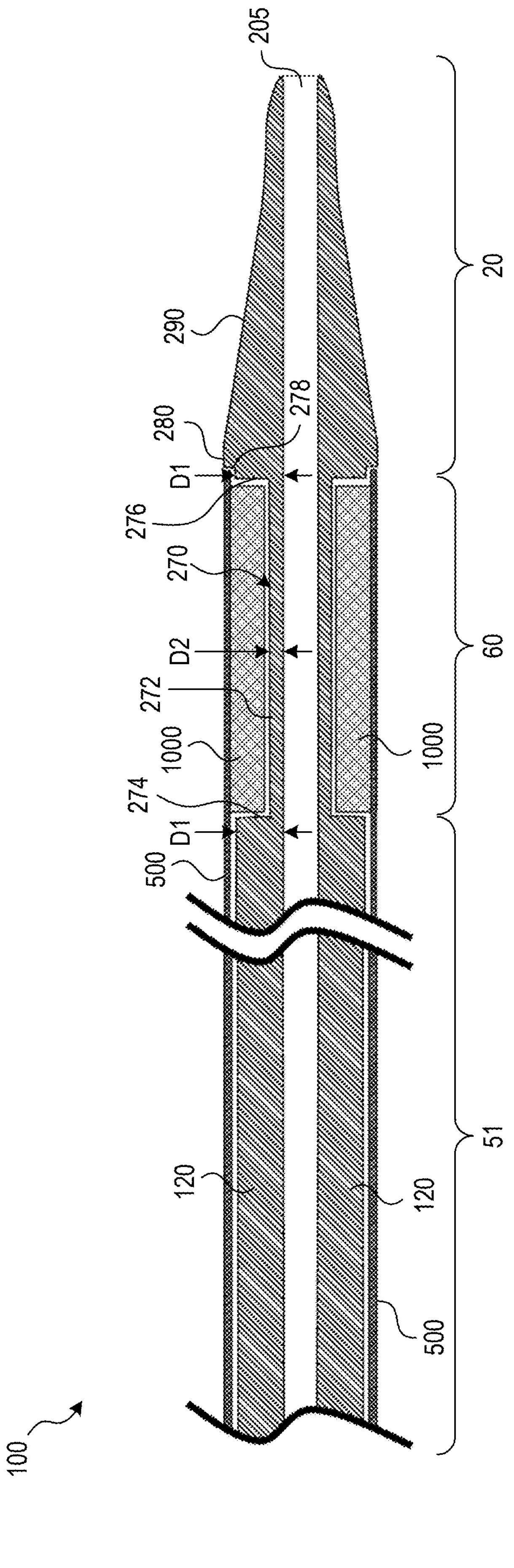
FIGS. 2A-2C show cross-sectional views of deployment of an implant from the implant delivery device of FIG. 1.
Figure 2B:
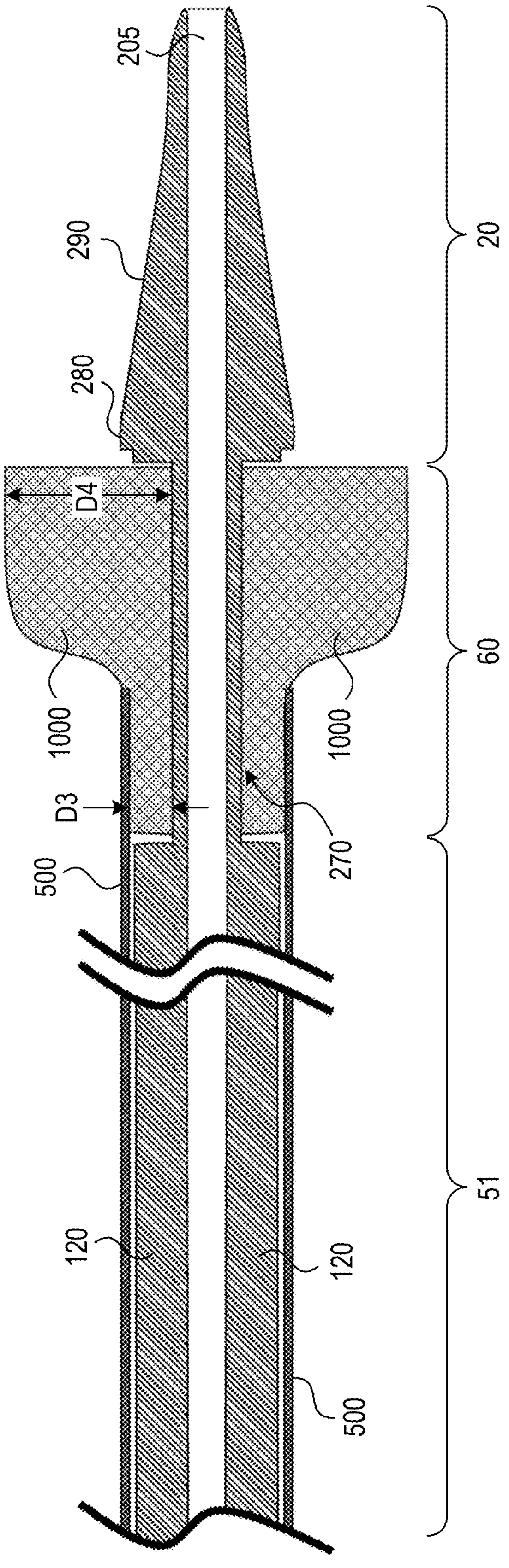
Figure 2C:
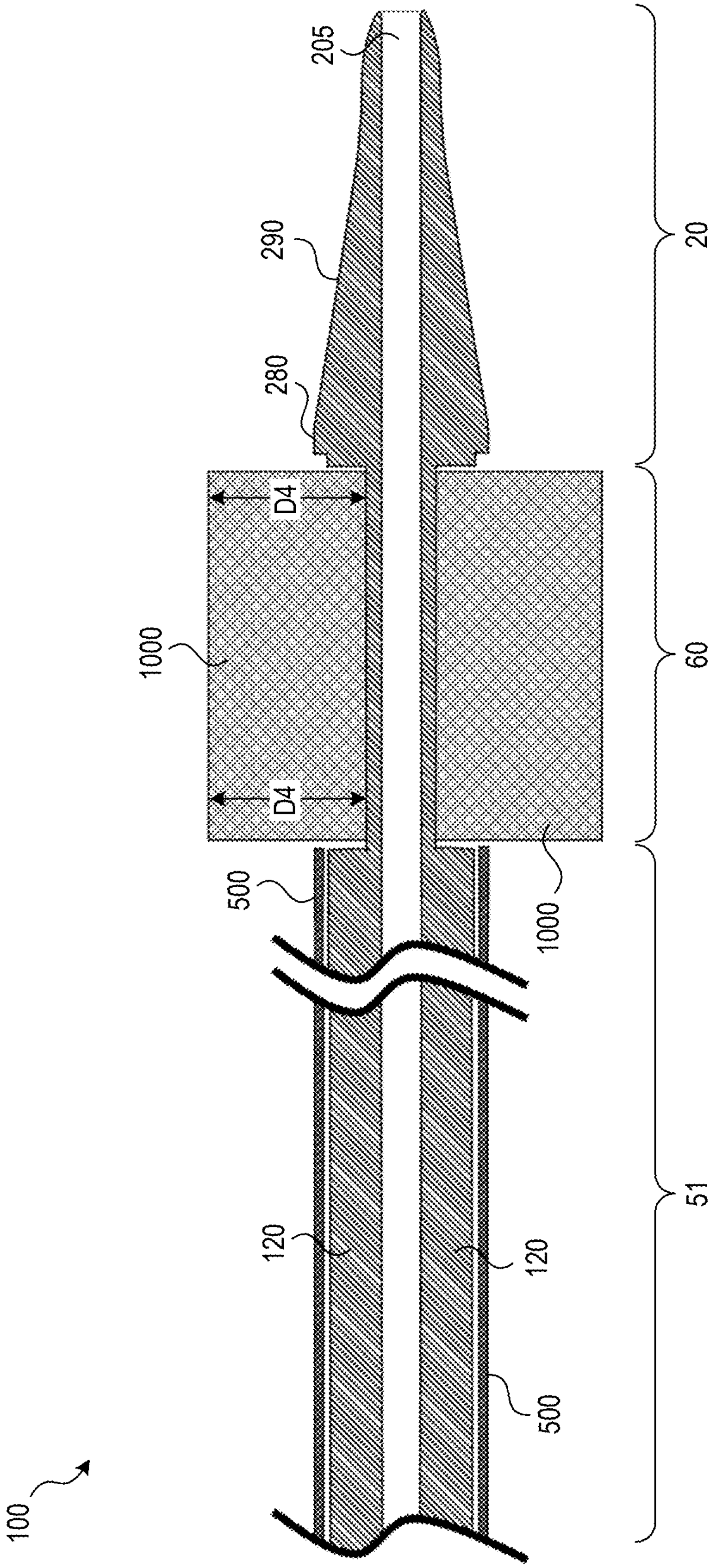

FIGS. 2A-2C show cross-sectional views of deployment of an implant 1000 from the delivery device 100 of FIG. 1. Referring first to FIG. 2A, the delivery device 100 can include a lumen 205, an inner shaft 120 outward of and at least partially defining the lumen 205, and an outer shaft 500 outward of the inner shaft 120 and proximally retractable relative to the inner shaft 120. The lumen 205 is accessible via the lumen port 920 of FIG. 1, that extends along an entirety of the length of the inner shaft 120. As shown in FIG. 2A, the implant 1000 can be maintained between the inner shaft 120 and the outer shaft 500 at the implant region 60.

The tip portion 20 is distal to the recess 270 and is generally tapered in the distal direction to have a decreasing cross-sectional dimension. In some embodiments, the distal tip or distal inner shaft (DIS) 280 ("distal tip 280") can have a length of at least 1.5 centimeters (cm), 2.0 cm, 2.5 cm, 3.0 cm, 3.5 cm, or 4.0 cm. Additionally or alternatively, a proximal region of the distal tip 280 can have a cross-sectional dimension within a range of 1.2-2.5 millimeters (mm), and a distal region of the distal tip 280 can have a cross-sectional dimension within a range of 0.5-1.2 mm. In some embodiments, at least half of the distal tip 280 (e.g., the combination of the distal and proximal regions) includes a cross-sectional dimension less than 2.5 mm. In some embodiments, the inner shaft 120 and the tip portion 20 are formed from a single material and/or have a continuous surface. Additionally or alternatively, the inner shaft 120 and the tip portion 20 are formed from different materials and have a continuous surface and/or a discontinuous surface.

The inner shaft 120 can have a cross-sectional dimension that varies along a length of the delivery device 100. For example, the inner shaft 120 can include a recess or recessed area 270 ("recess 270") configured to receive or maintain the implant 1000. The recess 270 can include a base recess surface 272, a proximal recess surface 274 proximal and angled relative to the base recess surface 272, and a distal recess surface 276 distal and angled relative to the base recess surface 272. In some embodiments, the proximal recess surface 274 can be normal (i.e., angled 90° relative) to the base recess surface 272. Additionally or alternatively, the distal recess surface 276 can have an angle of at least 90°, 95°, 100°, 110°, 120°, 135°, or more relative to the base recess surface 272, such that the distal recess surface 276 is tilted in the distal direction. Advantageously, the angle of the distal recess surface 276 relative to the base recess surface 272 can help prevent the implant 1000 from being caught at that area of the recess 270 once the implant 1000 is deployed, and the delivery device is removed from the patient. The recess 270 can be defined by a first cross-sectional dimension (D1) adjacent to either side of the implant 1000, and a second cross-sectional dimension (D2) that together form the recess 270 to receive the implant 1000. In some embodiments, D1 is generally large enough such that the portions of the inner shaft 120 adjacent to the implant 1000 act as a backstop to maintain the implant 1000 within the implant region 60 during delivery and deployment. In some embodiments, D1 is between 0.1 mm and 1.5 mm or any cross-sectional dimension therebetween, or at least 0.2 mm, 0.4 mm, 0.6 mm, or 0.8 mm, and D2 is between 0.1 mm and 1.5 mm or any cross-sectional dimension therebetween, or at least 0.2 mm, 0.4 mm, 0.6 mm, or 0.8 mm. In some embodiments, the outer diameter of the outer shaft 500 is between 0.75 mm and 3.0 mm, or any outer diameter therebetween, or at most 0.75 mm, 1 mm, 1.25 mm, 1.5 mm, 1.75 mm, 2 mm, 2.5 mm, or 3 mm. In some embodiments, the outer diameter of the inner shaft 120 is between 0.5 mm and 2.5 mm, or any outer diameter therebetween, or at most 0.5 mm, 0.75 mm, 1 mm, 1.25 mm, 1.5 mm. 1.75 mm, 2 mm, or 2.5 mm. In some embodiments, the outer diameter of the recess 270 is between 0.25 mm and 2.0 mm, or any outer diameter therebetween, or at most 0.25, 0.5 mm, 0.75 mm, 1 mm, 1.25 mm, 1.5 mm. 1.75 mm, or 2.0 mm. The recess 270 can maintain the position of the implant 1000 with respect to the delivery device 100 during navigation to the target site and also during deployment of the implant 1000.

The delivery device 100, or more specifically the inner shaft 120 or distal tip 280, can further include a ledge 278 distal to and extending from the recess 270. The ledge 278 can be angled (e.g., normal to) the distal recess surface 276 and/or substantially parallel to the base recess surface 272. As shown in FIG. 2A, a distal terminus of the outer shaft 500 can be disposed over the ledge 278 when the implant 1000 is in the constrained state within the recess 270. In some embodiments, the recess 270 has a length between 2 centimeters (cm) and 15 cm, or at least 6 cm, 8 cm, 10 cm, or 15 cm.

In some embodiments, the implant 1000 can self-expand from a constrained state, exerting a radially outward force onto the outer shaft 500, to an unconstrained state. The outer shaft 500 can be configured to withstand the radially outward force applied by the implant 1000 such that the implant 1000 is not deployed until reaching the target site, decreasing the likelihood of unwanted deployment and increasing patient safety. In some embodiments, the outer shaft 500 withstands a radial outward force applied by the implant 1000 between 0.1 N/mm and 10 N/mm, or at least 0.1 N/mm, 0.25 N/mm, 0.5 N/mm, 1 N/mm, 2 N/mm, 5 N/mm, or 8 N/mm. For example, as the outer shaft 500 is retracted (i.e., moved proximally with respect to the inner shaft 120 within the implant region 60), the outer shaft 500 resists elongation, enabling accurate deployment of the implant 1000. Additionally or alternatively, the outer shaft 500 can be configured to prevent the implant 1000 from stretching and/or wedging between the outer shaft 500 and the inner shaft 120 outside of the implant region 60. In some embodiments, the inner shaft 120 is configured to maintain the longitudinal position of the implant 1000 while the outer shaft 500 is retracted. For example, the portion of the inner shaft 120 proximal to the implant 1000 can be configured to maintain the longitudinal position of the implant 1000 as the outer shaft 500 is retracted and the implant 1000 tries to move proximally (i.e., by applying a radial force to the outer shaft 500).

Still referring to FIG. 2A, the outer shaft 500 fully constrains the implant 1000, as it would be when delivered to the target site. The outer shaft 500 can be retracted allowing the implant 1000 to self-expand (e.g., to a specified diameter/cross-sectional profile). As shown in FIG. 2B, the outer shaft 500 can be partially retracted at the implant region 60 such that the implant 1000 can expand from a cross-sectional dimension (D3) to a cross-sectional dimension (D4). In some embodiments, D3 is between 0.1 mm and 2 mm or any cross-sectional dimension therebetween, or at most 0.1 mm, 0.2 mm, 0.3 mm, 0.5, or 1.0 mm, and D4 is between 1 mm and 5 mm or any cross-sectional dimension therebetween, or at least 1.5 mm, 2.0 mm, 2.5 mm, 3.0, mm, 3.5 mm, or 4.0 mm. D3 can be generally small enough such that the delivery device 100 can navigate through the target vasculature to the target site, and D4 can be generally large enough to mate with the target site vessel wall. FIG. 2C shows the outer shaft 500 retracted proximally beyond the implant region 60 such that the implant 1000 is fully deployed and has a cross-sectional dimension (D4) along an entirety of the length of the implant 1000. It is worth noting that although the implant 1000 illustrated appears to include the same cross-sectional dimension along the entire length, the delivery device 100 can be used to deploy one or more implants including one or more cross-sectional dimensions and/or other parameters, as described in more detail with reference to FIGS. 5A-9C.

Figure 3:
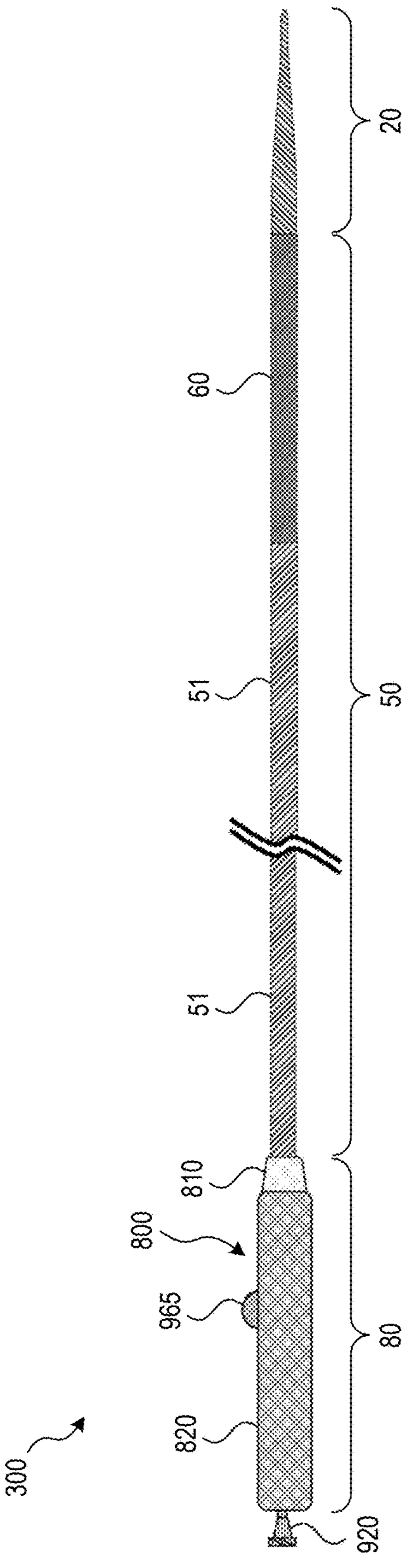
FIGS. 3 and 4 show additional implant delivery devices, in accordance with embodiments of the present technology.
Figure 4:
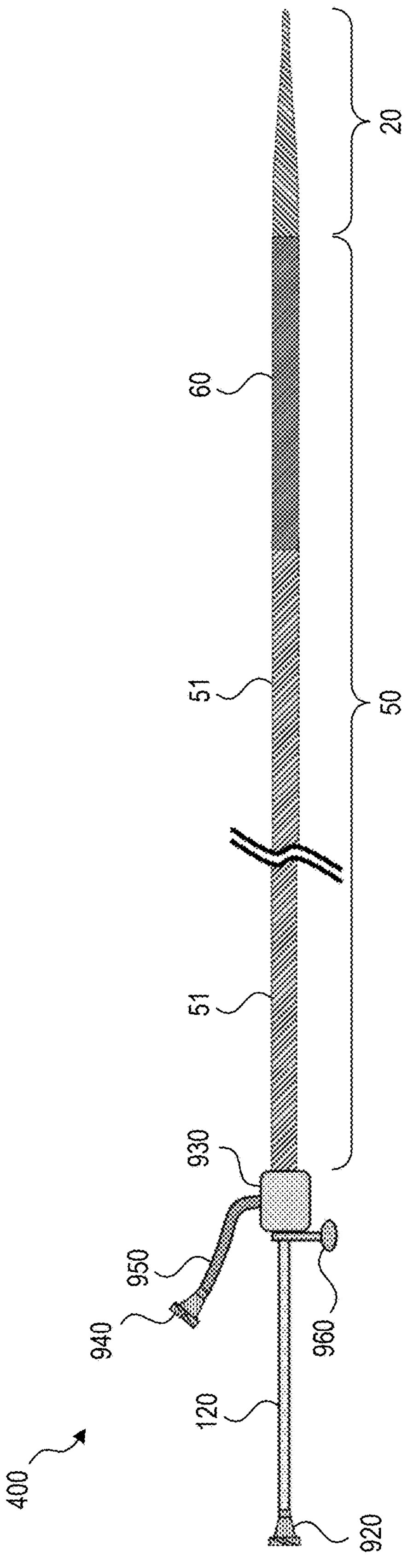

FIGS. 3 and 4 show respective delivery devices 300, 400. The devices 300, 400 of FIGS. 3 and 4 can include identical or generally similar components to the delivery device 100. As shown in FIG. 3, the delivery device 300 includes a thumbwheel 965 on the handle 800. The thumbwheel 965, as opposed to the rotator 810 of FIG. 1, can be used to retract the outer shaft 500 along the length of the implant region 60.

As shown in FIG. 4, the delivery device 400 can omit a handle entirely (e.g., the handle 800 of FIG. 1) and can instead include a pullback retraction mechanism. For example, the pullback retraction mechanism can include a hub 930, a second lumen port 940, a port tube 950, and a lock 960. The second lumen port 940 can be identical or generally similar to the lumen port 920. In some embodiments, the lumen port 920 is configured to maintain a guide wire and the second lumen port 940 and the port tube 950 are used to flush from within the delivery device 400, or vice versa. To retract the outer shaft 500 along the length of the implant region 60 and deploy the implant (e.g., the implant 1000 of FIGS. 2A-2D), the hub 930 can be proximally pulled towards the lumen port 920. Additionally or alternatively, the hub 930, or another other location on or within the delivery devices 100, 300, 400 can include a lock 960, to prevent unwanted movement of the inner shaft 120 with respect to the outer shaft 500. For example, the pull back mechanism can be used to maintain position of the inner shaft 120 relative to the outer shaft 500 prior to deployment (e.g., during shipping, preparation, navigation prior to reaching the target location). In some embodiments, the hub 930 has a fluid seal that allows the inner shaft (e.g., the inner shaft 120 of FIGS. 2A-2C) to move with respect to the hub 930 and outer shaft 500. The area between the inner shaft 120 and outer shaft 500 can be flushed with fluid (e.g., saline) via the second lumen port 940 (e.g., a Luer fitting) and the port tube 950.

III. Intravascular Implants

Figure 5A:
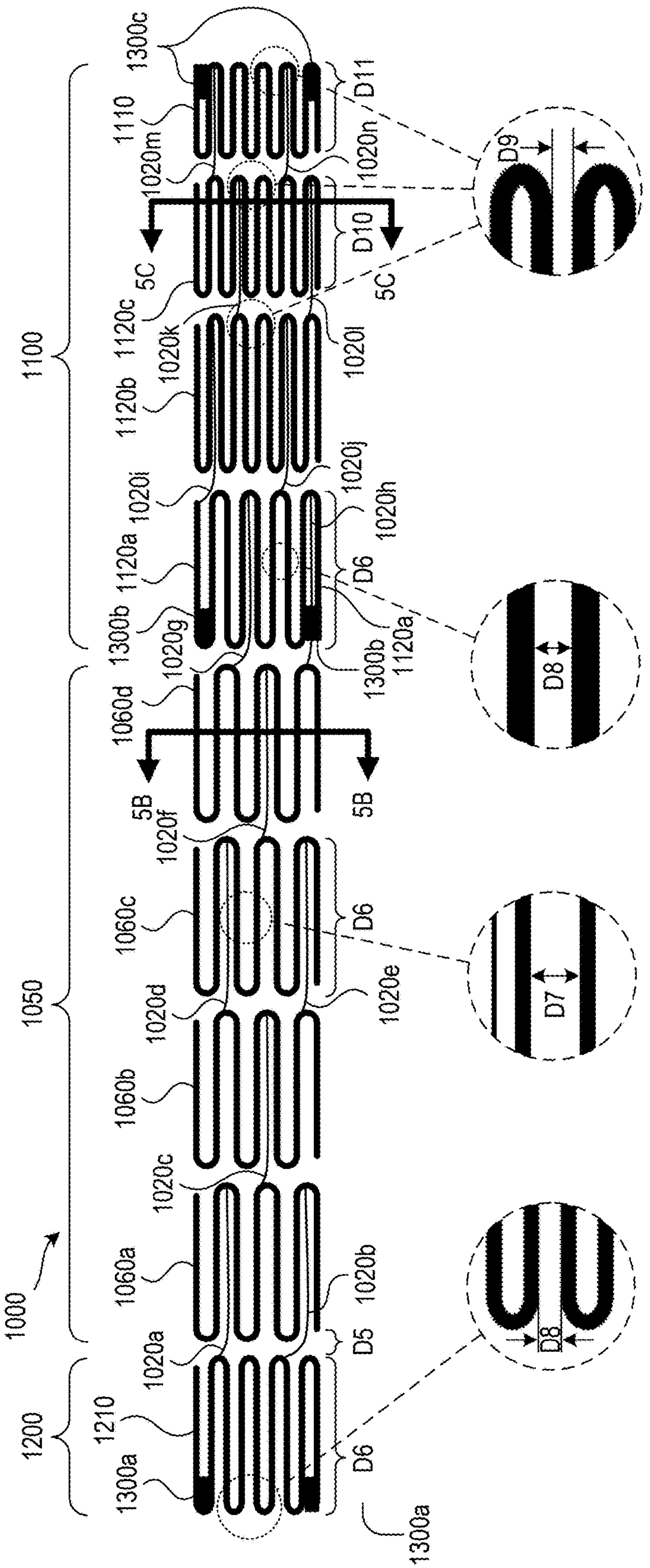
FIGS. 5A-9C show intravascular implants, in accordance with embodiments of the present technology.

FIGS. 5A-9C show various implants 1000 that can be delivered with the delivery devices (e.g., delivery device 100) described herein. As shown in FIG. 5A, the implant 1000 can include one or more implant regions or zones. For example, the implant 1000 can include a first zone 1050, a second zone 1100 distal to the first zone 1050, and a third zone 1200 proximal to the first zone 1050. As shown in FIG. 5A, the first zone 1050 can include one or more first zone rings or structures 1060*a*-1060*d* (collectively referred to as "first zone structures 1060"). The first zone structures can be coupled to one another by couplers 1020*a*-1020*f* ("collectively referred to as coupler 1020"). In some embodiments, the first zone 1050 is configured to have a radial force sufficient to open and hold open the vessel under highest anticipated forces (e.g., external forces from a collapsed vessel and/or internal forces from an intravascular blockage, such as arachnoid granulations). Additionally or alternatively, the first zone 1050 can be configured to have a radial force that is compatible with expansion force requirements, for example, to open a narrowing target to maintain sufficient fluid and/or blood flow throughout the vessel. The first zone structures 1060 can be consistent or varying in properties. As such, the first zone 1050 can be divided further into subregions with varying parameters (e.g., varying radial forces, diameters, etc.). In addition, the couplers 1020 can have consistent or varying parameters. The number of the couplers 1020 coupling the first zone structures 1060 can vary along the length of the implant 1000. For example, one or more of the first zone structures 1060 adjacent to one another can be coupled with one or more of the couplers 1020.

The first zone 1050 can generally cover at least the target treatment area (e.g., the narrowing) of the vessel. As such, the radial force exerted by the first zone 1050 can be sufficient to open the vessel and/or resist significant radial compression from the forces applied to it by the vessel, pressures (e.g., cerebral spinal fluid), blockages, etc. The length of the first zone 1050, depending on the desired area of coverage, can extend from between 5 mm to 200 mm or at least 5 mm, 80 mm, 100 mm, 150 mm, or 200 mm in length. The first zone 1050 can further include one or more subregions with varying radial force and/or flexibility. The first zone structures 1060 can have a longitudinal dimension (D6), that is between 0.5 mm and 10 mm, or at least 0.5 mm, 2.5 mm, 5 mm, 7 mm, or 10 mm.

In some embodiments, the second zone 1100 is coupled to the first zone 1050 by couplers 1020*g* and 1020*h* (collectively referred as "couplers 1020"). As shown in FIG. 5A, the second zone 1100 can include one or more second zone end rings or structures 1110 the second zone 1100 can include one or more second zone end structures 1110 ("second zone end structure(s)" 1110) and one or more the second zone transition rings of structures 1120*a*-1120*c* (collectively referred to as "second zone transition structures 1120"). The second zone transition structures 1120 can couple one another and the second zone end structure(s) 1110 by couplers 1020*i*-1020*n* (collectively referred as "couplers 1020"). In some embodiment, the second zone end structures 1110 can have a different radial force and/or flexibility than the first zone structures 1060 and/or the second zone transition structures 1120, such as a typically lower radial force and/or more flexibility to adapt to the vessel shape and mitigate changing the native shape of the vessel more readily. This also allows the second zone end structures 1110 to match or substantially match the vessel cross-sectional profile adjacent the implant 1000 when deployed. Additionally or alternatively, the second zone end structures 1110 can be configured with a different cross-sectional profile (including larger or smaller cross-sectional profiles compared to that of the first zone structures 1060). The second zone transition structures 1120 can provide a transition between the first zone 1050 and the second zone end structures 1110. The transition can include a varying radial force, flexibility, and/or cross-sectional profile, and can occur discretely (e.g., in one or more steps), continuously, or a combination thereof. The second zone 1100 can be further divided into subregions with varying properties. The second zone 1100 enables the implant 1000 to have varying properties which can help match the cross-sectional profile along at least a portion of the target vasculature, improving fluid flow adjacent and within the implant, and optimizing forces exerted on the vessel and adjacent tissues. The number of couplers 1020 can be constant or vary along the length of the implant 1000. As shown in FIG. 5A, the coupler 1020*d* connects a "peak" on first zone structure 1060*b* to a "valley" on first zone structure 1060*c*. For example, there can be six peaks on first zone structures 1060*b*, 1060*c* and three couplers 1020 connecting these two structures. Similarly, there can be nine peaks and three couplers 1020, twelve peaks and four couplers 1020, or any combination of peaks between the zone structures 1060, 1110, 1210 and couplers 1020.

Figure 6A:
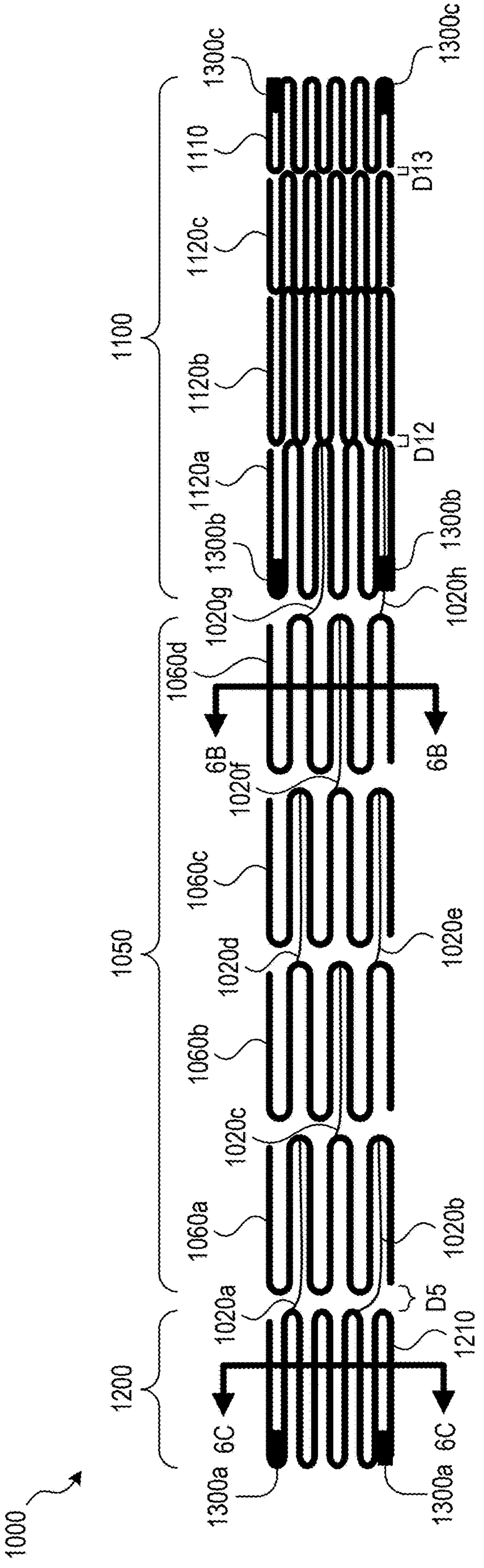
Figure 7A:
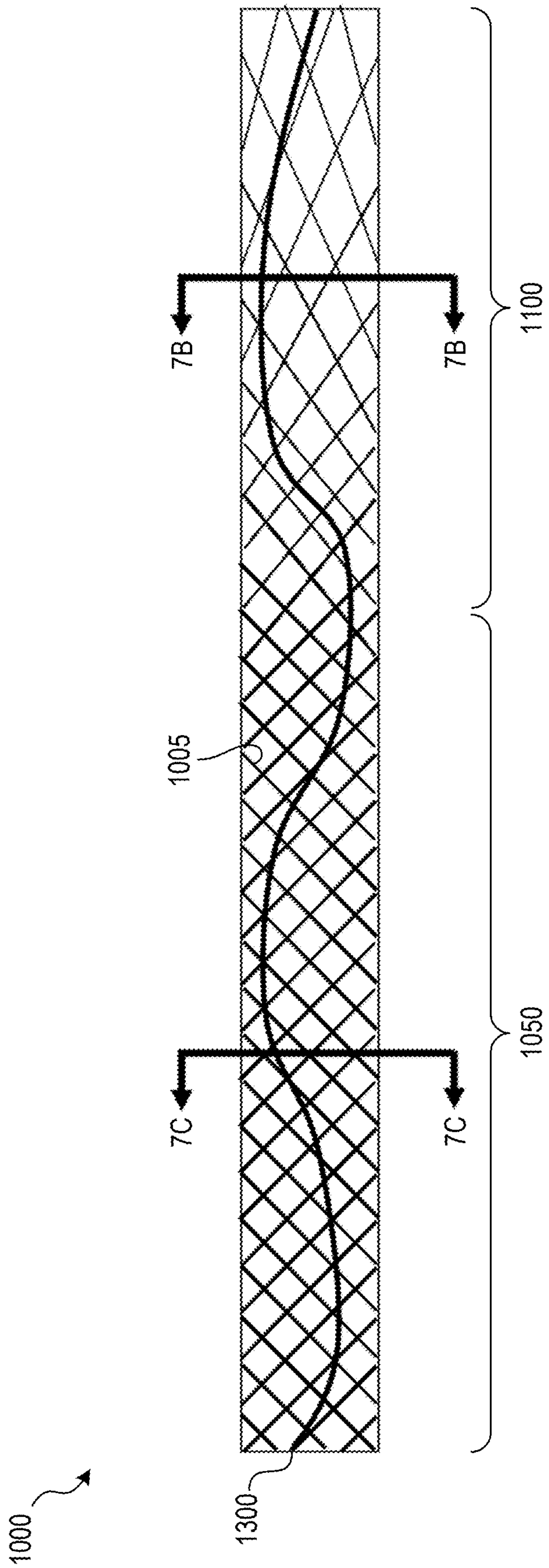
Figure 8A:
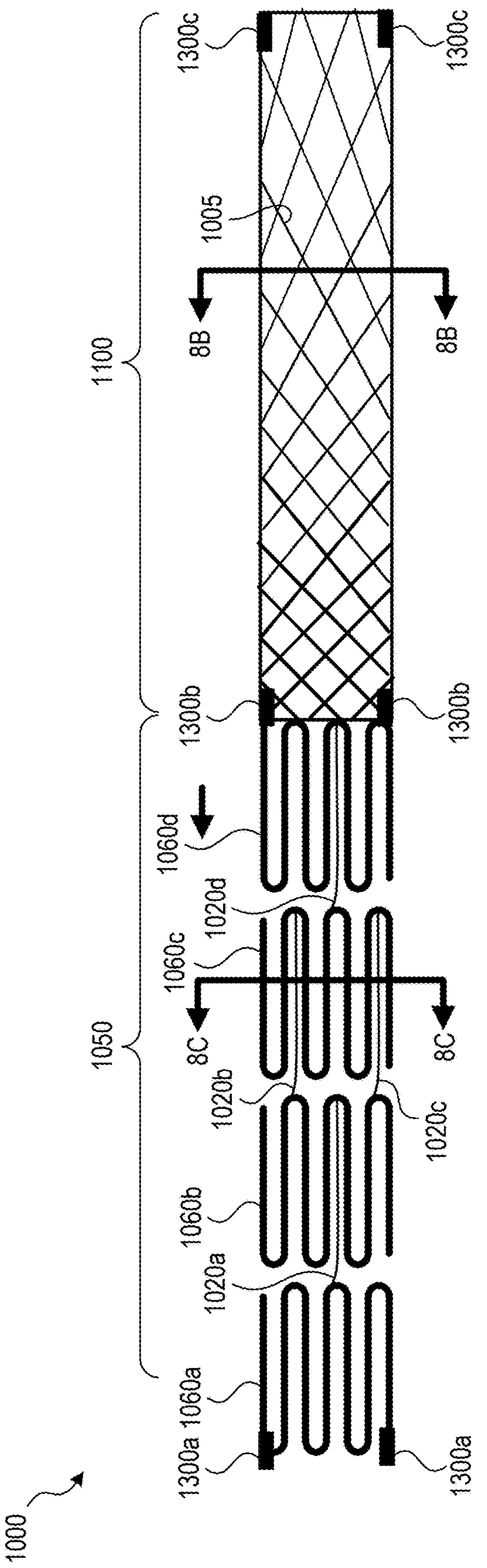

In some embodiments, and as shown in FIGS. 6A, 7A, and 8A, the structures (e.g., the first zone structures 1060, the second zone transition structures 1120, and/or the second zone end structures 1110) between and/or within the first zone 1050 and/or the second zone 1100 are positioned directly adjacent to one another without the couplers 1020. In some embodiments, the second zone transition structures 1120 and the second zone end structures have longitudinal dimensions (D10 and D11) that are equivalent, more, or less than the longitudinal dimension (D6) of the first zone structures 1060. For example, the longitudinal dimensions (D10 and D11) can be between 0.5 mm and 10 mm, or at least 0.5 mm, 2.5 mm, 5 mm, 7 mm, or 10 mm. In some embodiments, the length of the second zone end structures 1110 coupled to one another can be between 2 mm and 25 mm, or at least 2 mm, 5 mm, 10 mm, or 15 mm. If included the length of the second zone transition structures 1120 coupled to one another can similarly be a length between 2 mm and 25 mm, or at least 2 mm, 5 mm, 10 mm, 15 mm, or 25 mm.

The second zone 1100 can occupy a distal or upstream end (i.e., an inlet) of the implant 1000 relative to the first zone 1050. The length of the second zone 1100, depending on the target placement of the implant 1000, can extend from between 0.5 mm to 40 mm, or at least 0.5 mm, 5 mm, 10 mm, 15 mm, 20 mm, or 40 mm. As shown in FIGS. 5B and 5C, 6B and 6C, 7B and 7C, 8B and 8C, and 9A and 9B respectively, the diameter or perimeter of the second zone 1100 is generally equivalent to or less than the first zone 1050. In addition, at least a portion of the second zone 1100 can take at least a similar shape as to the vessel in which it is implanted, and in some embodiments, it takes a shape that is substantially similar to the vessel. The second zone 1100 can include one or more subregions with varying radial force, flexibility, and/or cross-sectional profile. The radial force can change over the length of the second zone 1100, for example, within the second zone transition structures 1120, to accommodate a smooth transition from the native vessel. In some embodiments, a singular structure has variable radial force along its longitudinal length to accommodate for target vascular conditions. The radial forces in of the second zone transition structures 1120 and/or the second zone end structures 1110 can be between 0.001 N/mm and 3 N/mm, or between 0.001 N/mm, 0.25 N/mm, 0.5 N/mm, 0.75 N/mm, or 3 N/mm.

In some embodiments, the implant 1000 can include a third zone 1200 that is coupled to the first zone 1050 with or without couplers 1020. The third zone 1200 can have different properties (e.g., radial force and/or flexibility) than the first zone 1050 and/or the second zone 1100, enabling the third zone 1200 to potentially case the transition from the first zone 1050 to the vessel and/or match the vessel cross-sectional profile adjacent the implant 1000 more readily when deployed. Additionally or alternatively, the third zone 1200 can provide a different cross-sectional profile (including larger or smaller cross-sectional profile compared to the first zone 1050). The third zone 1200 can include transition structures as described herein with reference to the second zone 1100. Any transition structures or combination of transition structures can have various radial force and/or flexibility, cross-sectional profile, and can occur discreetly (e.g., in one or more steps), continuously, or a combination thereof. The third zone 1200 can be divided into subregions with varying properties. The third zone 1200 can provide the implant 1000 with additional varying properties which can help match the cross-sectional profile along at least a portion of the target vasculature, improve blood flow adjacent and within the implant 1000, and optimize forces exerted on the vessel and adjacent tissues.

The third zone 1200 generally extends from the first zone 1050 to the downstream end of the implant 1000. The length of the third zone 1200 can between 0.5 mm and 40 mm, or at least 0.5 mm, 5 mm, 10 mm, 15 mm, 20 mm, 22 mm, or 40 mm. The diameter or perimeter of the third zone 1200 can be larger than, equivalent to, or less than the first zone 1050. In addition, at least a portion of the third zone 1200 can take at least a similar shape as to the vessel in which it is implanted. The radial force can change over the length of the third zone 1200 to accommodate a smooth transition to the native vessel. The radial forces in of the third zone 1200 can be between 0.001 N/mm and 4 N/mm, or between 0.001 N/mm, 0.25 N/mm, 0.5 N/mm, 0.95 N/mm, or 4 N/mm. It is worth noting that although a singular third zone structure is depicted in FIGS. 5A and 6A, the third zone can include one or more third zone structures 1210 to one another and to the first zone structures 1060 using one or more couplers 1020, as described herein. Similar to the first zone 1050 and second zone 1100, the third zone 1200 can include one or more subregions with varying radial force and/or flexibility by varying properties of the third zone structures 1210. Additionally or alternatively, the third zone structures 1210 can have a longitudinal dimension (D6) that is between 0.5 mm and 10 mm, or at least 0.5 mm, 2.5 mm, 5 mm, 7 mm, or 10 mm.

In some embodiments, the implant 1000 can have more than three zones to optimize parameters/performance/safety depending on the target vessel and location/coverage of the implant 1000. For example, the implant 1000 can have a second zone 1100, a first zone 1050, another region similar to the second zone 1100, another region similar to the first zone 1050, and/or potentially the third zone 1200. In some embodiments, the implants 1000 can be made of self-expanding material, such as NiTi or NiTi alloys. Additionally or alternatively, the implants 1000 can be balloon implants or mechanically expandable and/or made of other materials that are not self-expanding.

Referring to FIGS. 5A-9C collectively, the implant 1000 can also include one or more radiopaque markers 1300*a*-1300*c* (collectively referred to as "radiopaque markers 1300"). The radiopaque markers 1300 can be incorporated into one or more zones (e.g., the first zone 1050, the second zone 1100, and/or the third zone 1200) of the implant 1000 to increase visualization of the implant 1000 under imaging/fluoroscopy. The radiopaque markers 1300 can be continuous, discrete, or any combination thereof. Additionally, or alternatively, the radiopaque markers 1300 can be positioned between the one or more zones of the implant 1000 to identify distal or proximal end regions, transition regions, and/or other properties of the implant 1000.

Figure 5B:
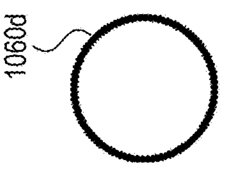
Figure 5C:
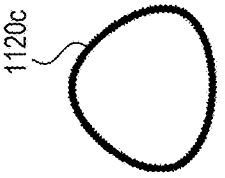

Referring now to FIGS. 5A and 5B, the implants 1000 can be round in cross-section when constrained within the delivery device 100. Additionally or alternatively, and as shown in FIGS. 5C-6C, the implants 1000 can be non-round in cross-section when constrained within the delivery device 100. The implants 1000 can also have different shapes when deployed within the target vessel. The implants 1000 can be generally round in cross-sectional profile (e.g., as shown in FIG. 5B) when constrained within the delivery device 100 or when expanded in free space. However, once the implant 1000 is deployed within the target vessel, the cross-sectional profile of the implant 1000 can expand or conform to and/or resemble at least in part that of the target vessel (e.g., as shown in FIG. 5C). The implants 1000 can have one or more zones (e.g., zones 1050, 1100, 1200) which vary in properties, such as radial forces, diameters/cross-sectional profiles, flexibility, and construction that allow the implant 1000 to conform to the target vasculature.

In some embodiments, the implant 1000 includes an open-cell configuration (e.g., as shown in FIG. 5A), a mix of open-cell and closed-cell (e.g., as shown in FIG. 6A), or a completely closed cell design. As shown in FIG. 5A, the open-cell design can include one longitudinal dimension (D5) between the structure(s) 1110, 1120, and/or 1210. The longitudinal dimension (D5) can be between 0.01 mm and 2 mm, or at least 0.01 mm, 0.1 mm, 0.2 mm, 0.5 mm, 1 mm, or 2 mm. As shown in FIG. 6A, the closed cell configuration can be formed by directly coupling the structure(s) 1110, 1120, and/or 1210 to adjacent structures without the use of couplers 1020. The mix of open-cell and closed-cell configurations can include one or more longitudinal dimensions (D5, D12, and D13) between the structure(s) 1110, 1120, and/or 1210 that generally decrease in dimension transitioning from the open-cell configuration to the closed-cell configuration. The longitudinal dimensions (D12 and D13) can be between 0 mm and 2 mm, or at most 0.1 mm, 0.2 mm, 0.5 mm, or 2 mm.

In some embodiments, the structure(s) 1110, 1120, and/or 1210 are made of filament fibers that are wound or folded to be generally more or less compact such that the one or more zones of the implant 1000 conform to the target vasculature. As shown in FIG. 5A, the first zone structures 1060 can have a cross-sectional dimension (D7) between the wound filaments that is between 0.5 mm and 10 mm, or at most 0.5 mm, 1 mm, 2.5 mm, 5 mm, or 10 mm. The third zone structures 1210 and second zone transition structures 1120 can have a cross sectional dimension (D8) between the wound filaments that is generally smaller than the cross-sectional dimension (D7) of the first zone structures 1060. The cross-sectional dimension (D8) can be between 0.5 mm and 4 mm, 0.5 mm, 1 mm, 2 mm, or 4 mm. In some embodiments, the second zone end structures 1110 includes a cross-sectional dimension (D9) that varies from the cross-sectional dimension (D8) and between 0.1 mm and 4 mm, or at most 0.1 mm, 0.5 mm, 1 mm, 1.5 mm, 2 mm, or 4 mm.

Figure 7B:
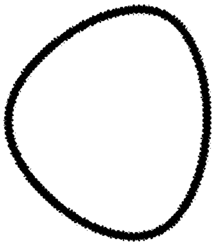
Figure 7C:
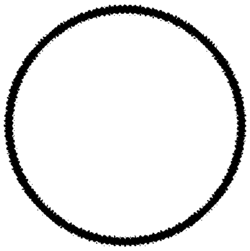

The implant 1000 can have a braided structure either in lieu of or in addition to structures (e.g., the structures 1060, 1120, and/or 1110) described herein. As shown in FIG. 7A, the first zone 1050 can include a single pitch braid, a variable pitch braid with varying wires, strands, properties, parameters, or dimensions across a length of the first zone 1050. For example, as the first zone approaches the second zone 1100, the pitch braid can be more conformal to the vessel. As shown in FIG. 7C, the first zone 1050 can have a generally more round horizontal cross-section in both a free unconstrained state and/or constrained state. The first zone 1050 can, at least in part, take the shape of the target vessel. The second zone 1100 can also include a variable pitch braid with transitioning properties, especially near the inlet side of the implant, to conform to the shape of the native vessel. As shown in FIG. 7B, the second zone 1100 can have a horizontal cross-section that is more conformal to the vessel than the first zone 1050. In some embodiments, the implant 1000 include a radiopaque marker 1300 (e.g., a radiopaque filament) that can be woven through the closed cells to enable an additional type of radiopacity. It can be advantageous for the radiopaque marker 1300 to be interwoven into the implant 1000, as opposed to the individually position markers, since the interwoven markers are generally more discrete. The first zone 1050 can transition from a more closed cell region to a less closed cell region. The closed cell region (e.g., regions where the filaments are generally more closely woven together) can allow for partial deployment of the implant 1000 and retrieval if so desired.

Figure 8B:
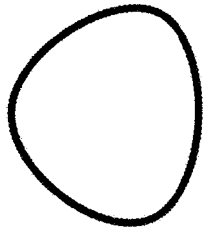
Figure 8C:
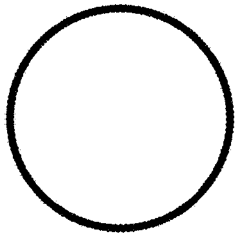

As described with reference to FIGS. 5A and 6A, the implants 1000 of FIGS. 7A, 8A, and 9A can also be constructed of one or more open cell regions, one or more closed cell regions, or any combination thereof. For example, as shown in FIG. 8A, the first zone 1050 can include an open cell construction and the second zone 1100 can include a closed-cell construction. The implant 1000 can be constructed with one or more open cell regions, one or more closed cell regions, or any combination thereof. The first zone 1050 can be round in both a free unconstrained state and a constrained state (e.g., as shown in FIG. 8C). Additionally, or alternatively, the first zone 1050 can, at least in part, take the shape of the vessel (e.g., as shown in FIG. 8B). The second zone 1100 is shown with a variable pitch braid to form a transition and enable that region, especially near the inlet side, to conform to the shape of the native vessel (e.g., as shown in FIG. 8B) more readily. In some embodiments, the first zone 1050 can be more round or less conformal to the vessel than the second zone 1100.

Figure 9A:
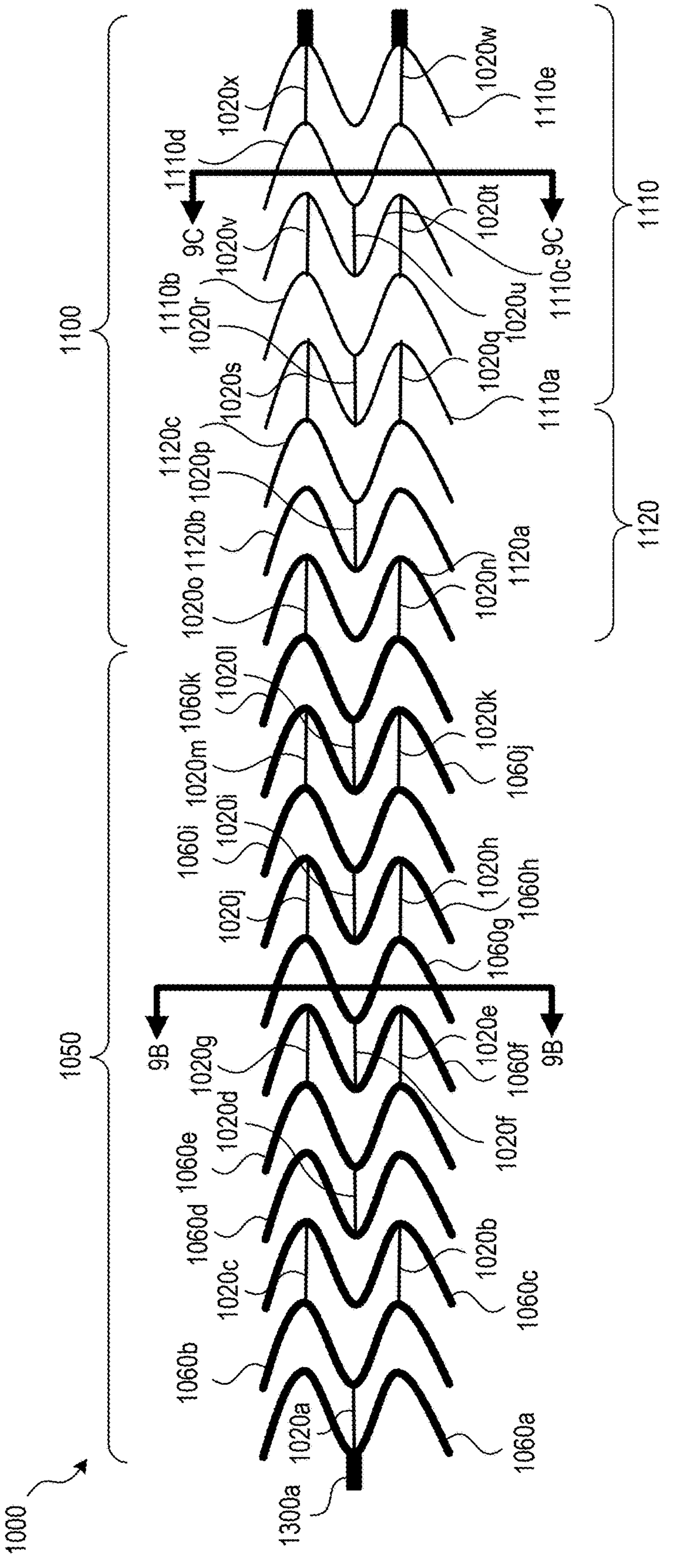
Figure 9B:
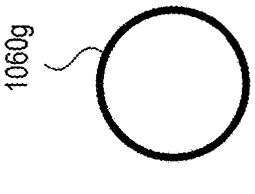
Figure 9C:
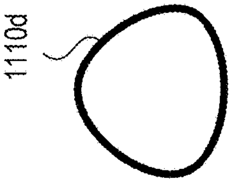

As shown in FIGS. 9A-9C, the implant 1000 can be configured to be round in the free unconstrained state with an overall length between 2 cm and 15 cm or any length therebetween, or between 2 cm, 5 cm, 6 cm, 8 cm, 10 cm, or 15 cm. The first zone 1050 of the implant 1000 can be between 1 cm and 14 cm in length or any length therebetween, or at most 1 cm, 2.5 cm, 5 cm, 10 cm, or 14 cm. The diameter of the first zone 1050 can be between 0.5 mm and 10 mm or any diameter therebetween, or at least 0.5 mm, 2.5 mm, 5 mm, 6 mm, 8 mm, or 10 mm. The first zone 1050 can include one or more first zone structures 1060 configured with between 4 structures and 100 structures, or any number of structures therebetween, or at least 4, 20, 40, 60, 80, or 100 structures. The one or more first zone structures 1060*a*-1060*k* (collectively referred to as "first zone structures 1060") can be coupled to one another by one or more couplers 1020*a*-1020*x* (collectively referred to as "couplers 1020"). In some embodiments, three of the couplers 1020 are used to couple any pair of the first zone structures 1060. The second zone 1100 of the implant 1000 can include one or more second zone transition structures 1120*a*-1120*c* (collectively referred to as "second zone transition structures 1120") and one or more second zone end structures 1110*a*-1110*e* (collectively referred to as "second zone end structures 1110") also coupled to one another by the couplers 1020. The second zone 1100 can be between 5 mm and 50 mm in length or any length therebetween, or at most 5 mm, 10 mm, 15 mm, 20 mm, 25 mm, or 50 mm. The diameter of the second zone 1100 can be between 0.5 mm and 10 mm or any diameter therebetween, or at least 0.5 mm, 2.5 mm, 5 mm, 6 mm, 8 mm, or 10 mm. In some embodiments, the second zone 1100 can be configured with various properties that accommodate the variable radial force of the target anatomy. The second zone end structure(s) 1110 can be between 5 mm and 25 mm in length or any length therebetween, or at most 5 mm, 10 mm, 15 mm, 20 mm, or 25 mm. The second zone end structure(s) 1110 can be configured to roughly conform to the shape of the native vessel, taking a somewhat triangular shape in cross-section (as shown in FIG. 9C) to navigate through tortuous anatomy. As shown in FIGS. 9B and 9C, the cross-sectional profile of the implant 1000 from the second zone end structure(s) 1110 to the second zone transition structures 1120 to the first zone 1050 can be gradually more circular.

IV. Delivery Devices for Delivery of Implants

Figure 10:
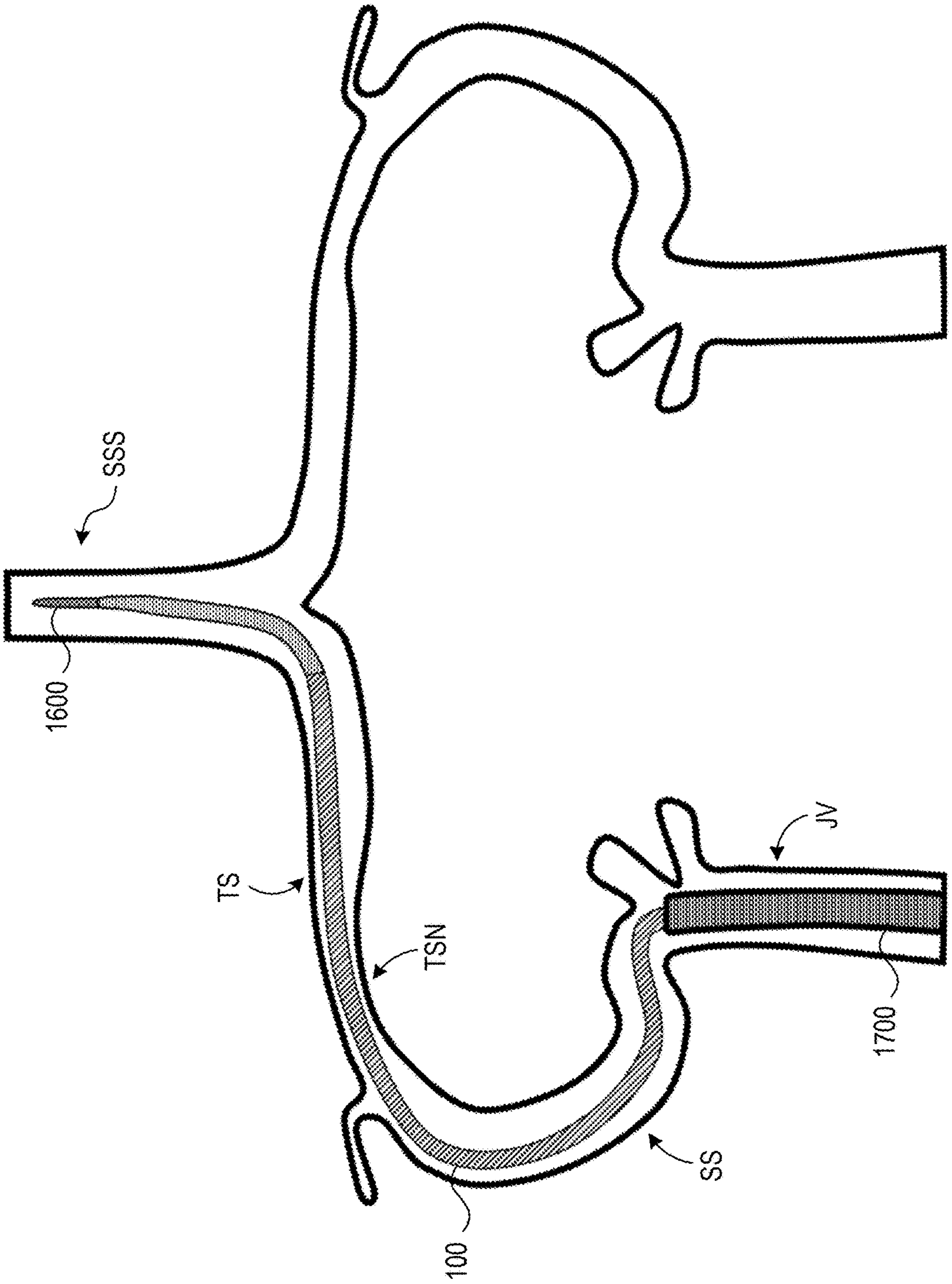
FIG. 10 shows the implant delivery device of FIG. 1 within a portion of a patient's venous sinuses.

FIG. 10 shows the delivery device 100 described herein within a portion of a patient's venous sinuses (VS) and jugular vein (JV). The venous sinuses (VS) can include the transverse sinus (TS), sigmoid sinus (SS), and superior sagittal sinus (SSS). The delivery device 100 can be coupled to a guiding catheter 1700 used to navigate the delivery device 100 to the target location within the venous sinuses (VS). As shown in FIG. 10, the transverse sinus (TS) can narrow (e.g., the transverse sinus narrowing (TSN)), as well as the sigmoid sinus (SS), and superior sagittal sinus (SSS). The narrowing can be due to external pressure and/or can include arachnoid granulations within the venous sinuses (VS). The delivery device 100 can be used to deliver the implants (e.g., the implant 1000) described herein within the venous sinuses (VS). For example, at the transverse sinus (TS) and the sigmoid sinus (SS), the diameters (at round portions of the implants 1000) can be between 3 mm and 12 mm, or at most 3 mm, 6 mm, 8 mm, or 12 mm. Additionally or alternatively, at the transverse sinus (TS) and the sigmoid sinus (SS) the perimeter (at non-round portions of the implants 1000) can be between 9 mm and 38 mm, or at least 9 mm, 19 mm, 25 mm, or 38 mm. In some embodiments, the implants 1000 used to treat the transverse sinus (TS) and the sigmoid sinus (SS) can have a radial force range between 0.001 N/mm and 4 N/mm, or at least 0.001 N/mm, 0.25 N/mm, 0.5 N/mm, 1 N/mm, or 4 N/mm.

Additionally or alternatively, the delivery device 100 can be configured with properties tailored to the requirements of the venous sinuses (VS). For example, the delivery device 100 can be generally more flexible for navigating tortuous sections of the venous sinuses (VS) (i.e., as opposed to straighter sections of anatomy). In some embodiments, the delivery device 100 is maneuverable and/or navigable through a variety of anatomical locations to deliver and deploy one or more implants 1000. In some embodiments, the delivery device 100 is preferably 8 French (F), 6F, or less in diameter for cylindrical implants 1000 or other major cross-sectional dimension for non-cylindrical implants 1000. In some embodiments, the implant 1000 expands to a diameter/cross-sectional dimension that is less than or equal to 5 mm, 10 mm, or 15 mm in an expanded state such that the delivery device 100 with a generally similar cross-sectional dimension is used to deliver the implants 1000. Additionally or alternatively, the delivery device 100 with a generally larger cross-sectional dimension can be used to deliver and deploy one or more generally larger implants (e.g., grafts, valves, etc.).

The delivery device 100 can also be made in various lengths to accommodate one or more access locations, including but not limited to the neck (e.g., jugular, carotid, etc.), arm (e.g., brachial, radial, etc.), and/or groin region (e.g., femoral vein, femoral artery, etc.). In some embodiments, an entirety of the delivery device 100 extends from the access location to the target location. Additionally or alternatively, the delivery device 100 can have a working length that is equivalent to the length of the delivery device 100 that is inserted into the patient and/or other device (e.g., sheath, access catheter, etc.). For example, the delivery devices 100 used at neck access point are typically shorter in overall working length, e.g., between 25 cm and 75 cm in length, or at most 25 cm, 50 cm, or 75 cm. The delivery devices 100 used at groin access points can have a working length between 90 cm and 150 cm, or at least 90 cm, 130 cm, and 150 cm. The working length of the delivery devices 100 used at arm access points can be somewhat intermediate and/or up to similar lengths as the delivery devices 100 used at groin access point, e.g., between 75 cm and 150 cm, or at least 75 cm, 115 cm, or 150 cm. As long as there is sufficient working length, the delivery device 100 can be inserted from any location (e.g., a delivery device that is 150 cm in length can be used with a jugular approach). In some embodiments, the working length of the delivery device 100 is the length of the delivery device 100 omitting the handle 800. Example procedural techniques for delivery of the implants 1000 to the venous sinuses (VS) using the delivery device 100 are described in more detail herein.

FIGS. 11-16 show cross-sectional views of embodiments of inner shafts 120 of a delivery device (e.g., the delivery devices 100 described herein). The inner shafts 120 of FIGS. 11-16 can be identical or generally similar to the inner shafts 120 described elsewhere herein (e.g., the inner shafts 120 of FIG. 2A-2C). Referring to FIGS. 11-16 collectively, the inner shaft 120 can include two or more regions and in some embodiments three or more regions. For example, the inner shaft 120 can include a proximal inner shaft (PIS) region 125, an implant inner shaft (IIS) region 220 distal to the PIS region 125, and a tip region 260 (also referred to herein as distal inner shaft (DIS) region) distal to the IIS region 220. The PIS region 125 can be the portion of the inner shaft 120 proximal to where the implant (e.g., the implants 1000 described herein) is positioned (i.e., closest to a user, physician, healthcare professional, etc.). The IIS region 220 can be the region where the implant (e.g., the implants 1000 described herein) is positioned, as described in more detail with reference to FIGS. 17A-17C. The tip region 260 can be distal to the IIS region 220 and thereby distal to where the implant 1000 is positioned.

The PIS region 125 can include two subregions or components, a proximal inner shaft (PIS) 130 and a mid-inner shaft (MIS) 180. In some embodiments, the PIS 130 and the MIS 180 are combined into a single region and referred to as just the PIS 130 and/or the PIS region 125. The PIS 130 can comprise a combination of a PIS jacket 140, a PIS functional member 150, a functional member 155 (as shown in FIGS. 12-15), a PIS liner 160, or any individual component or combination thereof. The PIS 130 can be made from a PTFE impregnated polyimide with or without a braid or coil, and with or without a PIS jacket 140 and/or PIS liner 160 and/or PIS functional member 150, and/or functional member 155. The PIS functional member 150 and/or functional member 155 can be used to provide column strength and/or resistance to compression to the PIS 130. The PIS functional member 150 can be made from a polymer, metal, polyimide, polyethylene, polyurethanes, polyamides, blends (e.g., Pebax®), stainless steel, NiTi, hypotube, braided, coil(s), thermosets and/or thermoplastics. The functional member 155 can be made from a polymer, metal, polyimide, polyethylene, polyurethanes, polyamides, blends (e.g., Pebax®), stainless steel, NiTi, thermosets, and/or thermoplastics. The functional member 155 can be a hypotube, with or without striations, slots, or fenestrations, braided material, coil(s), or other suitable structures. The PIS liner 160 is preferably a lubricious/low-friction material, and can be for example constructed of or with fluorinated polymers (FEP, PTFE, etc.), high density polyethylene, and the like to facilitate easily tracking over the guide wire 1600. The PIS jacket 140 can be made of a lubricious/low-friction material or can at least include a lubricous/low-friction outer surface (e.g., an outer surface coated with a lubricious material).

The PIS jacket 140 can be lubricious/low-friction with respect to the inner surface of an outer shaft (e.g., the outer shafts 500 described herein), over the range of motion of the outer shaft 500 with respect to the inner shaft 120, allowing the outer shaft 500 to be easily retracted with respect to the inner shaft 120 during implant 1000 deployment. The PIS jacket 140 can comprise polyethylene (e.g., high density), fluorinated polymers or copolymers or impregnated polymers, polyurethanes, nylon, nylon blends, block co-polymers, metal(s), and/or coated materials. The PIS jacket 140 can also be made from a material that is generally similar in structure and configuration to the functional member 155. For example, the PIS jacket 140 can be a hypotube with or without slots or fenestrations, which is then coated to increase lubricity.

The tip region 260, which in some embodiments is primarily used to navigate through more tortuous anatomy (e.g., the sigmoid sinus), can have a generally higher degree of flexibility than the PIS region 125 and/or the IIS region 220. The flexibility of the delivery device 100 that navigates within the venous sinuses (VS) can have a minimum bend radius of at least 3 mm, 5 mm, 7 mm, 10 mm, or 15 mm, or between 3 mm and 15 mm, or between 5 mm and 10 mm, to prevent kinking of the delivery device 100, and thereby reduce the likelihood of compromising movement of the guide wire 1600 and/or deployment of the implant 1000. For example, at an 8 mm radius on a 3-point bend test, the delivery device 100 can have a force between 0.1 N and 3 N, or at most 0.1 N, 0.5 N, 1 N, 2 N, or 3 N. In navigating target areas such as the thorax, the delivery device 100 can have a generally greater minimum bend radius, such as between 1 cm and 20 cm, or at least 1 cm, 5 cm, 10 cm, 15 cm, or 20 cm. As such, it can be desirable to change the flexibility along the length of the inner shaft 120, e.g., by changing materials and/or structures of the functional member 155 and/or PIS functional member 150. Such materials and/or structures can include the coil pitch/diameter/material properties; braid parameters/material properties; slotted, laser cut, fenestrated hypotube; etc., each of which can be selected for the function member 155 and/or PIS functional member 150. Additionally or alternatively, the inner shaft 120 can include or omit the MIS 180, such that the PIS region 125 include only the PIS 130. For example, the PIS 130 can include the PIS functional member 150 made of a NiTi, NiTi alloy, hypotube, stainless steel, braid (e.g., flat or round wire), and/or coil.

The braids can be consistent or vary along the length of the region. For example, a proximal end portion of the PIS functional member 150 can be constructed with a relatively high picks per inch (ppi) braid pattern with a reduced ppi towards the distal end of the PIS functional member 150. For example, the proximal end portion of the PIS functional member 150 can include a ppi between 60 ppi and 70 ppi, whereas the distal end portion of the PIS functional member 150 can include a ppi between 30 ppi and 40 ppi, thus providing the Tip region 260 with more flexibility. Similarly, the PIS functional member 150 can be a coil with or without varying coil spacing and/or wire properties (e.g., diameter) along at least a portion of the length of the functional member 150.

In some embodiments, one or more MISs 180 can be incorporated into the inner shaft 120. the inner shaft 120 can span a length from within a thoracic location and/or the jugular vein (JV) into the sigmoid sinus (SS). Individual ones of the MIS 180 can be made of similar or dissimilar materials than one another, with the necessary changes to increase flexibility. The MIS 180 can include a functional member 200, which can be a relatively more flexible coil (e.g., stainless steel) or construct (polyimide, braid, hypotube, etc.) than the PIS functional member 150. The PIS functional member 150, or the functional member 155, can extend distally into the MIS functional member 200, or can be an extension of the MIS functional member 200 with or without changing properties. The MIS functional member 200, or functional member 155, can extend distally and become an IIS functional member 240 with or without changing properties (e.g., materials, dimensions, etc.). For example, braid pitch, wire dimensions, coil spacing and coil wire diameter, slots or fenestrations, can be adjusted along the length of one or more of the PIS functional members 150, the MIS functional member 200, and/or the IIS functional member 240 to optimize the desired flexibility and resistance to compression of the inner shaft 120. In some embodiments, the PIS functional member 150 is constructed of, for example, polyimide, metal or polymer hypotube, coils, or braids, or combination thereof and the MIS functional member 200 has relatively more flexible coil(s), braid(s), cut/un-cut hypotube, or one or more polymers to reduce the stiffness of the MIS 180 in comparison to the PIS 130. The MIS 180 can also be made from completely different materials than the PIS 130 to provide the desired characteristics. If included, the MIS 180 can have a length between 10 cm and 50 cm, or at least 10 cm, 35 cm, or 50 cm. The PIS liner 160 and MIS liner 210 can be the same or separate components. It can be desirable for the liner(s) to provide a lubricious/low-friction inner surface that can be, for example, constructed of or with fluorinated polymers or copolymers or impregnated polymers (FEP, PTFE, etc.), polyethylene (e.g., high density), polyurethanes, metal(s), coatings, and/or the like to facilitate easily tracking over a guide wire (e.g., the guide wire 1600 described herein).

Figure 14:
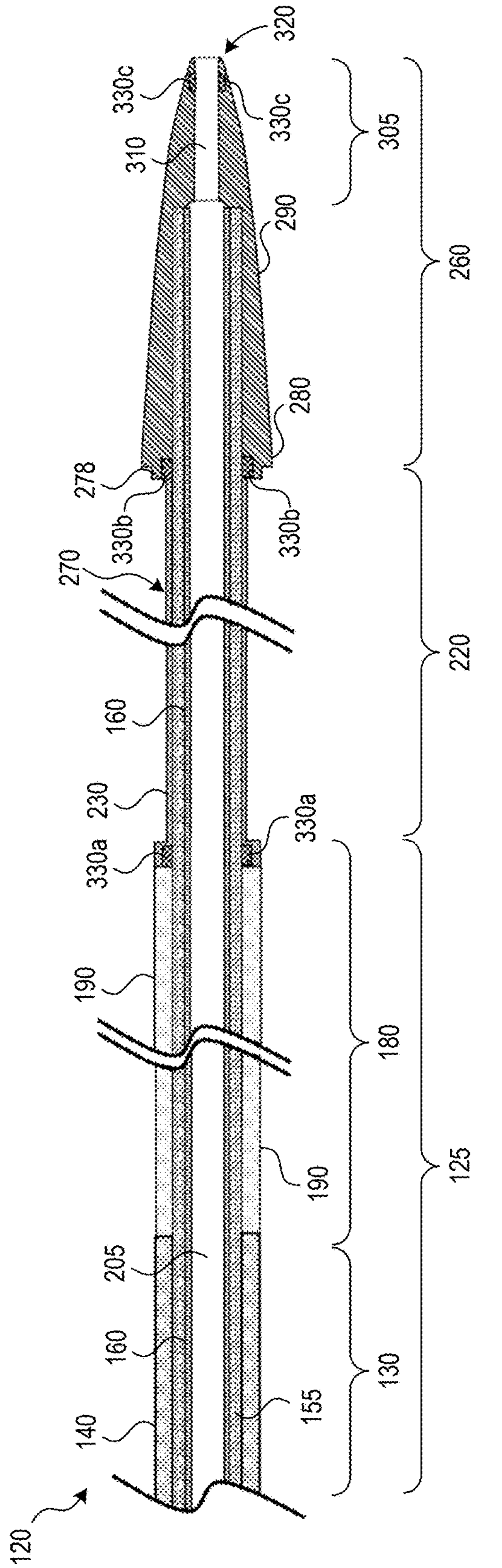

The PIS jacket 140 and/or the MIS jacket 190 can be made of a single material or can be made of multiple materials (e.g., a laminate with polyimide inner and polyethylene outer components). The PIS jacket 140 and/or the MIS jacket 190 can have an outer surface that is lubricious/low friction with respect to the inner surface of the outer shaft 500 over the range of motion of the outer shaft 500 with respect to the inner shaft 120. In some embodiments, the lubricous/low-friction properties are achieved through material selection and/or coatings and can aid in retraction of the outer shaft 500 to deploy the implant 1000. For example, the MIS jacket 190 can be coated and/or made of a polyethylene (e.g., high density), fluorinated polymers or copolymers or impregnated polymers, polyurethanes, nylon and nylon blends, block co-polymers, metal(s). The PIS jacket 140 and/or the MIS jacket 190 can also be made from a material that is generally similar to the functional member 155 and/or the MIS functional member 200. For example, the MIS jacket 190 can be a hypotube, with or without slots or fenestrations, which is in its natural state or coated to increase lubricity. For example, the PIS jacket 140 can be a solid hypotube and which continues and adds fenestrations or slots as it becomes the MIS jacket 190, which can be coated to increase lubricity (as shown in FIG. 14). Materials can be, for example, stainless steel, NiTi, NiTi alloys, and/or polymers.

The IIS region 220 is located along the inner shaft 120 at least partially where the implant (e.g., the implant 1000 described herein) is located with respect to the inner shaft 120. The IIS region 220 can have a lower profile than at least a portion of the inner shaft 120 that is proximal to the IIS region (e.g., the PIS region 125) to maintain the implant 1000. It can be desirable to have at least a portion of the IIS region 220 loaded with the implant 1000 and the outer shaft (e.g., the outer shafts 500 described herein) have a similar flexibility to at least a portion of the delivery device 100 adjacent the IIS region 220. This enables the delivery device 100 with implant 1000 to smoothly track over the guide wire (e.g., the guide wire 1600 described herein) without abrupt transitions and/or potential kink points, reducing potential trauma to the vasculature and improving navigability. The IIS region 220 can be constructed with one or more of, but not limited to, an IIS jacket 230, an IIS functional member 240, a functional member 155, and an IIS liner 250. The IIS region 220 cross-section can be generally round for delivering implants 1000 that are round when collapsed. Additionally or alternatively, the IIS region 220 can be non-round for implants 1000 that are non-round when collapsed.

Similar to the functional members described herein, the IIS functional member 240 and/or the functional member 155 can provide resistance to compression while allowing the necessary flexibility to navigate through tortuous anatomy. The IIS functional member 240 can be comprised of one or more tubular members, including a fenestrated or open tubular member(s), solid tubular member(s), coil(s), braid(s) or a combination thereof. The IIS functional member 240 can be a continuation of the PIS functional member 150 and/or the MIS functional member 200. In these cases, the material, hypotube cut pattern, braid, and/or coil properties, including the properties (e.g., dimensions, heat treat, tensile strength, etc.) of the wire(s) or materials, can be changed to provide the desired functional characteristics. Examples for a braid can include changing the braid pitch to increase flexibility, and/or for a coil reducing the wire diameter, changing material properties and/or changing the coil spacing. These alterations can be used to modify the functional properties, e.g., flexibility and/or compression resistance of the IIS region 220. The IIS liner 250 can be a continuation of the PIS liner 160 and/or MIS liner 210 or can be a separate component or components. The IIS liner 250 preferably has a lubricious/low-friction inner surface and can be for example made from polyethylene (e.g., high density), fluorinated polymers or copolymers or impregnated polymers, polyurethanes, metal(s), and/or coated to facilitate tracking over the guide wire.

Similarly, the IIS jacket 230 can be coated and/or made from a lubricious/low-friction material to enable easy deployment of the implant 1000. In some embodiments, the IIS jacket 230 can be made of a material that is not relatively low friction, such that the IIS jacket 230 helps to maintain the implant 1000 in position (e.g., keep the implant 1000 from longitudinally moving, shortening, or compressing/bunching) during introduction and advancement of the delivery device 100 with implant 1000 into and through the anatomy to the target deployment location as well as during deployment of the implant 1000. Additionally or alternatively, the surface of the IIS jacket 230 can have features, for example, one or more or of a combination of bumps, ridges, dimples, coatings, texturing, surface treatments, etc. to facilitate maintaining the position/shape of the implant 1000 with respect to the delivery device 100 prior to and/or during implant 1000 deployment.

Figure 16:
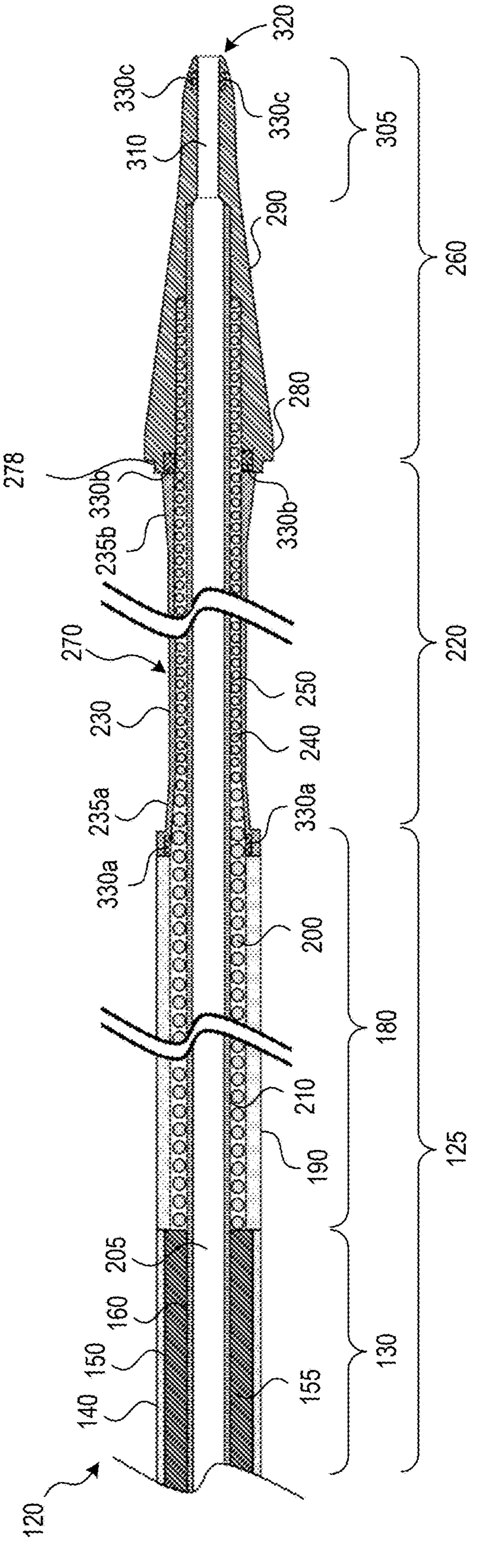

The IIS jacket 230 can include one or more IIS tapers **235*a* and 235*b* (collectively referred to as "IIS tapers 235") (as shown in FIG. 16), such as a region with a progressively smaller cross-sectional dimension at one end and a progressively larger cross-sectional dimension at another end. The IIS taper 235 can be used to assist in holding the implant in position, and/or to adjust flexibility of that portion of the delivery device 100, and/or to fit changes in the constrained diameter of the implant 1000. The IIS taper 235 can be located at one or more locations along the inner shaft 120. The IIS taper 235 can be, for example, located at the distal region of the IIS region 220**, where the implant can be more flexible, and/or have different dimensions than more proximal regions of the implant.

The IIS region 220 can be at least in part radiopaque and/or have one or more radiopaque markers 330 to assist in identifying the location of the implant 1000 and/or features of the implant 1000, such as implant 1000 regions, e.g., one or more radiopaque markers 330 to identify the location of where the first zone 1050 meets the second zone 1100. The radiopaque marker **330*a* can be located adjacent the proximal (with respect to the inner shaft 120) end of the implant 1000. In addition, the radiopaque marker 330*b* can be adjacent the distal (with respect to the inner shaft 120) end of the implant 1000. The radiopaque markers 330*a*, 330*b* can be positioned adjacent or within the IIS region 220. Additionally or alternatively, tip region 260 can include a radiopaque marker 330*c* that can indicate where the distal end of the delivery device 100 is positioned. In some embodiments, one or more components of the tip region 260 (e.g., a distal tip end region 320) are partially or entirely made of radiopaque material to assist with positioning and/or navigation. The IIS functional member 240 or a portion thereof can also be radiopaque, such as made with at least in part a radiopaque material, for example, tungsten, platinum, tantalum, iridium, and their alloys and/or using a polymer (e.g., polyethylene, polyurethane, Pebax, nylon, blends) loaded with a radiopaque material (e.g., tungsten, $BaSO_4$). Examples include but are not limited to a radiopaque coil, a hypotube with or without fenestrations or cuts, and/or a braid. Additionally or in place of, a radiopaque wire along a length of or wound within the IIS functional member 240 can provide radiopacity. The IIS jacket 230 can be radiopaque, for example, using a polymer loaded with a radiopaque material as previously described for the IIS functional member 240**.

The tip region 260 can include a distal tip end region 320 at the distal most end ("distal terminus") of the inner shaft 120 and the delivery device 100. The tip region 260 can be flexible and configured to enable atraumatic and easy navigation, particularly useful with tortuous anatomy, as well as provide a transition into more proximal regions of the inner shaft 120 and/or the outer shaft 500 (e.g., between the IIS region 220 and the outer shaft distal end region 620). In some embodiments, the tip region 260 includes a distal tip 280. The distal tip 280 can include an outer profile or diameter similar to that of the distal end of the outer shaft 500. Additionally or alternatively, the distal tip 280 can include a distal tip taper 290 to make the tip region more atraumatic. The tip region 260 and/or the distal tip 280 can include a proximal outer profile or diameter that is generally similar or identical to that of the distal end of the outer shaft 500 to ensure there is no opportunity for the outer shaft 500 to have an exposed leading edge when introducing and navigating the delivery device 100 with implant 1000 into and through the anatomy. In some embodiments, the distal tip taper 290 includes a cross-sectional dimension that decreases in the distal direction towards the distal tip end region 320. The distal tip taper 290 serves as a transition, predominantly in flexibility and diameter, to more proximal regions of the inner shaft 120. The length of the tip region 260 can be between 0.5 cm and 8 cm, or at least 0.5, 4 cm, or 8 cm more.

In some embodiments, the tip region 260 contains a distal tip extended region 305 which can be between 0.5 cm to 3 cm in length, or at least 0.5 cm, 1.75 cm, and 3 cm in length. The distal tip extended region 305 can be of a relatively constant profile for a portion of its length or diameter or have some degree of taper or steps as well as can have a change in flexibility along the length. The distal tip extended region 305 can aid in the trackability of the delivery device 100 with implant 1000 by providing for the tip region 260 to navigate through tortuous sections of the vasculature before the IIS region 220 of the delivery device 100 is required to navigate through that section of the vasculature. In some embodiments, the distal tip end region 320 is the leading end of the delivery device 100. The distal tip end region 320 can be radiused and/or tapered and/or beveled preferably without sharp edges and readily exposed to the vasculature to provide an atraumatic leading end when advancing the delivery device 100 with implant 1000 through the vasculature.

In some embodiments, one or more of the liners, functional members, and/or jackets can extend up to, into, and/or through the tip region 260. As shown in FIGS. 12-15, the IIS functional member 240 and IIS liner 250 are extended partially or fully into the tip region 260. This can be done to optimize the flexibility, attachment surface area, and improve the transition along the region of the delivery device 100 with implant 1000. In some embodiments, the tip region 260 has its own functional member, different from, similar to, or identical to that in other parts of the delivery device 100.

Figure 15:
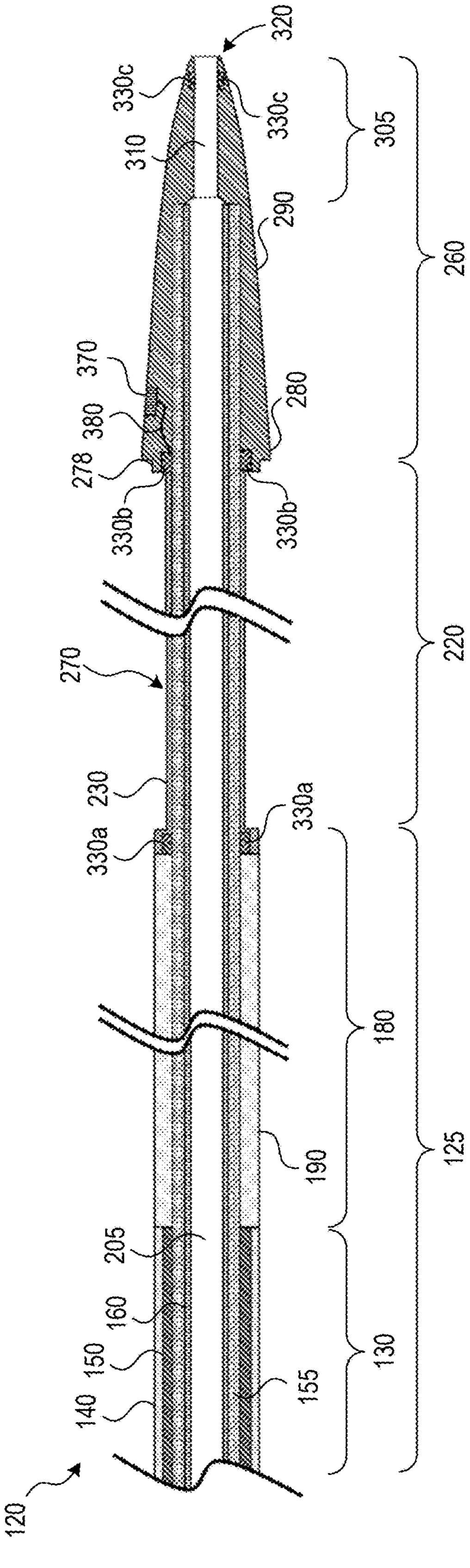

As shown in FIG. 15, the tip region 260 can include one or more sensors 370. The sensors 370 can be coupled to a sensor lead 380 which couples the delivery device 100 to one or more external equipment. The sensor(s) 370 can include but are not limited to pressure, flow, and/or temperature measurement. By having the sensor(s) 370, data can be collected without having to change out the delivery device 100 for another catheter with measuring capabilities, which in turn reduces the procedure time as well as saving the expense of another catheter to do the measurements and increases safety by decreasing the amount of devices (e.g., surgical tools, etc.) placed within the vasculature. For example, the sensor(s) 370 can be used to measure pre-deployment pressures and flows across the narrowing, deploying the implant 1000 throughout delivery and/or post-deployment to assess an improvement and/or change and providing an indication of procedural success.

Figure 11:
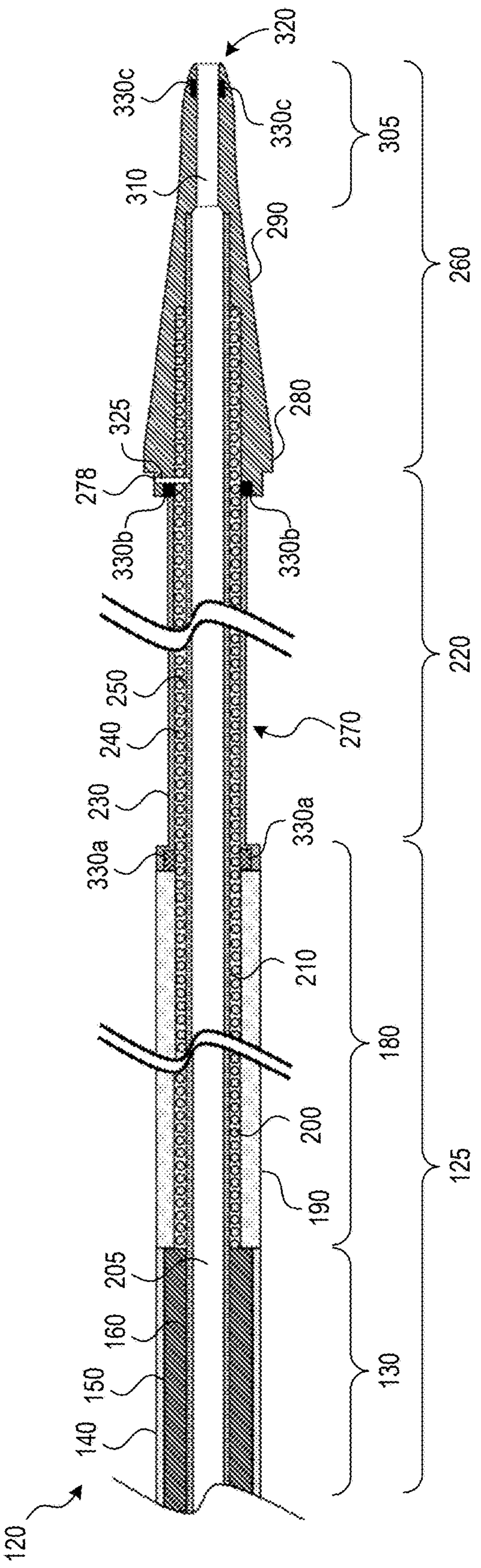
FIGS. 11-16 show cross-sectional views of inner shafts of an implant delivery device, in accordance with embodiments of the present technology.
Figure 12:
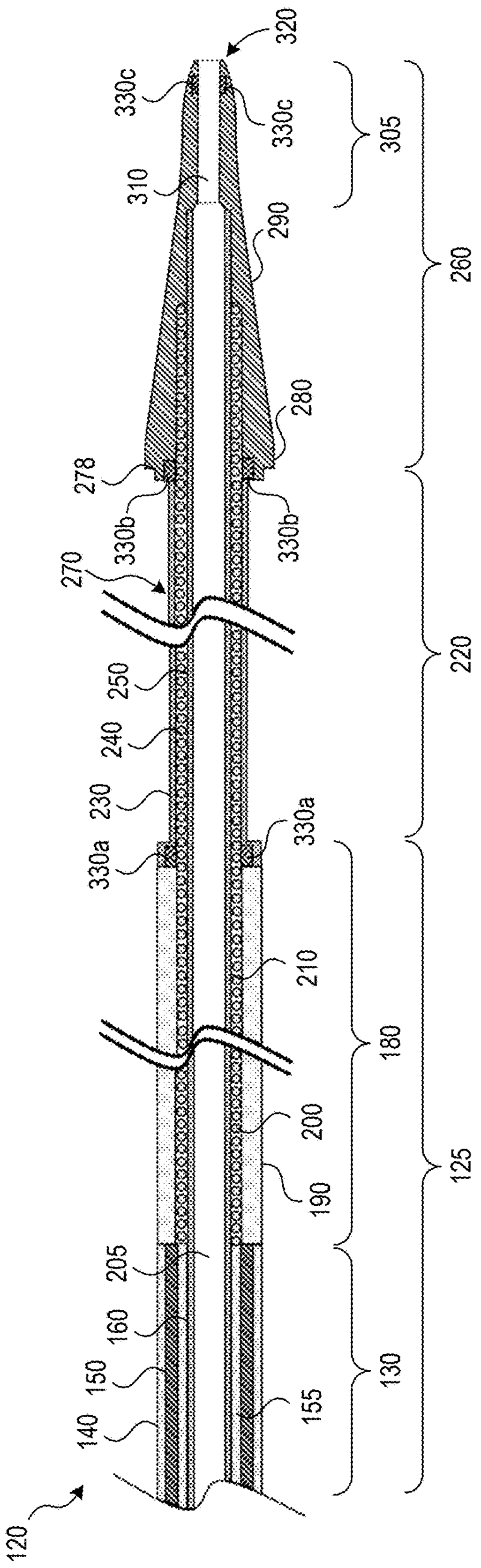
Figure 13:
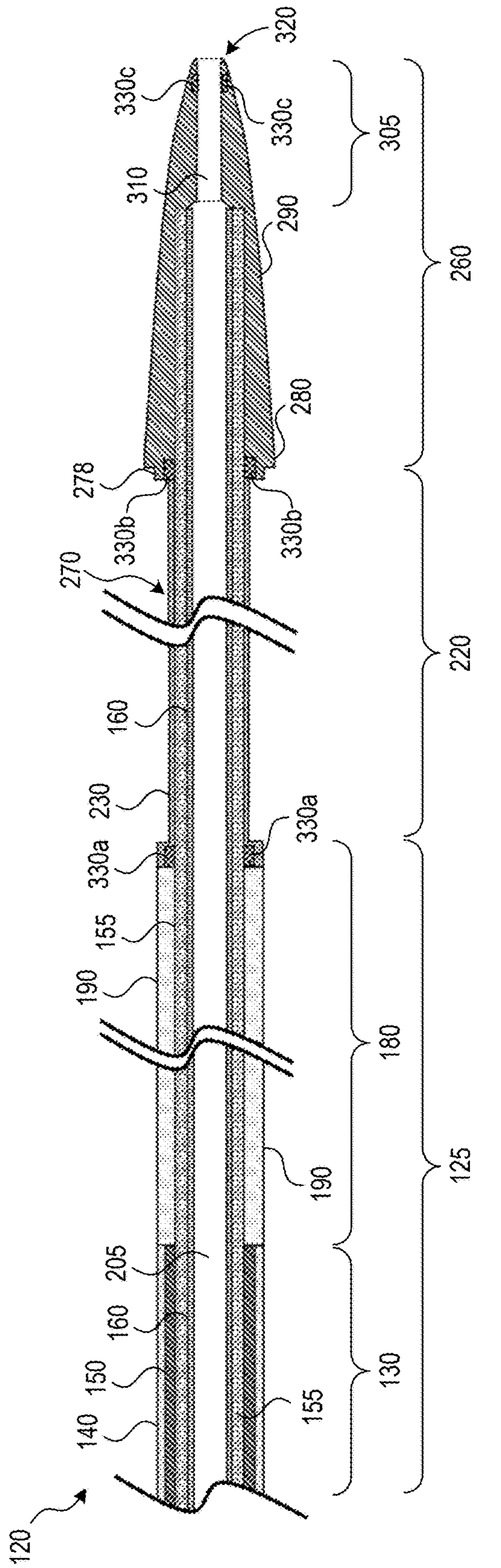

In some embodiments, the liner, functional member, and/or jacket can be combined in any or all the PIS region 125, the IIS region 220, or the tip region 260. For example, the PIS functional member 150 can be a braid and/or coil partially or fully imbedded in a polymer, with the polymer effectively serving as the PIS jacket 140 (as shown in FIGS. 11 and 12) and/or PIS liner 160.

In some embodiments, the inner shaft 120 outer surfaces can be coated or layered to increase or decrease friction/movement with respect to the other surfaces of the delivery device 100 and/or implant 1000 surfaces and/or with respect to the guide wire 1600, the target vasculature, and/or other devices used during the procedure, such as guiding catheters, introducers, and/or the like. Surface coatings can be but are not limited to hydrophilic, hydrophobic, fluoropolymers, silicone, polymer, etc. as well as using lubricious materials for an outer layer or jacket as described herein. In some embodiments, the inner shaft 120 provides a substantial amount of the overall resistance to compression of the delivery device 100. By having the inner shaft 120 provide resistance to compression, the outer shaft 500 can provide a reduced level of compression resistance, potentially allowing the outer shaft 500 to be relatively thin walled and configured more for resistance to elongation, as well as reducing the longitudinal compression resistance required by the implant 1000 within the delivery device 100.

Figure 17A:
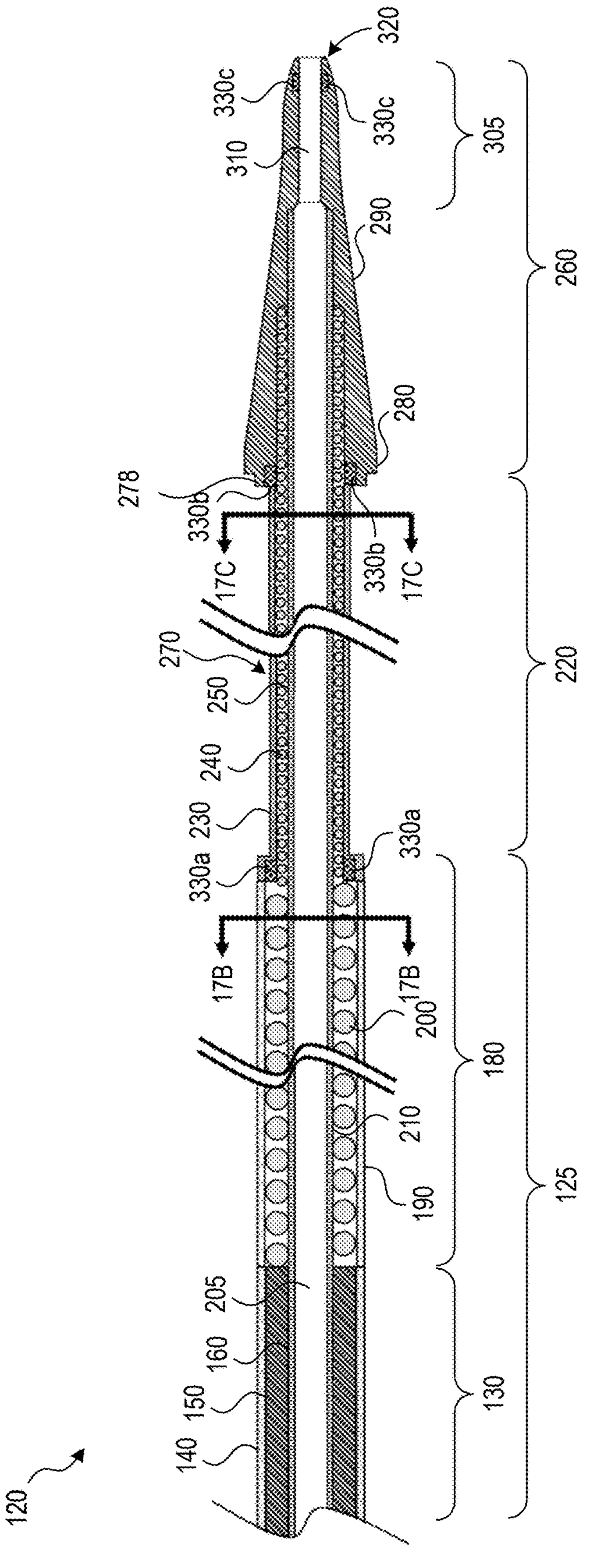
FIGS. 17A-17C show an inner shaft of an implant delivery device, in accordance with embodiments of the present technology.
Figure 17C:
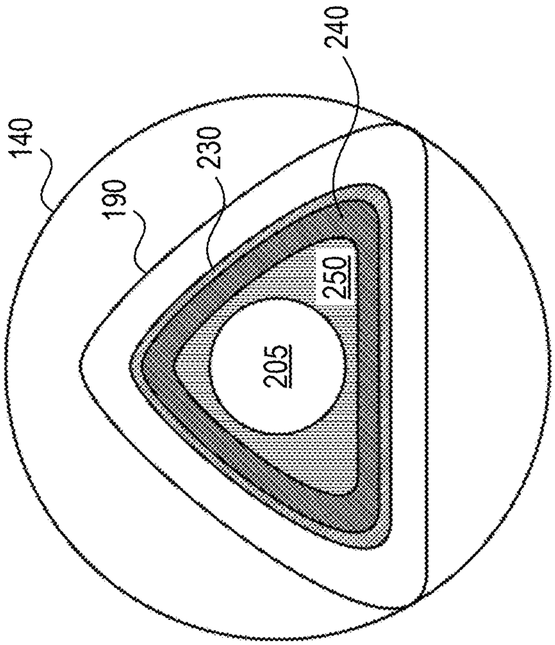
Figure 17B:
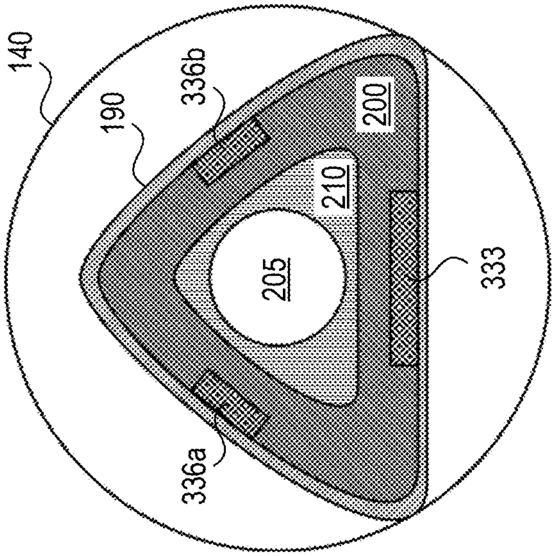

FIGS. 17A-17C show an inner shaft 120 of a delivery device (e.g., the delivery device 100 described herein). As shown in FIGS. 17A-17C, the inner shaft 120 can be identical or generally similar to the inner shafts 120 described in FIGS. 11-16. As shown in FIGS. 17B and 17C, the IIS region 220 can be triangular in cross-section to mimic the shape of the collapsed implant 1000 that is triangular in cross-section. If the implant 1000 has more than one cross-sectional profile (e.g., round and triangular, triangular and rectangular, etc.) the IIS region 220 can have two (or more) similar cross sections. In addition, if the IOS region (e.g., the IOS region 600 described herein) has a non-round inner profile, the length of the inner shaft 120 proximally adjacent the IIS region 220 can have a similar or longer length than the IIS region 220 and/or can be of a similar non-round shape to enable the IOS region 600 to retract over the inner shaft 120.

Figure 6B:
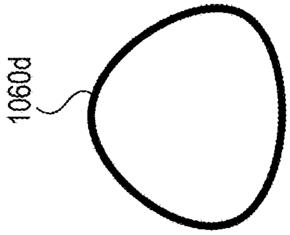
Figure 6C:
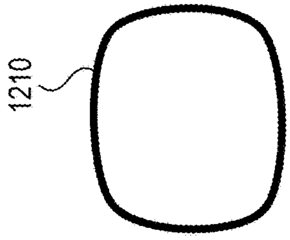

In some embodiments, the radiopaque markers 330 of the inner shaft 120 are used to rotationally orient the delivery device 100 with respect to an implant that is non-round when collapsed (e.g., the implant 1000 of FIGS. 6A-6C). As shown in FIG. 17B, the inner shaft 120 can include a radiopaque marker 333 on a lower portion of the inner shaft 120 and radiopaque markers 336*a* and 336*b* (collectively referred to as "radiopaque markers 336") on one or more side portions of the inner shaft. For example, the radiopaque marker 333 can be positioned to identify a longer side of the implant 1000 under fluoroscopy, and the radiopaque marker (s) 336 can be positioned to identify one or more shorter sides of the implant 1000. If all sides of the implant 1000 are the same length, one or more of the radiopaque markers 330, 333, 336 in the delivery device 100 can be used to provide visualization as to the rotational orientation of a flat/flatter side of the implant 1000. In some embodiments, the radiopaque markers 333 and 336 are the radiopaque markers 330 of FIG. 17A and are positioned on either side of the IIS region 220, ensuring the implant 1000 is properly oriented when deployed in the vessel. Although not explicitly shown in FIGS. 17A-17C, one or more radiopaque markers can also be similarly incorporated into the outer shafts 500 described herein. In some embodiments, typically where the implant 1000 is non-round and there is a desired orientation within the vasculature, the delivery device 100 can include certain aspects to provide for self-orientation within the target location, to enable the implant 1000 to be deployed with a desired rotational orientation with or without having to purposefully rotate the delivery device 100 when at the target location for deployment.

Figure 18A:
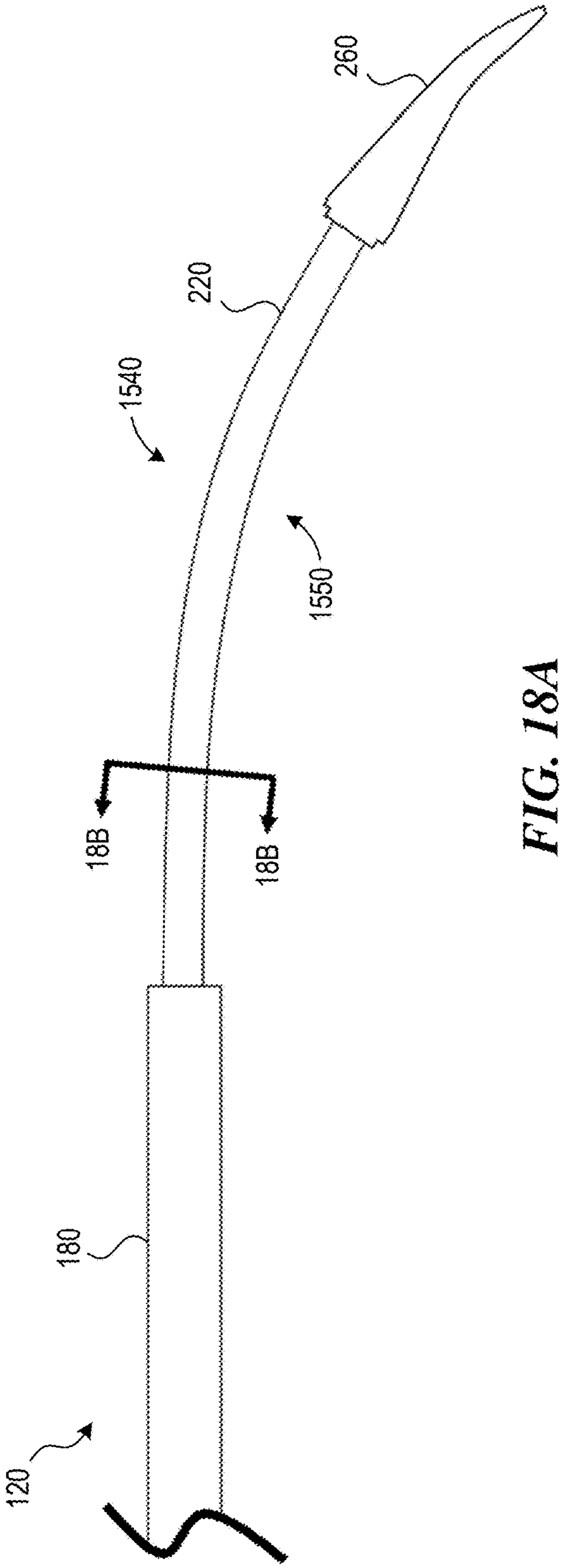
FIGS. 18A and 18B show an inner shaft with biasing features, in accordance with embodiments of the present technology.
Figure 18B:
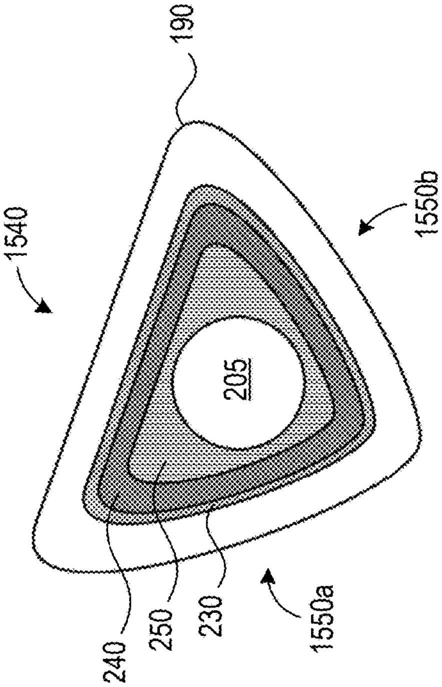

FIGS. 18A and 18B show the inner shaft 120 with biasing features. As shown in FIG. 18A, some portion of one or more of the MIS 180, the IIS region 220, the distal tip 280, and/or any section(s) of the outer shaft (e.g., the outer shaft 500 described herein) can be biased to curve the delivery device (e.g., the delivery device 100 described herein) with a specific rotational orientation to position a desired side of the implant 1000 in a specific orientation. For example, and as shown in FIGS. 18A and 18B the IIS region 220 can include a skull side 1540 outside of the curve to accommodate placing a generally longer side of the implant 1000 on the outside of the curve and up against the skull when in the transverse sinus (TS) and/or sigmoid sinus (SS). Additionally of alternatively, the IIS region 220 can include brain sides 1550*a* and 1550*b* (collectively referred to as "brain sides 1550") that are generally shorter sides relative to the skull side 1540 and positioned towards the brain. In some embodiments, the biasing feature is implemented into to an eccentric tubular member. Additionally or alternatively, the biasing feature can be part of the outer shaft 500 and/or inner shaft 120. For example, the outer shaft 500 or inner shaft 120 can include larger wall thicknesses on either one or sides of the shafts. In some embodiments, the biasing feature is one or more elements, such as metal strips positioned on or within the outer shaft 500 or inner shaft 120 made of a pre-curved NiTi or stainless steel with or without a radiopaque coating (e.g., the radiopaque marker 333 of the delivery device 100 of FIG. 11). Additionally or alternatively, one or more of the outer shaft 500 or the inner shaft 120 can be configured with a curve, such as by heat shaping or molding, etc.

FIGS. 19-23 show cross-sectional views of outer shafts 500 of a delivery device (e.g., the delivery devices 100 described herein). The outer shafts 500 of FIGS. 19-23 can include identical or generally similar features to the outer shafts 500 described herein. Referring to FIGS. 19-23 collectively, the outer shaft 500 can include one or more regions, or in some embodiments two or more regions. For example, the outer shaft 500 can include a proximal outer shaft (POS) region 510 proximal to where the implant (e.g., the implant 1000 described herein) is positioned in the delivery device 100. Additionally, the outer shaft 500 can include an implant outer shaft (IOS) region 600 where the implant 1000 is maintained within the delivery device. In some embodiments, there is a distal region (not illustrated) that is distal to the IOS region 600. For example, the distal region can be an extension of a recess in the inner shaft (e.g., an extension of the recess 270 of the inner shaft 120 of FIGS. 11-18B).

The POS region 510 can be made from a single material or multiple materials, such as a combination of a POS jacket 520 and a POS liner 540. As shown in FIGS. 19-23, the POS jacket 520 can be generally thicker than the POS liner 540. Additionally or alternatively, the POS jacket 520 can be generally the same or thinner thickness than the POS liner 540. The POS region 510 can also include a POS functional member 550. The POS functional member 550 can include identical or generally similar features to the functional members described herein for the inner shaft (e.g., the functional members 200, 240 of the inner shafts 120 of FIGS. 11-17C). The POS region 510 and the IOS region 600 can have variable diameters, as described in more detail with reference to FIG. 2A. Additionally or alternatively, and as shown in FIG. 20, the outer shaft 500 can have a relatively constant inside diameter throughout the entire length of the outer shaft 500.

The POS region 510 can comprise a polymer tube, with or without variable stiffness (e.g., changing polymers), and functionality along an entirety its length. In some embodiments, the POS region 510 includes a singular wall thickness or multiple wall thicknesses along an entirety of its length. or wall thickness. In some embodiments, it is preferrable that the POS region 510 be constructed to sufficiently minimize elongation when retracting the POS region 510 with respect to the inner shaft 120 to deploy the implant 1000. In this regard, one or more relatively high tensile strength materials or configurations can be used in the construction of the POS region 510, such as polyethylene, polyurethanes, polyimide, nylon, nylon blends, block co-polymers, metals, fiber(s), and/or braids.

Figure 19:
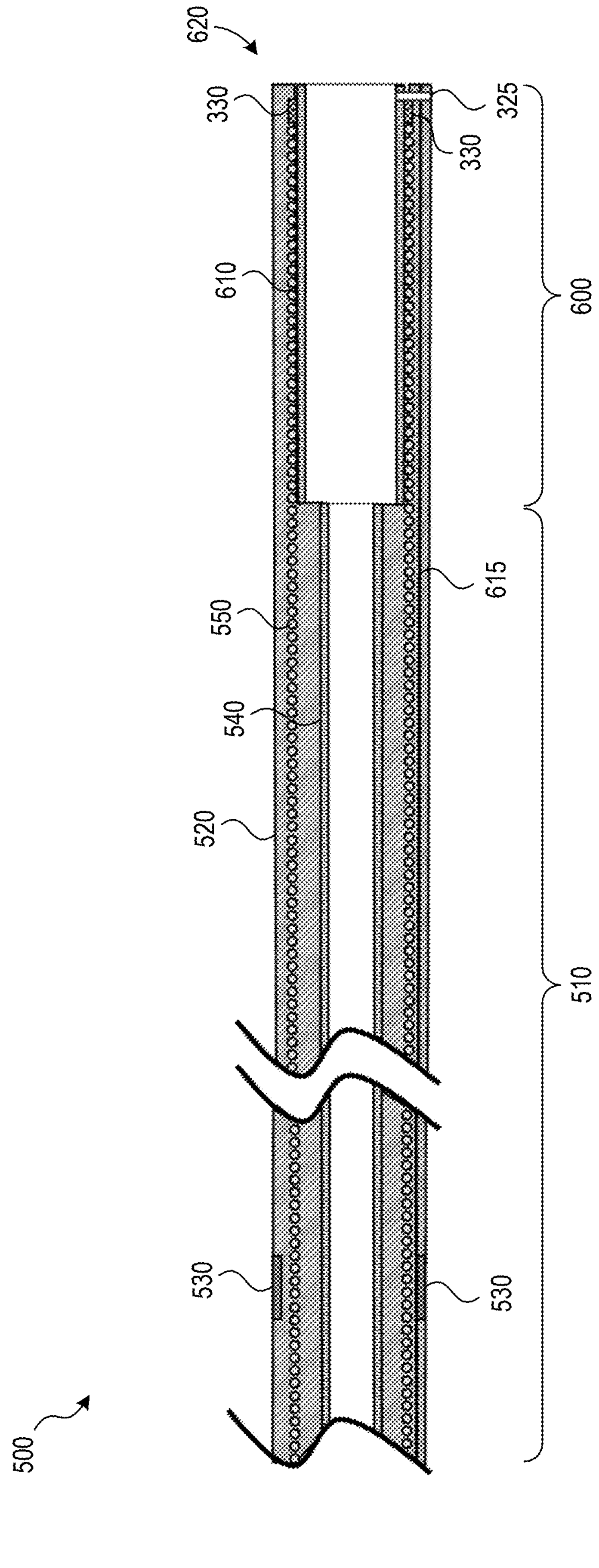
FIGS. 19-23 show cross-sectional views of outer shafts of an implant delivery device, in accordance with embodiments of the present technology.
Figure 20:
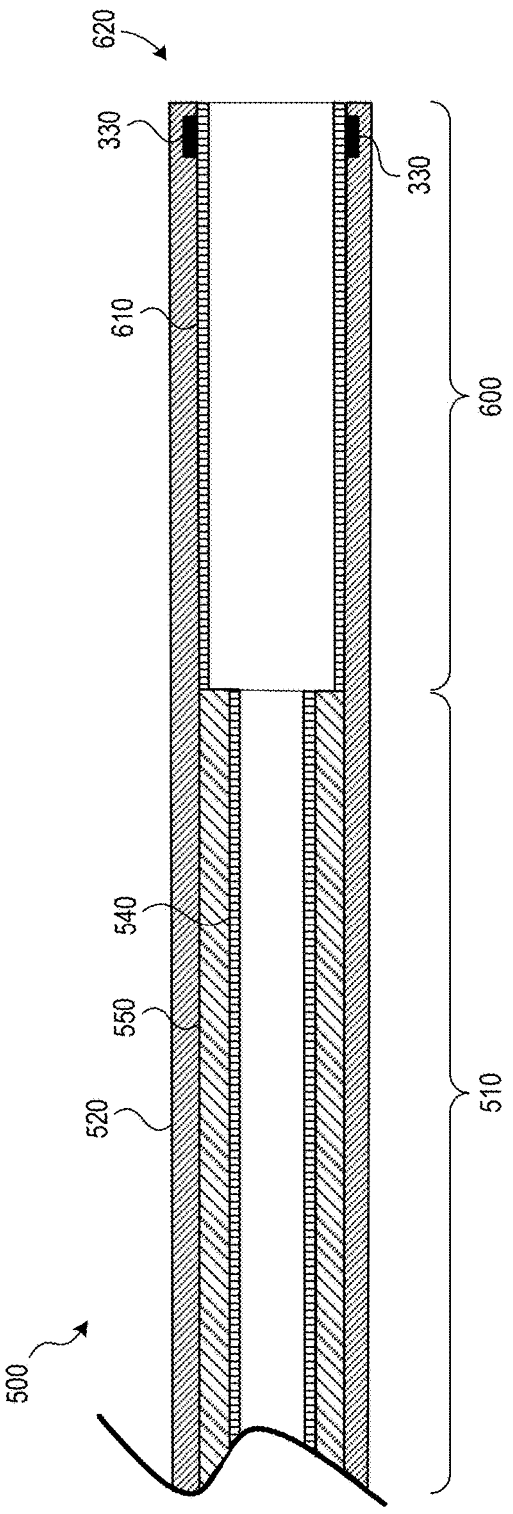
Figure 21:
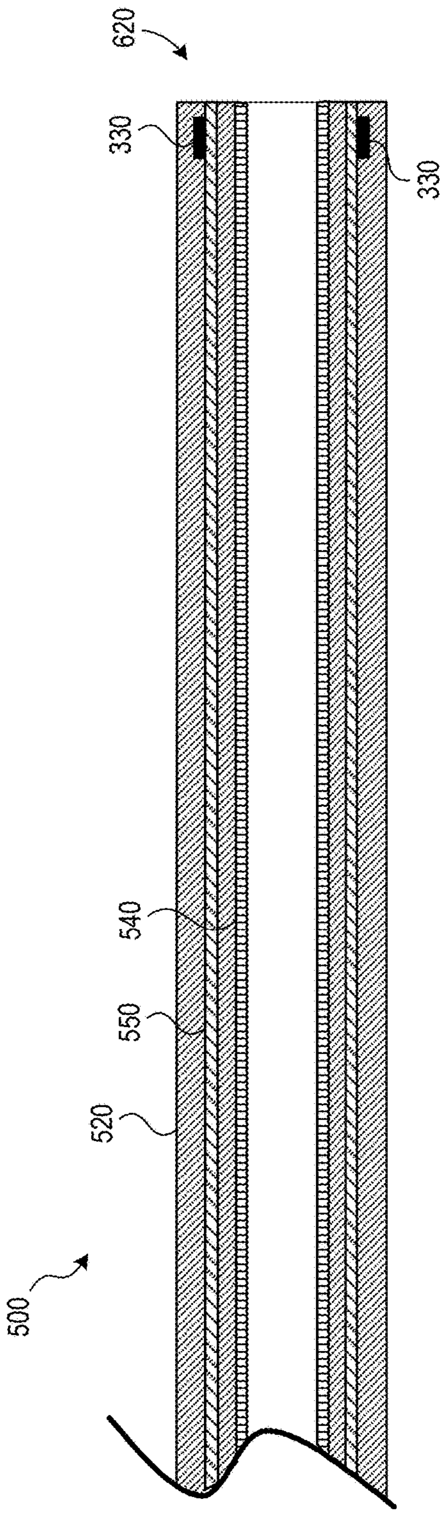

As shown in FIG. 19, the POS region 510 can include a POS marker 530. The POS marker 530 can be a visual marker that is for example, a different color than the POS jacket 520 and/or radiopaque. The POS marker 530 can be positioned a specific distance from the IOS region 600 and/or the tip region 260 of the inner shafts 120 described herein. In some embodiments, the POS marker 530 can be positioned a distance between 75 cm and 115 cm, or at least 75 cm, 85 cm, 95 cm, or 115 cm from the distal tip of the delivery device 100 (e.g., the distal tip end region 320 of FIGS. 11-16). For example, the POS marker 530 can be used to position the distal tip end region 320 at a distal end of a guiding catheter (i.e., the guiding catheter 1700 of FIG. 10). Specific distances can also be used to include the length of any fittings or adapters that can be incorporated, such as at the proximal end of a guiding catheter 1700. In some embodiments, multiple of the POS markers 530 can be used, such as at a distance between 90 cm and 135 cm, or at least 90 cm, 112 cm, or 135 cm from the distal tip end region 320 to serve as indicate more than one position within the guiding catheter 1700.

Figure 22:
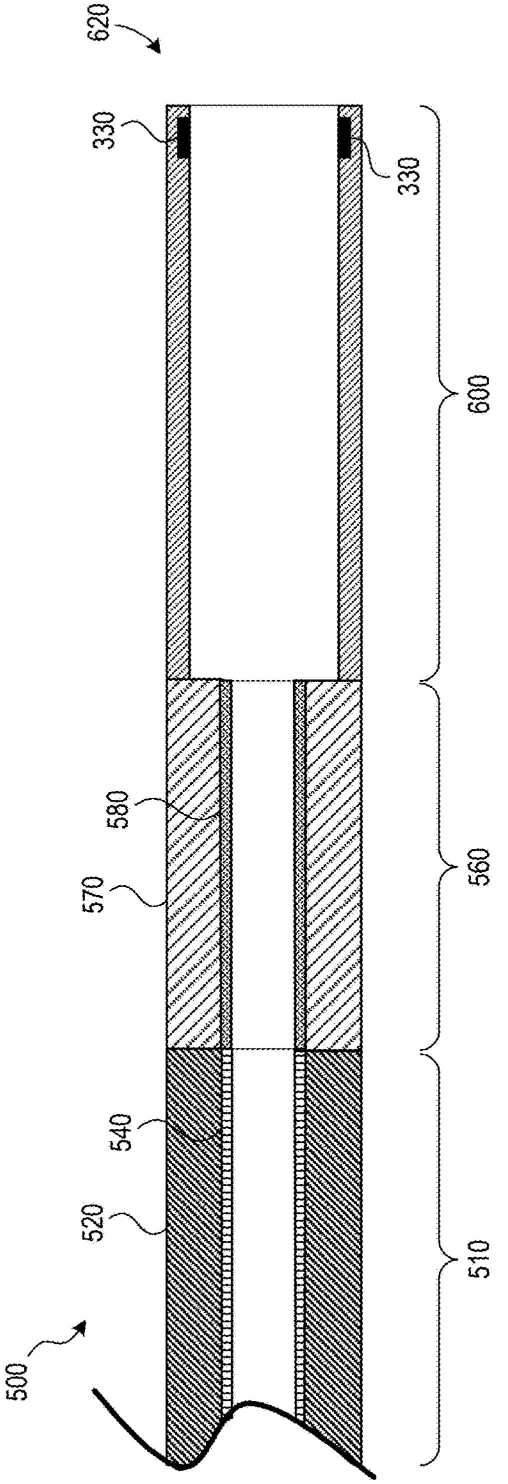
Figure 23:
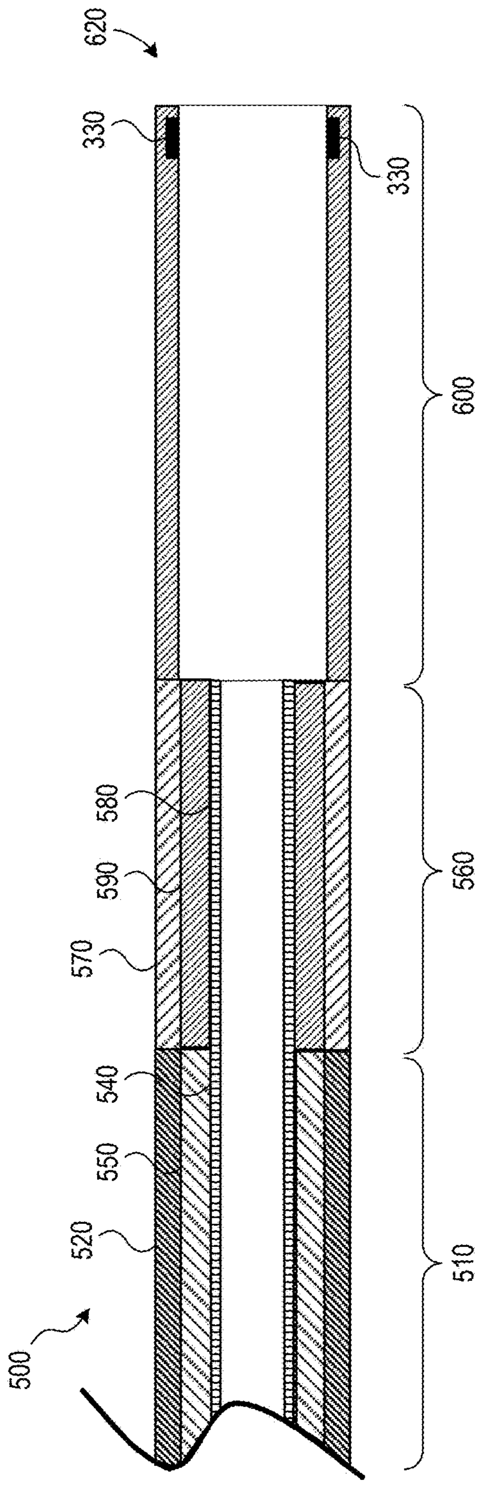

In some embodiments, the POS region 510 has more than one region. As shown in FIGS. 22 and 23, the POS region

510 can include a mid-outer shaft (MOS) region 560. The MOS region 560 can be configured to extend through more tortuous vasculature than the POS region 510, such as from within the jugular vein (JV) into the sigmoid sinus (SS) and can also extend into the transverse sinus (TS), superior sagittal sinus (SSS), contralateral transverse sinus, and/or contralateral sigmoid sinus, as described in more detail with reference to FIG. 10. The MOS region 560 can be more flexible than at least a portion of the POS region 510. The MOS region 560 can include a MOS jacket 570 that can be an extension of the POS jacket 520 or a separate component. In some embodiments, the entirety of the outer shaft jacket of the outer shaft 500 can be a single component. The MOS region 560 can also include an MOS functional member 590 similar to the functional members described herein for the inner shaft 120. The MOS region 560 can include a MOS liner 580. The MOS liner 580 is preferably a lubricious and/or a low-friction material with respect to the inner shaft 120 outer surface and can be for example constructed of or with fluorinated polymers (FEP, PTFE, etc.), high density polyethylene, and the like. The POS liner 540 and MOS liner 580 can be configured as the same or different components.

The IOS region 600, where the implant 1000 is positioned, can be an extension of the POS region 510 or the MOS region 560, or it can be constructed with a combination of different diameters, wall thicknesses, flexibility, tensile strength, coatings, and/or liners. In some embodiments, the IOS region 600, as well as the outer shaft 500, be constructed to sufficiently minimize elongation when retracting the outer shaft 500 with respect to the inner shaft 120 to deploy the implant 1000. The IOS region 600 can include an IOS liner 610, which can comprise a material that allows for retraction of the outer shaft 500 without causing undue foreshortening, sticking, or jumping of the implant 1000 during deployment, as well as during introduction and advancement of the delivery device 100 with implant 1000 into and through the anatomy to the target deployment location. The IOS liner 610 can be a lubricious and/or a low-friction material with respect to the implant 1000 and can be made from high density materials (e.g., polyethylene, fluorinated polymers, copolymers, impregnated polymers, polyurethanes, metal(s)) Additionally or alternatively, the IOS liner 610 can be a coating that increases lubricity. The IOS liner 610, POS liner 540, and MOS liner 580 can be the same or different components.

The outer shaft distal end region 620 can optionally extend beyond the location of the implant. In some embodiments, the outer shaft distal end region 620 extends beyond the implant and is configured to fit into the recess 270, allowing the outer shaft 500 to endure relative movement with respect to the inner shaft 120 without exposing the implant during introduction and/or advancement of the delivery device 100 into the target anatomy. Additionally or alternatively, the outer shaft distal end region 620 can serve as a transition area to optimize flexibility in distal end region the delivery device 100.

In some embodiments, one or more regions of the outer shaft 500 have more than one functional member or a functional member that is made of one or more elements. For example, the outer shaft 500 can have a POS functional member 550 that includes a braid and a coil over the braid. Likewise, the MOS functional member 590 and the IOS functional member 612 can include a braid and a coil over the braid. As previously described, one or more of the functional members 550, 590, 612 can extend and/or be incorporated into one or more the regions 510, 560, and 600 of the outer shafts 500. For example, the POS functional member(s) 550 can extend into the MOS region 560 to form the MOS functional member(s) 590 and/or into the IOS region 600 to form the IOS functional member(s) 612.

In some embodiments, at least a portion of the outer shaft 500 is not round. For example, the implant 1000 can be non-round (e.g., triangular) in the collapsed state, and the inside profile of the IOS region 600 can mimic the shape of the implant 1000. Additionally or alternatively, if the implant 1000 is triangular in profile in the collapsed state (e.g., such as the implant 1000 of FIG. 18A), the inside profile of the IOS region 600 can be triangular in shape to conform to the shape of the implant 1000. The external profile of the IOS region 600 can also be triangular, round, or a different shape. Provided the inner profile of the IOS region 600 is not round, a portion of the inner shaft 120 proximal to the location of the implant 1000 can be similarly shaped or smaller in cross section to allow the IOS region 600 to retract over that portion of the inner shaft 120, as described in more detail with reference to FIG. 8B.

As shown in FIG. 19, the outer shaft 500 can include a vent 325 extending from the lumen or an annulus between the inner shaft 120 and outer shaft 500 to an area external to the outer shaft 500, e.g., to enable air flow or other fluids to be removed or flushed out from the lumen. In some embodiments, and as shown in FIG. 11, the inner shaft 120 can include the vent 325 as well. The vents 325 can be generally aligned such that air can flow out of the annulus between the outer shaft 500 and the inner shaft 120 during preparation of the delivery device (i.e., flushing the delivery device with saline).

In some embodiments, the outer shaft 500 can include one or more of the radiopaque markers 330 described herein to indicate certain locations on the outer shaft 500. In some embodiments, the outer shaft 500 includes one of the radiopaque markers 330 at a distal most end of the outer shaft distal end region 620 such that a user can fluoroscopically visualize the distal most end of the outer shaft distal end region 620 with respect to the implant 1000 during positioning and/or deployment of the implant 1000.

In some embodiments, a portion or an entirety of one or more of the regions 510, 560, 600 of the outer shaft 500 are radiopaque. For example, the regions 510, 560, 600 can be made of a radiopaque material or polymer (e.g., polyethylene, polyurethane, Pebax, nylon, blends) loaded with a radiopaque material (e.g., tungsten, $BaSO_4$). In some embodiments, one or more of the regions 510, 560, 600 of the outer shaft 500 are a singular component, such as a polymer tube with or without variable properties (e.g., stiffness and flexibility) and with or without varying diameters and/or wall thickness.

Figure 24:
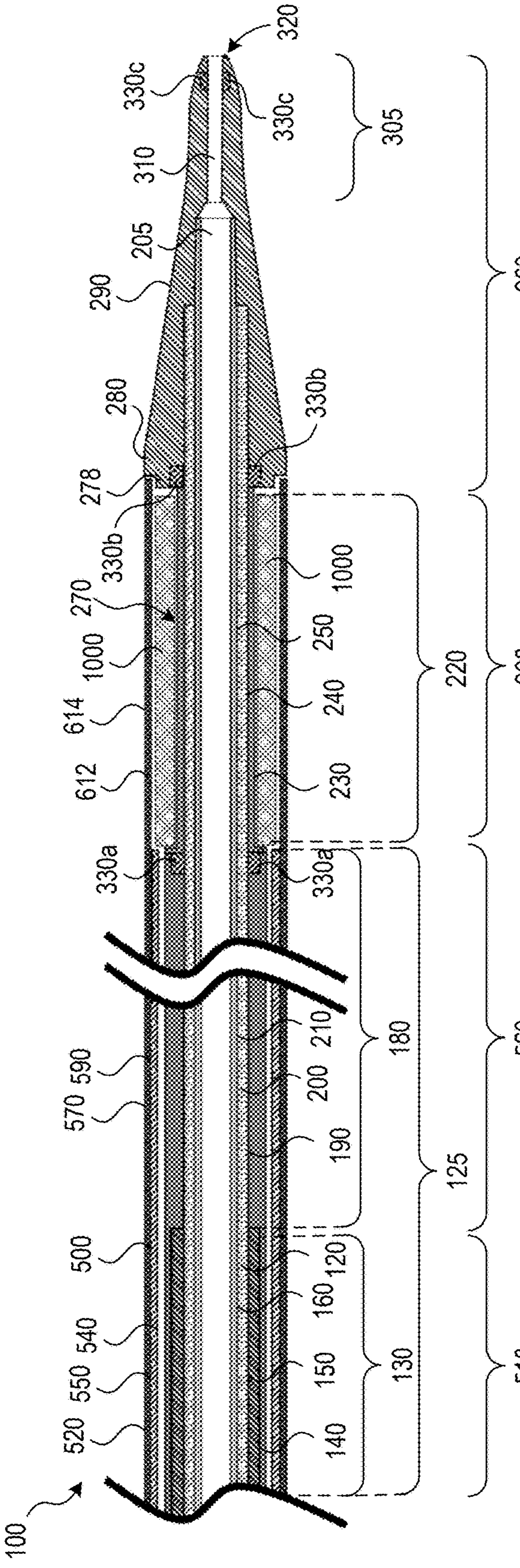
FIGS. 24 and 25 show cross-sectional views of portions of an implant delivery device, in accordance with embodiments of the present technology.
Figure 25:
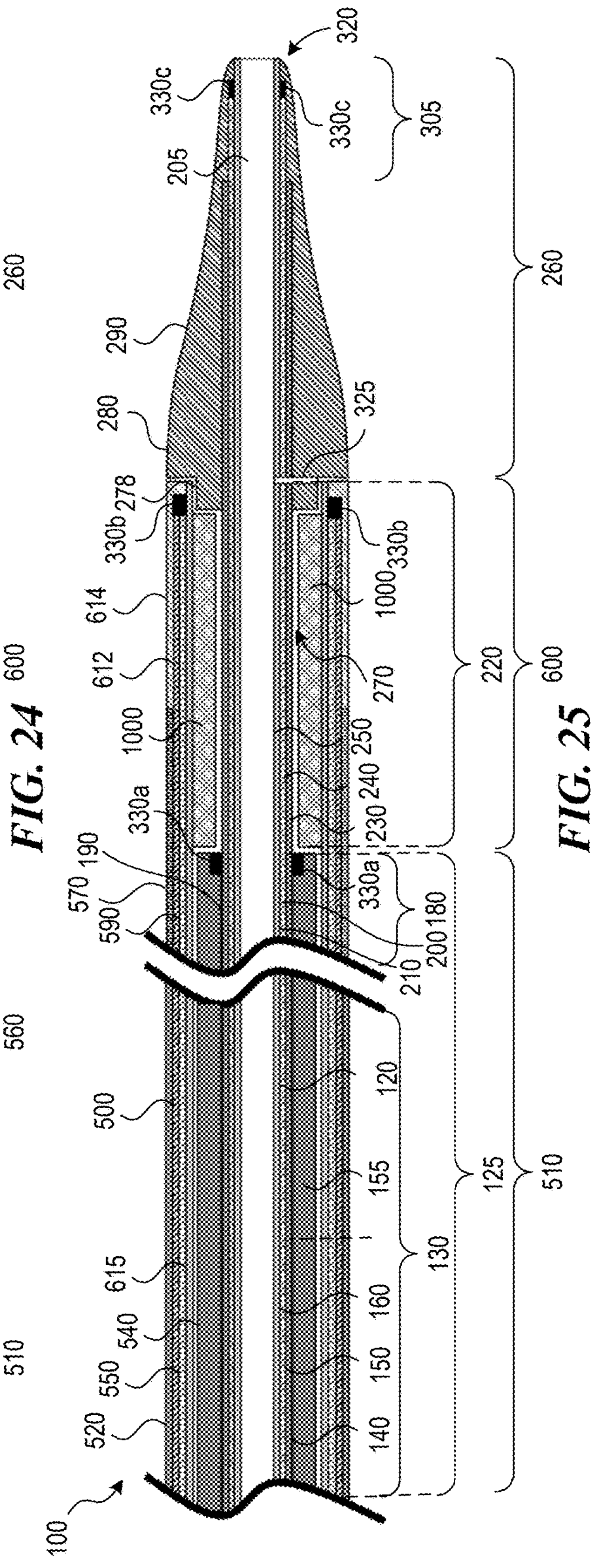

FIGS. 24 and 25 show cross-sectional views of a portion of delivery devices 100 including the inner shaft 120, the outer shaft 500, and the implant 1000 in the constrained state prior to introduction or deployment at the target location. The inner shaft 120 can be identical or generally similar to the inner shafts of FIGS. 11-18B or any of the inner shafts described herein. The outer shaft 500 can be identical or generally similar to the outer shafts 500 of FIGS. 19-23 or any of the outer shaft 500 described herein. The implant 1000 can be identical or generally similar to the implants 1000 of FIGS. 5A-9C or any of the implants 1000 described herein.

As described herein, the inner shaft 120 can have multiple (e.g., two, three, four, or five) regions with one or more varying flexibilities. In some embodiments, the regions can include a PIS region (e.g., the PIS region 125 described herein) proximal to where the implant 1000 is positioned, an IIS region (e.g., the IIS region 220 described herein) where the implant 1000 is maintained, and a tip region 260 distal to where the implant 1000 is positioned. The PIS region 125 can have two or more subregions, including the PIS 130 and one or more MIS 180. The PIS 130 can be between 30 cm and 135 cm in length, or any length therebetween, or least 30 cm, 75 cm, or 135 cm. The PIS 130 can include the PIS liner 160, the PIS functional member 150, and the PIS jacket 140. The PIS liner 160 can extend through the one or more MIS 180, the IIS region 220, and into the tip region 260. The PIS functional member 150 can be, for example, a braid of stainless steel. The PIS functional member 150 can extend through one or more of the MIS 180, the IIS region 220, and into the tip region 260. The PIS jacket 140 jacket can be made from nylon and can have an outer diameter between 0.5 mm and 2.5 mm, or any outer diameter therebetween, or at most 0.5 mm, 0.75 mm, 1 mm, 1.25 mm, 1.5 mm. 1.75 mm, 2 mm, or 2.5 mm. The MIS 180 can include an MIS liner 210, an MIS functional member 200, and an MIS jacket 190. The MIS liner 210 can be a continuation of the PIS liner 160. The MIS functional member 200 can be a continuation of the PIS functional member 150. The proximal MIS jacket 190 and the distal MIS jacket 190 can be block co-polymers with varying flexibility.

The inner shaft 120 can include the IIS region 220 that maintains the implant 1000, as described in more detail with reference to FIGS. 11-17B. The IIS region 220 can be generally long enough to accommodate an implant 1000 between 2 cm and 15 cm in length, or any length therebetween, or at least 2 cm, 5 cm, 6 cm, 8 cm, 10 cm, or 15 cm in length. The IIS liner 250 can be a continuation of the PIS liner 160 and/or MIS liner 210. The IIS functional member 240 can be a continuation of the PIS functional member 150 and/or the MIS functional member 200. In some embodiments, the IIS jacket 230 is made of urethane. The tip region 260 can be between 1 cm and 6 cm in length, or any length therebetween, or at least 1 cm, 1.5 cm, 3.5 cm, 4 cm, or 6 cm in length. The MIS liner 210 can extends the length of the tip region 260. The MIS functional member 200 can extend into the tip region 260. The tip region 260 can be made of a urethane or other suitable polymer. The inner shaft 120 can have an additional one or more of the functional members 155 that extends from the POS region 510 to the IOS region 600. The functional member 155 can become generally more flexible as it approaches the IOS region 600 from the POS region 510.

As described herein, the outer shaft 500 can have multiple regions, including the POS region 510 proximal to where the implant 1000 is positioned, the IOS region 600 where the implant 1000 is positioned and extending into the recess 270. The POS region 510 can include the POS liner 540 which can be made from a fluoropolymer or other low coefficient of friction polymer (i.e., a polymer with a coefficient of friction less than 0.3 or preferably less than 0.1) and can through the length of the outer shaft 500, forming the MOS liner 580 and the IOS liner 610. The POS functional member 550 can be a coil, which extends the length of the outer shaft 500, forming the MOS functional member 590 and/or the IOS functional member 612 (e.g., as shown in FIG. 25). The POS jacket 520 can be made from nylon. The MOS region 560 can include the MOS jacket 570 made of block co-polymers that increase in flexibility toward the IOS jacket 614. The IOS jacket 614 can be made of urethane. The outer shaft 500 can also include the radiopaque marker 330 at the outer shaft distal end region 620.

As described in more detail herein (e.g., with reference to FIGS. 19-23), the outer surfaces of the outer shaft 500 can be coated or layered to increase or decrease friction/movement with respect to the vasculature, and/or other devices used during the procedure, such as guiding catheters, introducers, and the like. Additionally or alternatively, the inner surfaces of the outer shaft 500 can be coated or layered to increase or decrease friction/movement with respect to inner shaft 120 and/or surfaces of the implant 1000. Surface coatings can be or include hydrophilic, hydrophobic, fluoropolymers, silicone, and/or polymer. In addition, one or more components can be made from impregnated materials, such as PTFE impregnated polyimide to increase or decreased friction/movement within the delivery device 100.

Referring to FIGS. 24 and 25 collectively, the inner shaft 120 can include the PIS liner 160 which extends from a proximal region of the delivery device 100 to a region adjacent the distal tip end region 320. The PIS functional member 150 can be a stainless-steel braid that extends to a region adjacent the radiopaque markers 330 and/or adjacent the distal tip end region 320. The PIS jacket 140 can be a combination of block co-polymers with different flexibilities to optimize the bend stiffness along the length of the delivery device 100. The inner shaft 120 can include a functional member 155 made of hypotube (e.g., stainless steel or NiTi), with varying fenestrations or cuts along a portion of the length, to enable decreased bend stiffness in the tip region 260 compared to the POS region 510. Additionally or alternatively, the functional member 155 can extend from a handle (e.g., the handle 800 of FIGS. 29A-31) to the POS region 510, the IOS region 600 (i.e., adjacent the implant 1000), and/or to the tip region 260.

In some embodiments, the radiopaque marker 330 can be incorporated into the functional member 155 adjacent the tip region 260 (e.g., the radiopaque marker 330*b*) to assist in identifying the location of the implant 1000. The functional member 155 can be configured to act as a backstop to the IOS region 600 to keep the implant 1000 from moving proximally during deployment while the outer shaft 500 is retracted. In some embodiments, the tip region 260 can be between 20 mm and 50 mm, or 20 mm, 30 mm, 40 mm, or 50 mm in length, and the recess 270 can be between 2.5 cm and 15 cm, or 2.5 cm, 5 cm, 6 cm, 8 cm, 10 cm or 15 cm in length. The tip region 260 can be manufactured (e.g., molded) separately and then coupled to the rest of the inner shaft 120. Additionally or alternatively, the tip region 260 can be insert molded to the rest of the inner shaft 120.

The outer shaft 500 can include a POS liner 540 which extends to a region of the outer shaft 500 adjacent the tip region 260. Over the POS liner 540 can be a POS functional member 550, consisting of a stainless-steel braid with a nitinol coil over the braid. For example, the braid can provide a longitudinal stiffness component and the coil over the braid can keeps the braid from expanding due to the chronic outward force the implant 1000 applies to the outer shaft 500. This POS functional member 550 construction can extend an entirety of the length of the delivery device 100 to a region of the outer shaft 500 adjacent the tip region 260.

As shown in FIG. 25, in addition to the one or more outer shaft functional members 550, 590, 612, the outer shaft 500 can include one or more tensile members 615. The one or more tensile members 615 can provide greater tensile strength to the outer shaft 500, and thus the delivery device 100. The one or more tensile members 615 can be made of polyester fibers, aramid (e.g., Kevlar) fiber(s), liquid crystal fiber(s) (e.g., Vectran), metal wire(s), polymer fiber(s), etc. which can be wound and/or within a braid. In some embodiments, the tensile member 615 is made of one or more strings that do not entirely surround the outer shaft 500, the recess 270, and/or the implant 1000. The tensile member 615 can have a total tensile strength between 0.5 and 5 pounds, or at least 0.5, 1.5, 2.5, or 5 pounds. The one or more outer shaft functional members 550, 590, and/or 612 and the one or more tensile members 615 can add tensile strength to the outer shaft 500 and can be disposed within the outer shaft 500 as described herein. The one or more outer shaft functional members 550, 590, and/or 612 and the one or more tensile members 615 can be in the form of fiber(s), wire(s), and/or a braid. In some embodiments, the one or more tensile members 615 are underneath, over, and/or interwoven into one or more outer shaft functional members 550, 590, and/or 612. For example, the one or more tensile members 615 can be underneath, over, and/or interwoven into the braid portion of the functional member 550. Additionally or alternatively, the one or more tensile members 615 and the braid portion of the functional member 550 can both be underneath the coil portion of the functional member 550.

Additionally or alternatively, the tensile member 615 can be incorporated within or between the POS liner 540 and the POS jacket 520 and/or the MOS jacket 570. The POS jacket 520 and/or the MOS jacket 570 can be made of multiple polymers along the length of the delivery device 100 to obtain the desired flexibility and properties. In some embodiments, the POS jacket 520 has a generally higher stiffness in bending and moving than the MOS jacket 570 and/or the IOS jacket 614. In some embodiments, one or more polymers are incorporated into the MOS jacket 570 and/or the IOS jacket 614 to decrease the delivery device 100 resistance to bending, making the delivery device 100 more flexible and easier to navigate through more tortuous anatomy. The outer shaft jackets 520, 570, 614 can be mainly made of nylon and/or block co-polymers and can extend over at least a portion of the recess 270.

In some embodiments, one or more outer shaft functional members 550, 590, and/or 612 and the one or more tensile members 615 are within the outer shaft 500 as one or more fibers, a braid, and a coil. From inside to outside, the outer shaft 500 can include a liner (e.g., the POS liner 540), one or more fibers (e.g., the one or more tensile members 615), the braid (e.g., the braid of the functional member 550), the coil (e.g., the coil of the functional member 550), and the jacket (e.g., the outer shaft jackets 520, 570, 614). The outer shaft 500 and the one or more components of the outer shaft 500 described herein can form a perimeter around the recess 270 and/or the implant 1000.

In some embodiments, the delivery device 100 has an overall working length between 140 cm and 150 cm or any length therebetween, or at least 140 cm, 145 cm, and 150 cm. The overall working length of the delivery device 100 can be any length that enables the delivery device 100 to approach and reach the target vasculature from any typical access point. In some embodiments, the delivery device 100 with implant 1000 is configured to reach the venous sinuses (VS). For example, using a femoral approach the length of the delivery device 100 can be such that the second zone end structure(s) 1110 are positioned adjacent the torcula and the implant 1000 extends into the sigmoid sinus (SS).

Figure 26:
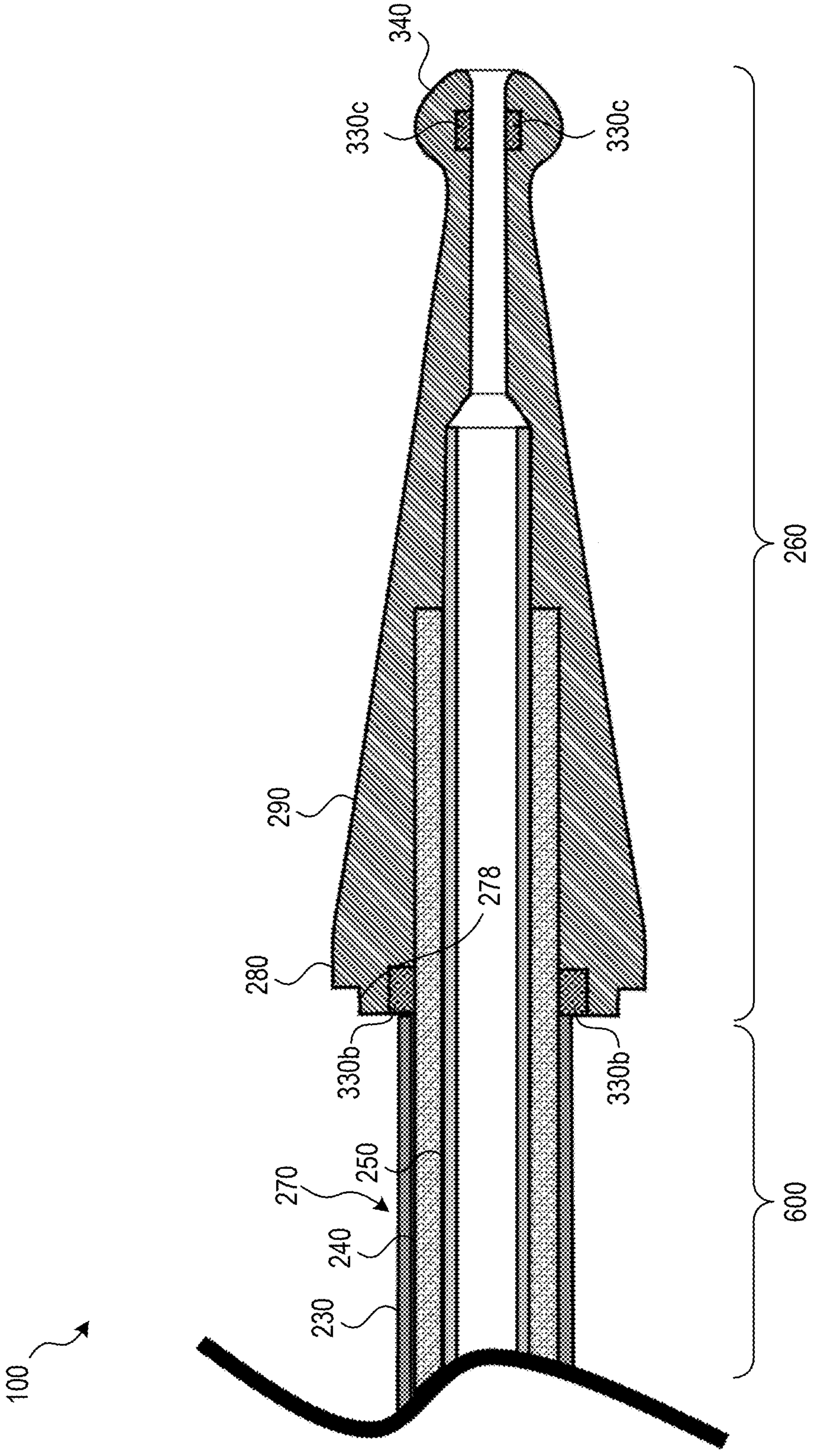
FIGS. 26-28 show cross-sectional views of a distal portion of inner shafts of an implant delivery device, in accordance with embodiments of the present technology.
Figure 27:
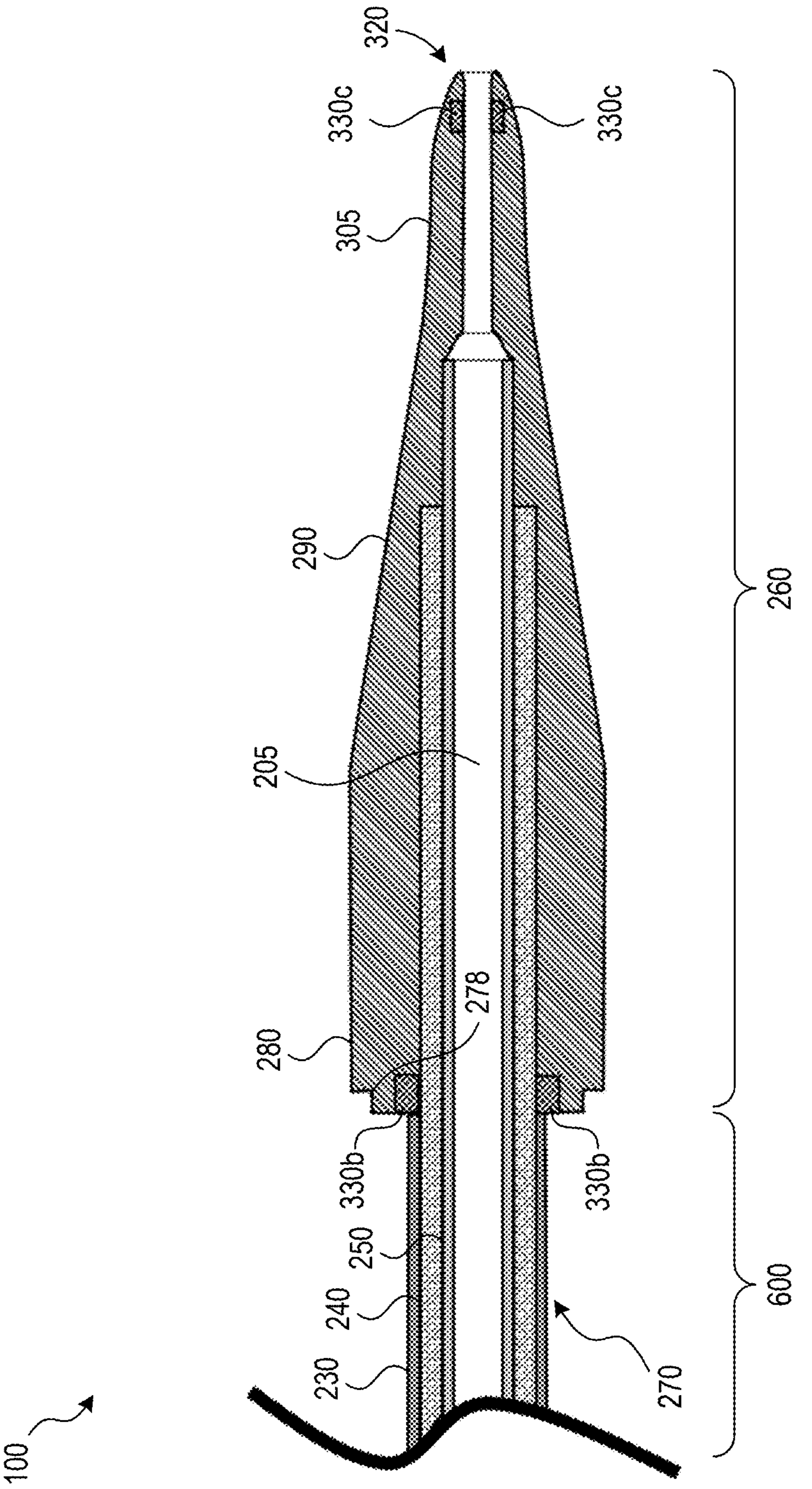
Figure 28:
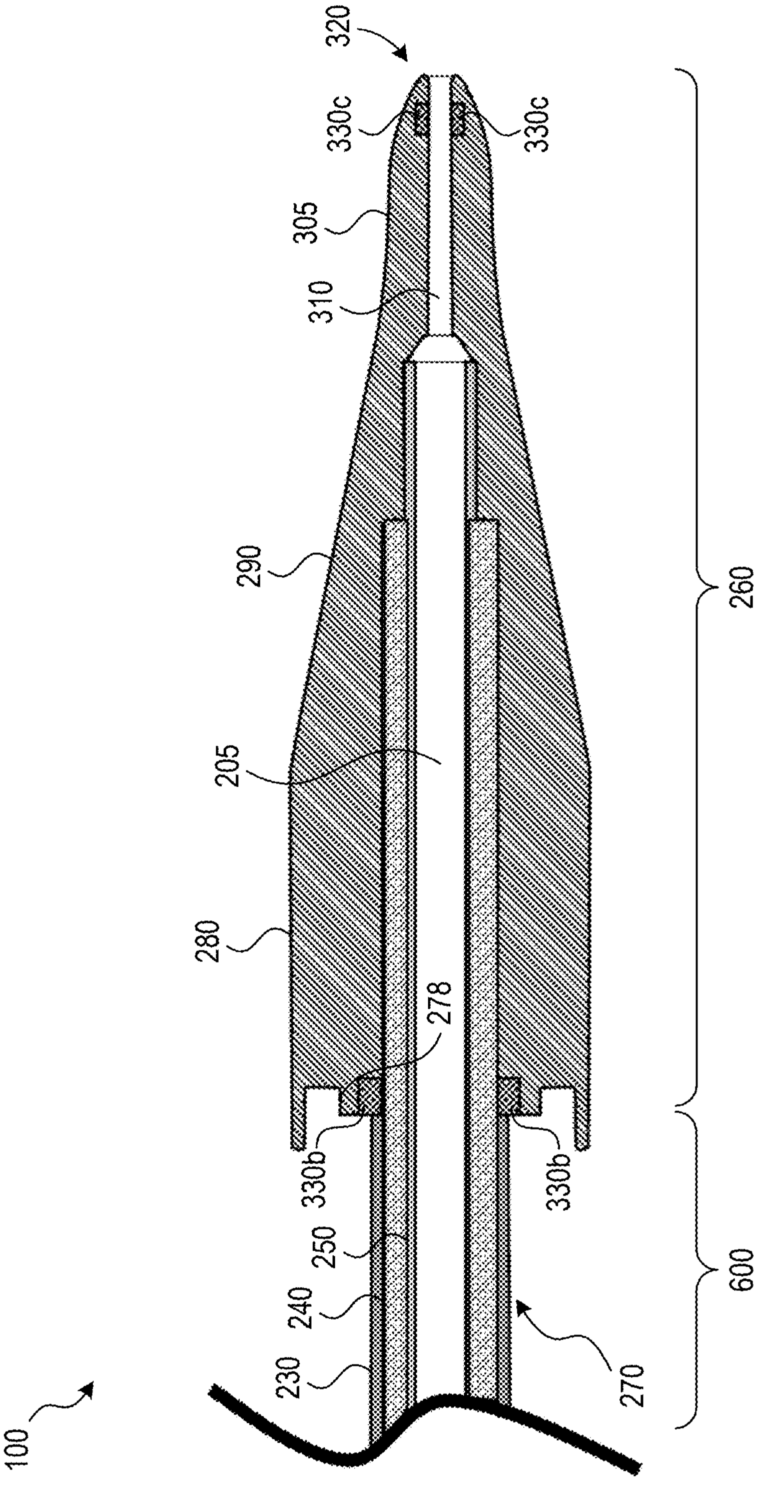

FIGS. 26-28 show cross-sectional views of a distal portion of inner shafts 120 of the delivery device 100 described herein. In some embodiments, the tip region 260 contains an enlarged distal tip end region 340 which has a shape that is atraumatic in a way that it makes it very difficult for any leading edge of the tip region 260 to catch on or cause trauma to small vessels (e.g., cortical veins) and/or when navigating around tight bends. As shown in FIG. 26, the enlarged distal tip end region 340 can resemble a ball or an enlarged portion relative to the adjacent diameter/cross-sectional profile. Other shapes can be used to the same effect of keeping the lumen 205/distal tip end region 320 edge of the tip region 260 away from the vessel wall throughout navigation.

In some embodiments, the tip region 260 is generally longer to provide a very gradual transition from the distal tip end region 320 to the more proximal locations of the delivery device 100. As shown in FIG. 27, the distal tip 280 can be generally longer in length (e.g., at least 1 mm, 2 mm, 4 mm, 6 mm, 10 mm, or 20 mm in length), providing a smooth transition into IOS region 600. In some embodiments, the distal tip 280 and/or the tip region 260 can be generally longer in longitudinal length, enabling flexible and low-profile portions (e.g., part or all of the distal tip taper 290, distal tip extended region 305, distal tip end region 320) to be navigated around tortuous curves, such as the sigmoid sinus (SS) at the takeoff from the jugular vein (JV), before the IOS region 600 enters said tortuous region. The tip region 260 can be configured with a flexibility that transitions into the IOS region 600, enabling smooth and atraumatic advancement of the delivery device 100 with implant 1000 to the target location.

In some embodiments, the tip region 260 can have a distal tip extended lumen 310 extending at least partially through the tip region 260, with or without an enlarged distal tip end region 340. If incorporated, the distal tip extended lumen 310 can extend proximally from or adjacent the distal end of the tip region 260. Having a smaller diameter in the lumen 205 reduces the clearance between the guide wire 1600 and the distal tip extended lumen 310, e.g., to minimize any exposed edge of the distal end of the delivery device 100 to the vasculature, and in doing so, reducing the potential for trauma to the vasculature. For example, if the guide wire 1600 is a 0.014" diameter guide wire, the lumen 205 can be nominally 0.017" and the distal tip extended lumen 310 can be less than 0.017", or between 0.0145" and 0.016". A distal tip extended lumen 310 with or without an enlarged distal tip end region 340, significantly reduces the possibility of the tip region 260 catching on or causing trauma to small vessels.

As shown in FIG. 27, the tip region 260 can have a recess 270 formed by the ledge 278, which serves as a location for the outer shaft distal end region 620. By having the outer shaft distal end region 620 can extend beyond the implant 1000 and into the ledge 278 of the recess 270, this allows for some relative movement of the outer shaft 500 with respect to the inner shaft 120 without exposing the implant 1000 during introduction and advancement of the delivery device 100 with implant 1000. The ledge 278 of the recess 270 can also allow for some initial retraction of the outer shaft 500, prior to initiation of the implant 1000 release, to aid in optimizing position of the implant 1000 during deployment. The ledge 278 of the recess 270 can also aid in creating a gradual transition in flexibility within IOS region 600 of the delivery device 100. The ledge 278 of the recess 270 can typically be between 0.5 mm to 20 mm in length, or any length therebetween, or at most 0.5 mm, 5 mm, 10 mm, or 20 mm. The ledge 278 of the recess 270 thus enables maintenance of the atraumatic outer surface of the delivery device 100 when the implant 1000 is positioned within the IOS region 600. The tip region 260 can also have some overlapping material that extends proximally over the distal end of the outer shaft 500 to reduce the likelihood one or more edges of the components of the delivery device 100 are exposed when the outer shaft 500 moves proximally relative to the inner shaft 120 at any time prior to initiating deployment of the implant 1000.

The tip region 260 can also be made from one or more materials, for example, the tip region 260 can be made from a single polymer, e.g., polyethylene, polyurethane, nylon and nylon blends, block co-polymers, blends, and/or can be made with multiple polymers. For example, the distal tip 280 can be made from one or more materials of different density (e.g., different polymers of polyethylene, polyurethane, etc.) than the distal tip taper 290, the distal tip extended region 305, and/or the distal tip end region 320. In some embodiments, one or more of the distal tip 280, the distal tip extended region 305, and/or the distal tip end region 320 are made from different polymers of one or more different densities (e.g., going from high-density polyethylene to a lower density polyethylene or from a polyurethane to a nylon or Pebax). Additionally or alternatively, one or more components of the tip region 260 can be radiopaque and/or contain one or more of the radiopaque markers 330. For example, the distal tip extended region 305 can be radiopaque (e.g., radiopaque loaded with material such as a tungsten loaded polymer). In some embodiments, the distal tip extended region 305 extends between 1 mm and 8 mm, or any distance therebetween, or at most 1 mm, 2 mm, 5 mm, or 8 mm from the distal tip end region 320.

Figure 29A:
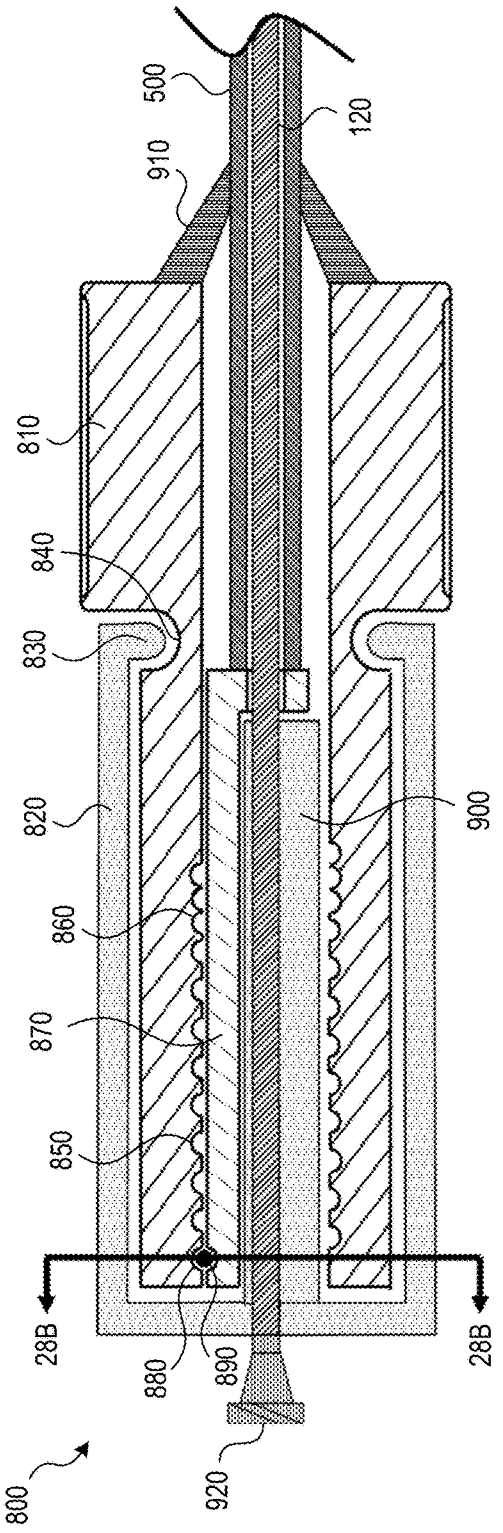
FIGS. 29A-31 show handles of an implant delivery device in various states, in accordance with embodiments of the present technology.

FIGS. 29A-31 show handles 800 of delivery device (e.g., the delivery device 100 described herein) in various states. The handle 800 can be configured to enable the user to manipulate the delivery device 100 with the implant 1000, deploy the implant 1000, and remove the delivery device 100 from the vasculature. As shown in FIGS. 29A and 29B, the outer shaft 500 can be retracted, and in FIG. 29C the outer shaft 500 can be advanced to cover the implant 1000. The handle 800 can contain a handle base 820 and a rotator 810, which when rotated, moves the outer shaft 500 with respect to the inner shaft 120, or in the delivery device 100 with a rail configuration, the proximal outer rail shaft 630 and the proximal inner rail shaft 360. The rotator 810 can move a ball 890 along the rotator outer shaft groove 850 when rotated. The rotator outer shaft groove 850 is a variable pitch spiral groove where at the initiation of implant 1000 deployment, it takes relatively more rotation to affect a small movement in the outer shaft 500, followed by a coarser pitch which increases the rate of retraction of the outer shaft 500 per rotation.

When the implant 1000 is in the desired position within the vasculature for deployment, the rotator 810 can be rotated which moves a ball 890 along the rotator outer shaft groove 850. The rotator outer shaft groove 850 can be a spiral groove, with or without variable pitch. Variable pitch can be implemented, for example, with a fine pitch rotator outer shaft groove 860 such that at the initiation of the implant 1000 for deployment, it takes relatively more rotation to affect a small movement in the outer shaft 500, to aide in accurately placing and/or securing an initial length of the implant 1000 in the vessel. As the implant 1000 is further deployed, the pitch can be coarser such that relatively less rotation is required to deploy the remainder of the implant 1000, decreasing the force required to deploy the implant 1000 and reducing procedure time.

Figure 29B:
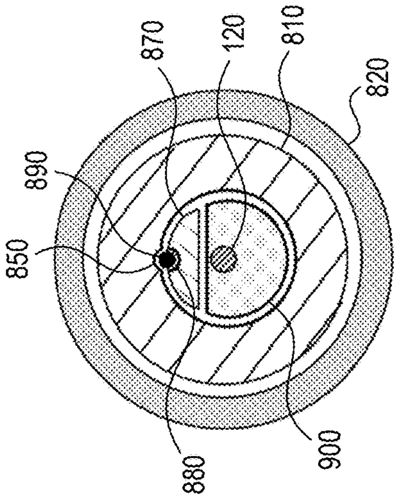
Figure 29C:
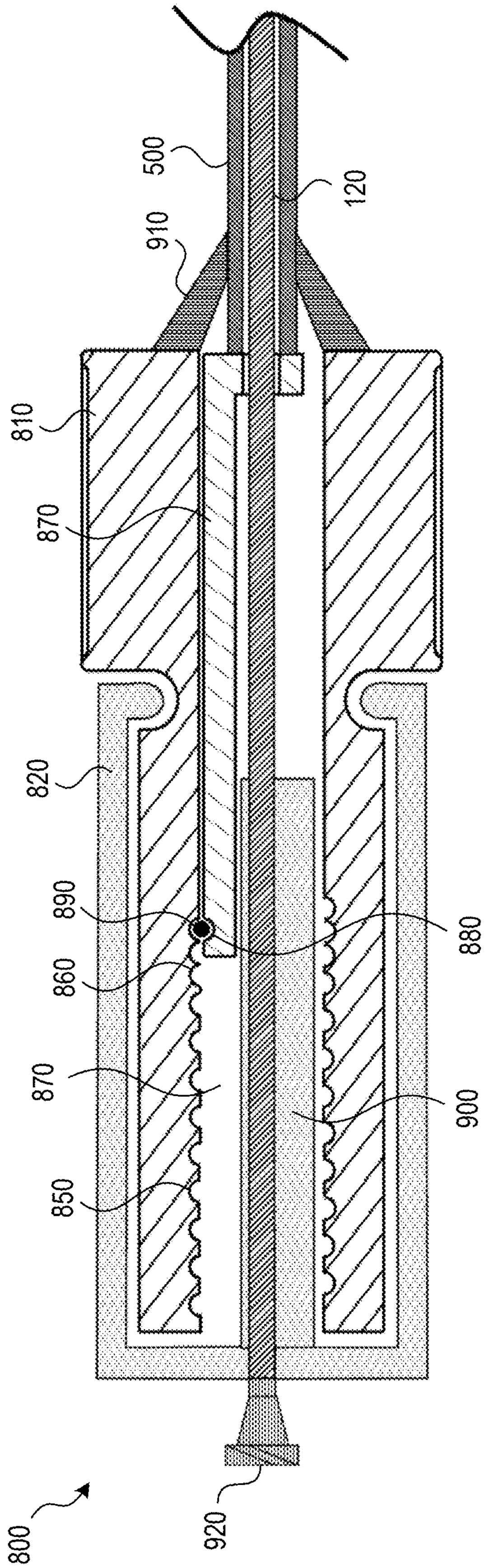

The ball 890 can also be in communication with the outer shaft rail 870 which contains an outer shaft rail pocket 880, which holds the ball 890 in position with respect to the outer shaft rail 870. The outer shaft rail 870 can be attached to the outer shaft 500. The rotator 810 can be held in longitudinal position with respect to the handle base 820 buy a handle base tongue 830 and corresponding rotator locating groove 840. As shown in FIG. 29B, the outer shaft rail 870 can be constrained from significant rotation with respect to the handle base locator 900 with a flat on flat, or matching/constraining surfaces arrangement. The handle base locator 900 can be part of the handle base 820 and/or a separate component. The inner shaft 120 can also extend inside the outer shaft 500 and through or in engagement with the handle base locator 900 and is in communication with the lumen port 920. The lumen port 920 can be used to flush the lumen 205 and can contain a fitting, such as a Luer fitting.

The handle 800 can contain a strain relief 910 to assist in preventing kinking of the delivery device shafts as they exit the handle. The rotator 810 and/or handle base 820 surfaces can be grooved, slotted, knurled, textured, or modified to optimize tactile feel and grip with a gloved hand(s). The area formed between the inside of the outer shaft 500 and the outside of the inner shaft 120 and implant 1000 can have a fluid communication port (not shown) similar to the lumen port 920 (e.g., a Luer fitting) to enable fluid flushing of that area. In a rail configuration, the lumen port 920 is not required. The handle 800 can have a strain relief 910 to assist in preventing kinking of the delivery device shafts as they exit the handle 800. The rotator 810 outer surface can be grooved, and the handle base 820 surface can be knurled.

Figure 30A:
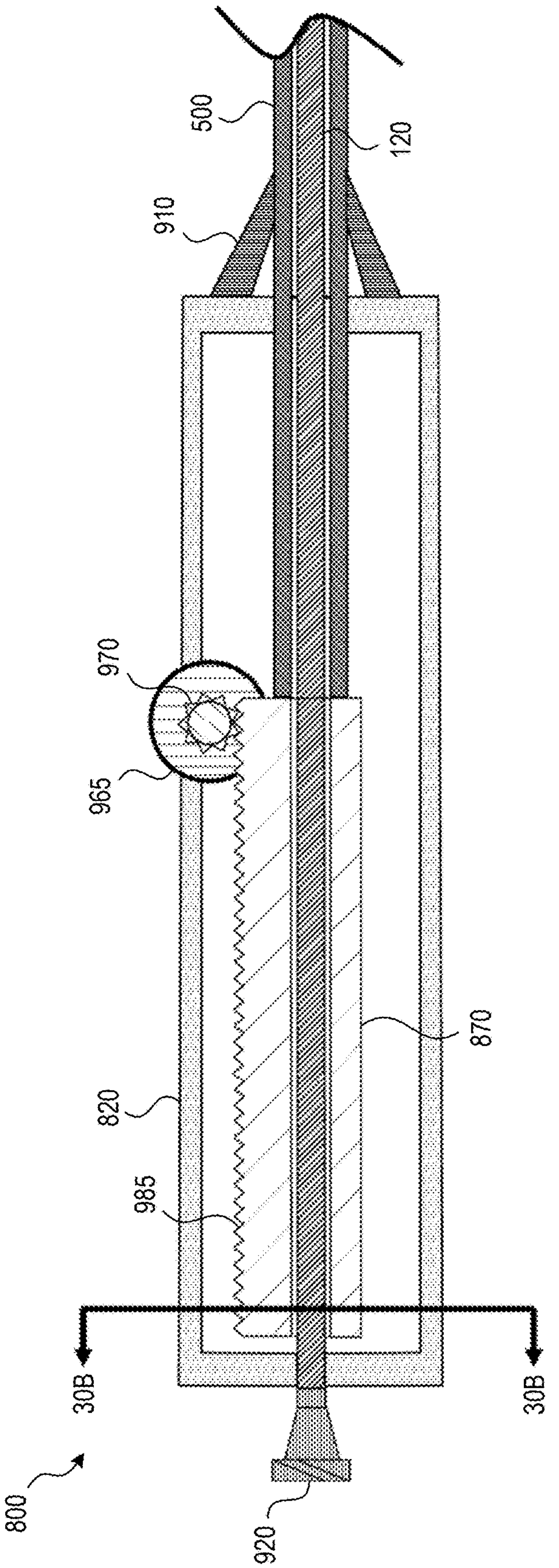
Figure 30B:
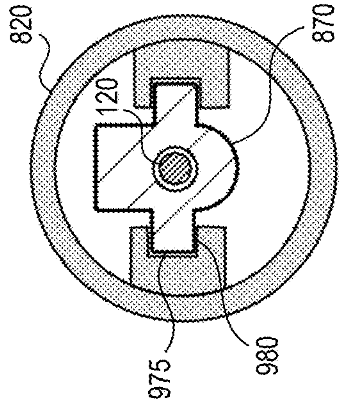

FIGS. 30A and 30B show various views of handles of the delivery device 100 with an outer shaft 500 retracted. The delivery device 100 can be identical or generally similar to the handle described in FIG. 3, including a thumbwheel activated retraction of the inner shaft 120. The handle 800 can be identical or generally similar to the handle 800 of FIGS. 29A-29C. The handle 800 can further have a handle base 820, with a thumbwheel 965 located such that actuation is accessible external to the handle base 820. The thumbwheel can be functionally coupled to one or more thumbwheel gears 970 that directly or indirectly effect movement of the outer shaft rail engagement 985. The outer shaft rail engagement 985 can be functionally coupled to the inner shaft 120. Rotating the thumbwheel 965 can cause the outer shaft 500 to move in relation to the inner shaft 120, enabling deployment, or recapture, of the implant 1000. Alignment of the inner shaft 120 and outer shaft 500 with respect to either and/or the handle 800 can be accomplished by having a guide which limits the rotation of either shaft with respect to the handle 800. For example, the outer shaft rail 870 can have one or more alignment tabs 975 that fit in the alignment slots 980. Additionally or alternatively, a reverse configuration is acceptable where the outer shaft rail 870 has one or more alignment slots 980 and the handle base 820 or other component have alignment tabs 975.

Figure 31:
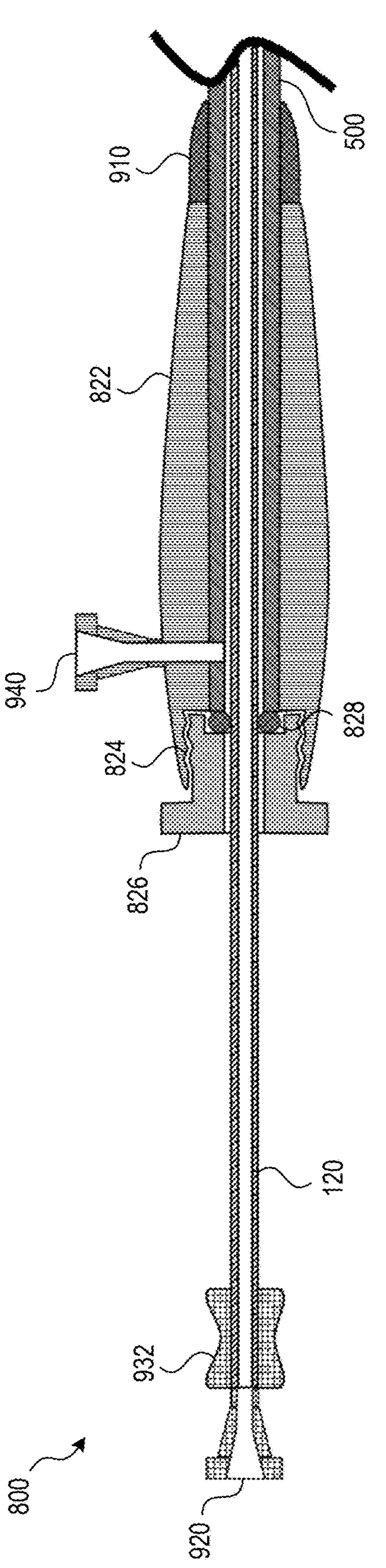

As shown in FIG. 31, the handle 800 can include a handle body 822 coupled to the outer shaft 500 and including a strain relief 910. The handle body 822 can have a second lumen port 940, which can be a Luer fitting flush port, to enable flushing (typically with saline or heparinized saline) of the annulus between the inner shaft 120 and the outer shaft 500. To seal the proximal end of that annulus, there can be an actuator 826 (e.g., a seal actuator) that has one or more threads 824 in common with the handle body 822 to enable the actuator 826 to close down on an O-ring 828 or equivalent component and create a seal. Compression of the O-ring 828 can be of sufficient force to also serve as a locking mechanism and prevent movement of the inner shaft 120 with respect to the outer shaft 500 until it is loosened as part of deploying the implant 1000. The inner shaft 120 can have a pin hub 932. To deploy the implant 1000, the actuator 826 can be loosened, the pin hub 392/inner shaft 120 held in place, while the handle body 822 and the outer shaft 500 are retracted.

In one or more embodiments, the handle 800 or other location on or in the delivery device 100 can include a lock 960, to prevent unwanted movement of the inner shaft 120 with respect to the outer shaft 500. Additionally or alternatively, the handle 800 can include the second lumen port 940 enabling the area between the inner shaft 120 and outer shaft 500 being flushed with fluid (e.g., saline or heparinized saline) and a strain relief 910 to relieve strain on the delivery device 100.

Figure 32:
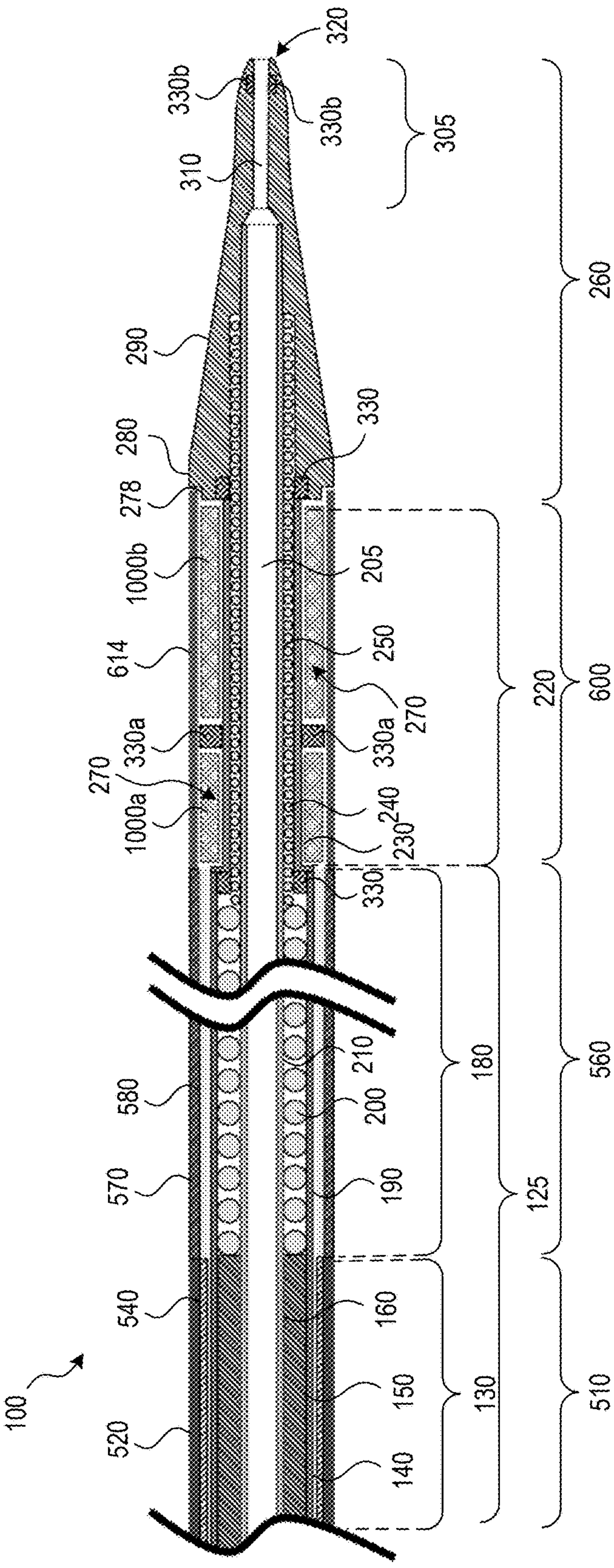
FIG. 32 shows a cross-sectional view of an implant delivery device configured to deploy two implants, in accordance with embodiments of the present technology.

FIG. 32 shows a cross-sectional view of a delivery device 100 (e.g., the delivery device 100 described herein) configured to deploy two implants (e.g., the implants 1000 described herein) In some embodiments, the delivery device 100 is configured deploy multiple implants 1000*a* and 1000*b* (collectively referred to as "multiple implants 1000") at multiple locations, enabling the deployment of a generally longer implant length within one or more vessels. This can be beneficial to not have to introduce and navigate multiple catheters to the target locations, reducing equipment costs, reducing procedure times, and improving safety. Examples include a delivery device 100 with a distally located implant 1000 for deployment in the transverse sinus (TS) and sigmoid sinus (SS) and a more proximally located (on the delivery device 100) implant 1000 for delivery in the contralateral transverse sinus (only), or the reverse configuration. Any combination of implants 1000 can be configured, such as a superior sagittal sinus (SSS) through sigmoid sinus (SS) implant 1000 along with a transverse sinus (TS) implant 1000, a transverse sinus (TS) through sigmoid sinus (SS) implant 1000 and/or a superior sagittal sinus (SSS) only implant 1000. In addition, three or more implants 1000 can be placed within one of the delivery devices 100, such as a transverse sinus (TS) through sigmoid sinus (SS) implant 1000, a superior sagittal sinus (SSS) only implant 1000, and a contralateral transverse sinus only implant 1000. These multiple implants 1000 can be in any desired order or configuration.

Multiple implants 1000 can be used to adjust the implanted region length, such as by having a transverse sinus (TS) through sigmoid sinus (SS) implant (e.g., between 6 and 10 cm in longitudinal length, or any length therebetween) as well as one or more transverse sinus (TS) only and/or superior sagittal sinus (SSS) only implants on the same delivery device 100. In this manner, the transverse sinus (TS) through sigmoid sinus (SS) implant 1000 can be deployed and the patient tested for relief of symptoms as well as other visual and/or physiological indicators. Then, if desired, additional transverse sinus (TS) and/or sigmoid sinus (SS) implants can be deployed, each time with the ability to re-evaluate the patient without having to remove and then introduce a new catheter. Additionally, a superior sagittal sinus (SSS) only implant 1000 can be deployed. Other embodiments include multiple relatively short implants 1000 (e.g., at most 8 cm in length) on the same delivery device 100 to enable constructing an implanted region of the desired length and in the desired location(s). Additional implants 1000, such as a transverse sinus (TS) only implant 1000, sigmoid sinus (SS) only implant 1000, and superior sagittal sinus (SSS) only implants 1000 can be constructed as described herein with reference to FIGS. 5A-9C, though the implants 1000 can also be generally shorter in length (e.g., less than 2 cm in overall length).

Figure 33A:
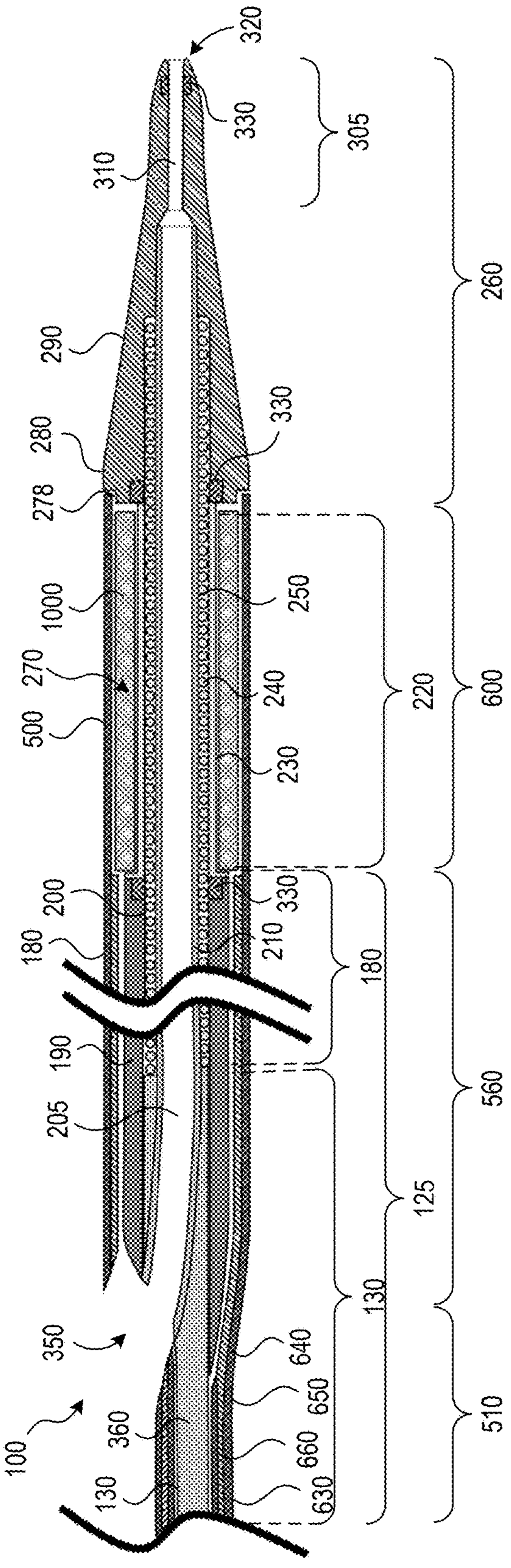
FIGS. 33A and 33B show cross-sectional views of an implant delivery device with a rail type shaft in various states, in accordance with embodiments of the present technology.
Figure 33B:
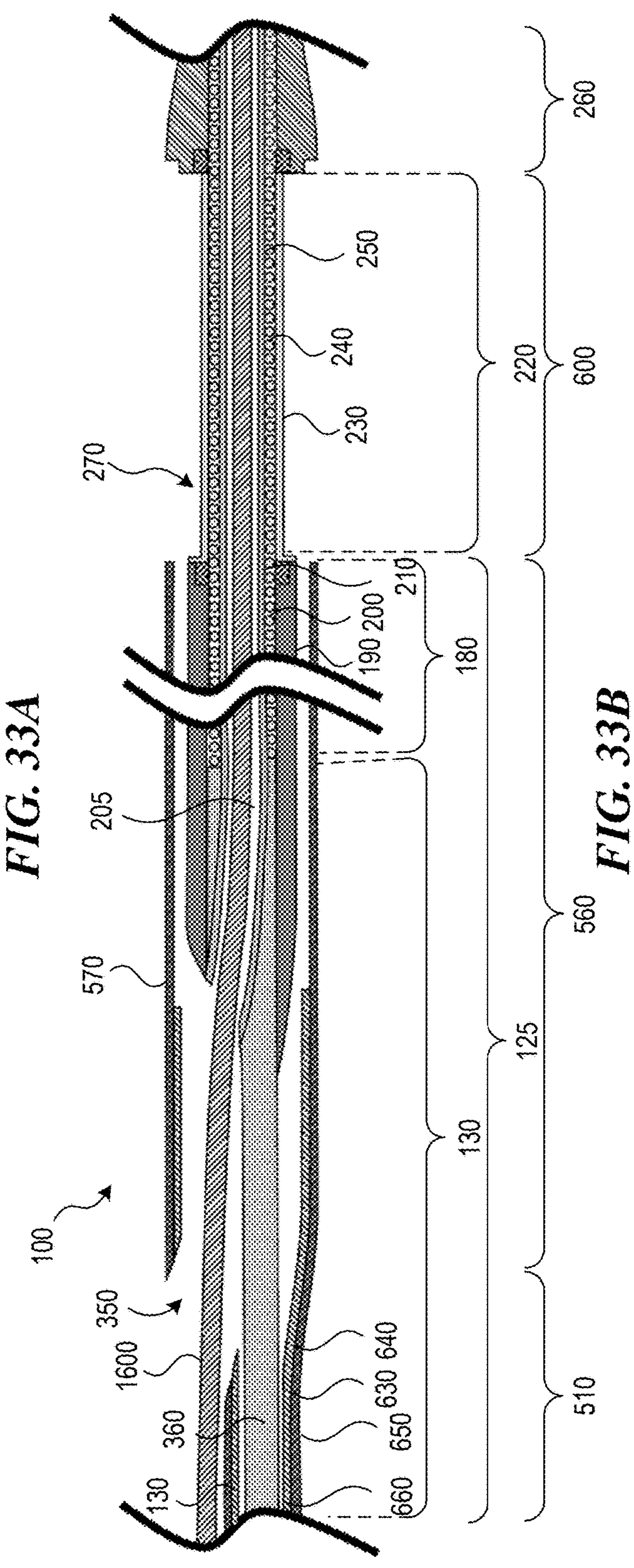

FIGS. 33A and 33B show cross-sectional views of a delivery device (e.g., the delivery devices 100 described herein) with a rail type shaft in various states. As shown in FIGS. 33A and 33B, the delivery device 100 with a lumen 205 that is generally shorter in length enabling use of the lumen 205 as a rail type configuration with the implant 1000 constrained within the outer shaft 500 and with the outer shaft 500 advanced (i.e., covering the implant 1000). As shown in FIG. 33B, the outer shaft 500 can be retracted and the implant 1000 deployed. The lumen 205 can be generally shorter in length to allow for a standard-length guide wire (e.g., the guide wire 1600 described herein) to be placed in the patient prior to introducing the delivery device 100 with implant 1000. The MIS 180 or PIS 130 can include a guide wire exit port 350 which allows the guide wire 1600 to exit the delivery device 100 at a location within the patient or a guiding catheter (e.g., the guiding catheter 1700 described herein). As shown, the guide wire exit port 350 can be positioned adjacent the MIS 180 and PIS 130 junction but can also be located elsewhere along the length of the delivery device 100. The proximal inner rail shaft 360 can be preferably less flexible for most of its length than the MIS 180. The proximal inner rail shaft 360 can be of solid construction (e.g., a stainless steel or NiTi wire) or a tubular member (hypotube, polymer, etc.) which can include a functional member 155 and/or jacket, such as a PIS functional member 150 and PIS jacket 140 as described herein. The proximal inner rail shaft 360 can be smaller in diameter and in length than the guide wire 1600, to enable the guide wire 1600 to be outside of the delivery device 100 while still within the vasculature and/or the guiding catheter 1700.

The proximal inner rail shaft 360 can couple the MIS 180, such as by having at least a portion of the proximal inner rail shaft 360 span the guide wire exit port 350 and attach to the MIS 180, such as to one or more of the MIS functional members 200, MIS jacket 190 and MIS liner 210. Alternatively, the guide wire exit port 350 can be entirely within the MIS 180 or PIS 130 with a similar coupling mechanism within the inner shaft 120.

The outer shaft 500 can include the guide wire exit port 350 to allow the guide wire 1600 to exit the delivery device 100. With the outer shaft 500 fully advanced and constraining the implant 1000, the guide wire exit port 350 in the inner shaft 120 and outer shaft 500 can be sufficiently aligned to allow the guide wire 1600 to exit. The guide wire exit port 350 can be in the POS region 510 or MOS region 560 and can be configured to be disposed within or configured as the lumen 205.

The POS region 510 can be configured with a suitable clearance for the proximal inner rail shaft 360. For example, the diameter of the POS region clearance can be between 0.001" and 0.020", or any measurement therebetween, or at least 0.002", 0.012", or 0.020". The POS region 510 can be identical to the POS region 510 described herein, but with generally smaller inside and outside diameters given the dimensions of the proximal inner rail shaft 360 and the need for the guide wire 1600 to be outside of the delivery device 100 while still within the vasculature and/or guiding catheter 1700.

As further shown in FIGS. 33A and 33B, the MOS region 560, in configurations where the guide wire exit port 350 is located at least in part within the MOS region 560, can have a sufficient internal diameter in the portion that will be retracted proximally of the guide wire exit port 350 to accommodate the outside diameter of the proximal outer rail shaft 630 and the guide wire 1600 within the retracted length the MOS region 560. In some embodiments, the configuration of the MOS region 560 allows for movement of the guide wire 1600 and/or delivery device 100 with respect to each other, when the outer shaft 500 is retracted and the implant 1000 is deployed. The outer shaft 500 can include a rail outer shaft functional member 640 and/or a rail outer shaft jacket 650 and/or a rail outer shaft liner 660 generally identical or similar to the functional members, jackets, and/or liners described herein.

Figure 34:
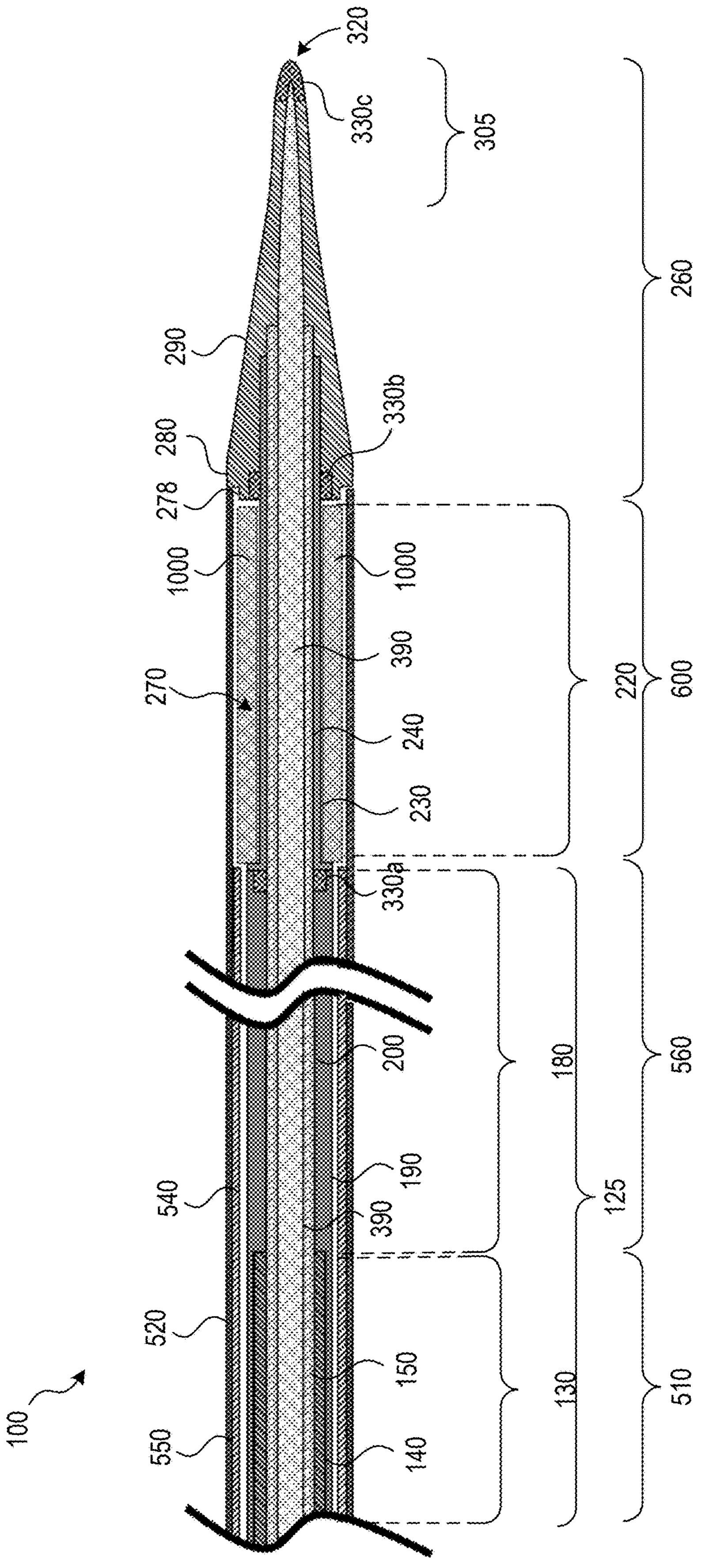
FIGS. 34 and 35 show cross-sectional views of implant delivery devices without a lumen, in accordance with embodiments of the present technology.
Figure 35:
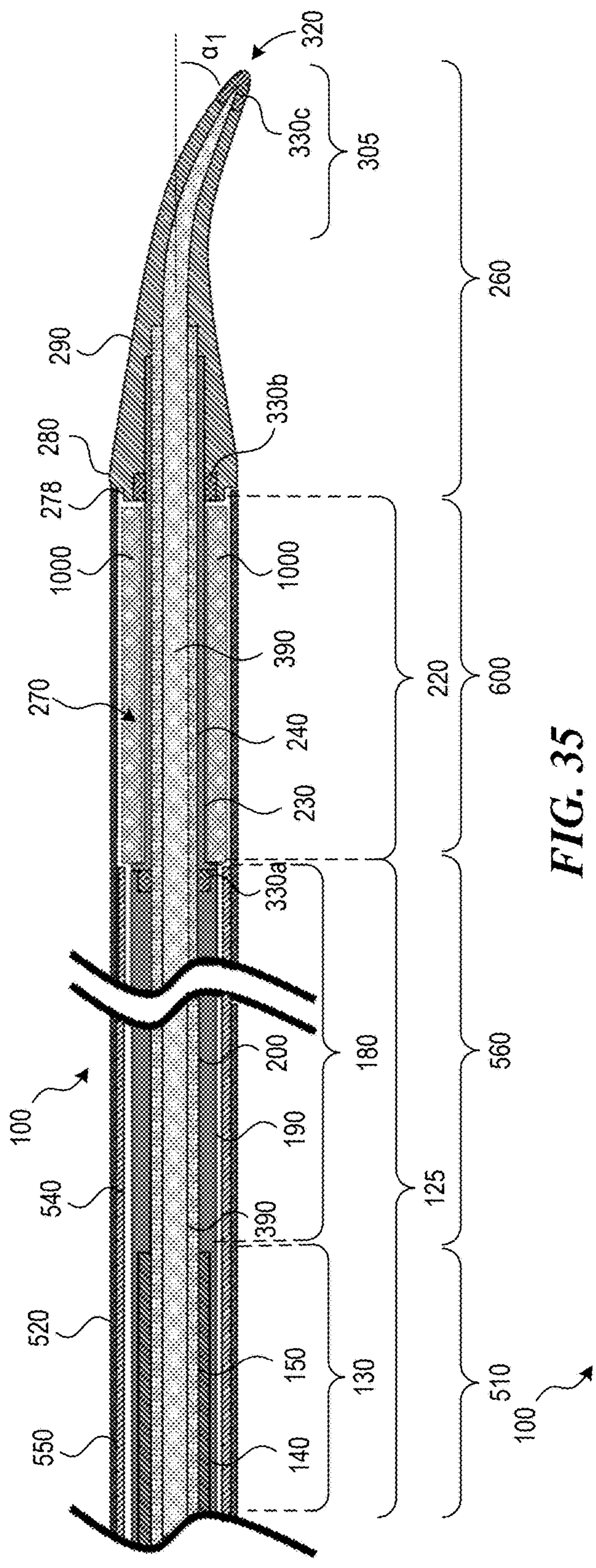

FIGS. 34 and 35 show cross-sectional views of (e.g., the delivery devices 100 described herein) omitting a lumen (e.g., the lumen 205 for the guide wire 1600 described herein). Referring to FIGS. 34 and 35 collectively, the delivery device 100 can include an inner shaft core 390 and the tip region 260 (i.e., an elongated tip region). The inner shaft core 390 can provide additional support to one or more additional components of the inner shaft 120, including compression resistance. The inner shaft core 390 can have multiple sections with varying properties, such as diameter, flexibility, resistance to compression, etc. This can be accomplished by changing materials, having multiple materials in a region (e.g., a polymer and a metal), and/or changing the properties of a material. As shown in FIG. 35, the delivery device 100 can include a preformed shape other than longitudinally straight with respect to the more proximal regions of the delivery device 100. In this embodiment, the tip region 260 has a curve suitable for navigating the target anatomy, for example, navigating the sigmoid sinus (SS), transverse sinus (TS), and/or the superior sagittal sinus (SSS). For example, the tip region 260 can have an angle $\alpha$1 downward relative to the longitudinal length of the delivery device 100 that is between 5° and 90°, or an angle $\alpha$1 therebetween, or at least 15°, 30°, 45°, 60°, or 90°.

Figure 36:
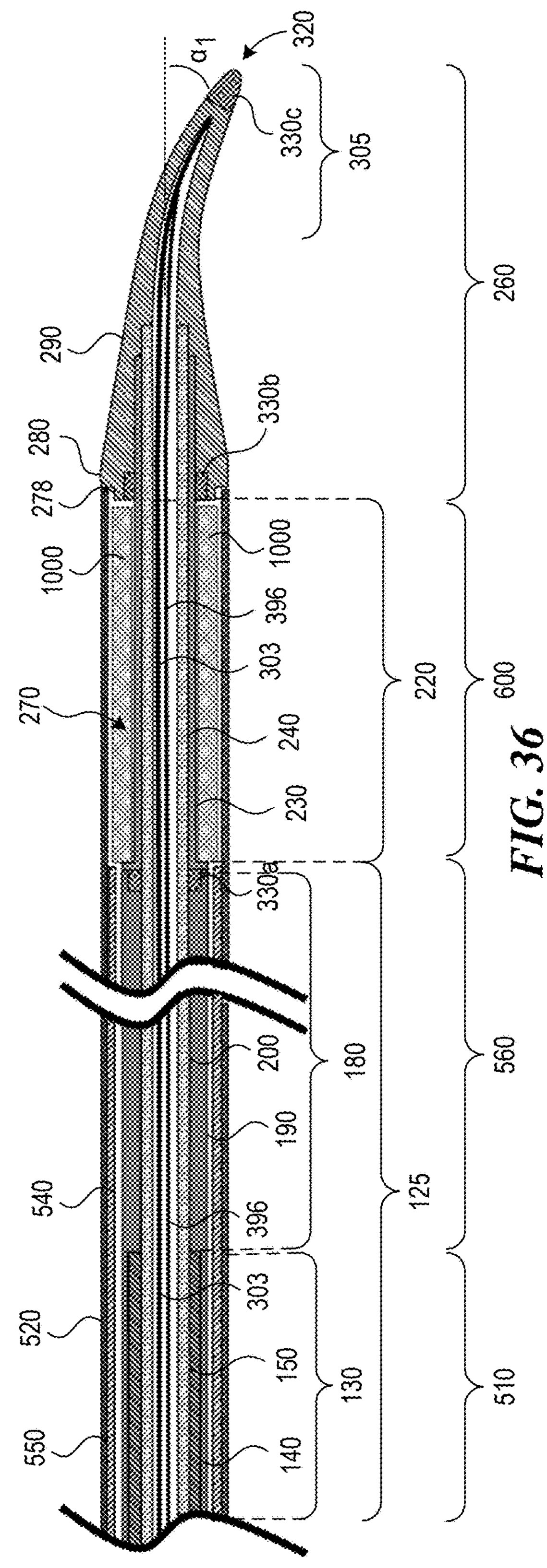
FIG. 36 shows a cross-sectional view of an implant delivery device with a steerable distal portion, in accordance with embodiments of the present technology.

FIG. 36 shows a cross-sectional view of a delivery device 100 (e.g., the delivery devices 100 described herein) with the tip region 260 that is steerable. For example, the delivery device 100 can include a steerable and/or deflectable distal region, such as the tip region 260 and/or a separate component extending into the IIS region 220 or even more proximal that (i.e., as opposed to including the guide wire 1600 of FIG. 10). The delivery device 100 can include a deflection member 396, which can change depending on the angle $\alpha$1, that can be proximally pulled or distally pushed to steer the tip region 260. The delivery device 100 can further include a support member 303 and one or more deflection members 396 along the length of the delivery device 100 to aid in deflection in more than one direction and/or more than one position along the longitudinal length. The deflection member(s) 396 can also be rotated or transitioned longitudinally within the inner shaft 120 to achieve the desired deflection/steerability.

V. Procedural Techniques for Delivery of Implants Using Delivery Devices

The following example describes one procedure for treating venous sinus stenosis with the delivery devices 100 and the implants 1000 describe herein. Vascular access is obtained by placing a sheath in the femoral, brachial or jugular vein (JV). A guiding catheter (e.g., the guiding catheter 1700 of FIG. 10) with an introducer, and associated, typically 0.035", guide wire (e.g., the guide wire 1600 of FIG. 10) is inserted into the sheath and advanced up to the jugular bulb. Optionally, the guiding catheter 1700 can be positioned with the distal end inside the sigmoid sinus (e.g., the sigmoid sinus (SS) of FIG. 10), or the guiding catheter 1700 can be advanced further into the anatomy (e.g., to the transverse sinus (TS), the narrowing transverse sinus (TSN), the superior sagittal sinus (SSS) of FIG. 10). Once vascular access is obtained, the guide wire 1600 (e.g., the 0.035" guide wire) and the guiding catheter introducer are removed from the patient.

The annulus located within the delivery device 100 including the implant 1000, positioned between the inner shaft 120 and outer shaft 500, can be flushed with fluid (e.g., saline) via a flush port and flush port tube (e.g., the second lumen port 940 and the port tube 950 of FIG. 4) which can be a Luer fitting. If provided, air can be expelled through a vent in the delivery device (e.g., the vent 325 of FIG. 11 or 25). A lumen of the delivery device 100 (e.g., the lumen 205) can be flushed with fluid (e.g., saline) via a lumen port (e.g., the lumen port 920). The delivery device 100 including the implant 1000 is loaded with a, typically 0.014", guide wire 1600 and inserted into the guiding catheter 1700. The delivery device 100 including the implant 1000 is advanced near the distal end of the guiding catheter 1700. A POS marker (e.g., the POS marker 530 of FIG. 19) can be used to enable advancement without the use of fluoroscopy. The guide wire 1600 is advanced until the distal end is beyond the desired location for deployment of the implant 1000. If the desired location is having the distal end of the implant 1000 adjacent the torcula, the guide wire 1600 can be advanced cither into the superior sagittal sinus (SSS) or contralateral transverse sinus (TS). The delivery device 100 including the implant 1000 is then advanced over the guide wire 1600 until the implant 1000 is in the desired location. Optionally, the delivery device 100 including the implant 1000 and guide wire 1600 can be moved together or independently in smaller increments through the vasculature. If the guiding catheter 1700 is advanced/positioned at where the implant 1000 is to be deployed, the guiding catheter 1700 can be retracted a distance great enough such that the implant 1000 can deploy without interference.

Once the implant 1000 is in the desired location, as determined by the radiopaque marker(s) of the delivery device 100 (e.g., the radiopaque marker(s) 330 of FIGS. 11-16) and/or the radiopaque marker(s) of the implant 1000 (e.g., the radiopaque marker(s) 1300 of FIGS. 5A-9A). A handle (e.g., the handle 800 of FIG. 1) can be used to retract the outer shaft (e.g., the outer shaft 500 of FIG. 1) of the delivery device 100. More specifically, a pin hub (e.g., the pin hub 932 of FIG. 31) can be held in position, as an actuator (e.g., the actuator 826 of FIG. 31) is loosened, and a handle body (e.g., the handle body 822 of FIG. 31) is moved towards the pin hub 932 to initiate retraction of the outer shaft 500 and deployment of the implant 1000 from the delivery device 100. A small length of implant 1000 can be deployed first to enable engagement of the implant 1000 with the vessel wall. Location of the implant 1000 can be evaluated and if and/or when the implant 1000 is in the desired location, further retraction of the handle body 822 is continued to retract the outer shaft 500 until the implant 1000 is fully deployed.

If one or more additional implants 1000 are loaded on the delivery device 100, the guide wire 1600 is moved until the distal end is beyond the desired location for the additional implant 1000 deployment. Deployment of the implant 1000 in this location is conducted as previously described. This can be repeated until the desired area of implant 1000 coverage is achieved and/or all implants 1000 have been deployed.

After deployment of the one or more implants 1000 is completed, the delivery device 100 is retracted into the guiding catheter 1700 and the guide wire 1600 is retracted into the guiding catheter 1700. Optionally, the delivery device 100 and guide wire 1600 can be retracted into the guiding catheter 1700 together or in any order or steps. Diagnostics can be conducted to assess placement, physiologic parameters, relief of symptoms, etc. provided by initial delivery of the implants 1000. If the delivery device 100 includes sensors 370, diagnostics can be taken pre-deployment, during, and/or post-deployment of the implant 1000 prior to removal of the delivery device 100 from the patient. The guiding catheter 1700 is then removed from the patient and the access site is closed using known methodology.

It is worth noting that the delivery device 100 with the implant 1000 and/or any one of the individual components or any subset of the components described herein can be used as a complete system, individually, in combinations, and/or with other guidewires, catheters, or vascular and non-vascular devices. Various sizes and combinations can be selected and used depending upon the intended clinical procedure.

VI. Conclusion

It will be apparent to those having skill in the art that changes can be made to the details of the above-described embodiments without departing from the underlying principles of the present technology. In some cases, well known structures and functions have not been shown or described in detail to avoid unnecessarily obscuring the description of the embodiments of the present technology. Although steps of methods can be presented herein in a particular order, alternative embodiments can perform the steps in a different order. Similarly, certain aspects of the present technology disclosed in the context of particular embodiments can be combined or eliminated in other embodiments. Furthermore, while advantages associated with certain embodiments of the present technology can have been disclosed in the context of those embodiments, other embodiments can also exhibit such advantages, and not all embodiments need necessarily exhibit such advantages or other advantages disclosed herein to fall within the scope of the technology. Accordingly, the disclosure and associated technology can encompass other embodiments not expressly shown or described herein, and the invention is not limited except as by the appended claims.

Where context permits, singular or plural terms can also include the plural or singular term, respectively. In addition, unless the word "or" is expressly limited to mean only a single item exclusive from the other items in reference to a list of two or more items, then the use of "or" in such a list is to be interpreted as including (a) any single item in the list, (b) all of the items in the list, or (c) any combination of the items in the list. Furthermore, as used herein, the phrase "and/or" as in "A and/or B" refers to A alone, B alone, and both A and B. Additionally, the terms "comprising," "including," "having," and "with" are used throughout to mean including at least the recited feature(s) such that any greater number of the same features and/or additional types of other features are not precluded. Moreover, as used herein, the phrases "based on," "depends on," "as a result of," and "in response to" shall not be construed as a reference to a closed set of conditions. For example, an exemplary step that is described as "based on condition A" can be based on both condition A and condition B without departing from the scope of the present disclosure. In other words, as used herein, the phrase "based on" shall be construed in the same manner as the phrase "based at least in part on" or the phrase "based at least partially on."

Throughout this disclosure, the singular terms "a," "an," and "the" include plural referents unless the context clearly indicates otherwise. Additionally, the term "comprising," "including," and "having" should be interpreted to mean including at least the recited feature(s) such that any greater number of the same feature and/or additional types of other features are not precluded.

Reference herein to "one embodiment," "an embodiment," "some embodiments" or similar formulations means that a particular feature, structure, operation, or characteristic described in connection with the embodiment can be included in at least one embodiment of the present technology. Thus, the appearances of such phrases or formulations herein are not necessarily all referring to the same embodiment. Furthermore, various particular features, structures, operations, or characteristics can be combined in any suitable manner in one or more embodiments.

Unless otherwise indicated, all numbers expressing concentrations, shear strength, and other numerical values used in the specification and claims, are to be understood as being modified in all instances by the term "about." Accordingly, unless indicated to the contrary, the numerical parameters set forth in the following specification and attached claims are approximations that can vary depending upon the desired properties sought to be obtained by the present technology. At the very least, and not as an attempt to limit the application of the doctrine of equivalents to the scope of the claims, each numerical parameter should at least be construed in light of the number of reported significant digits and by applying ordinary rounding techniques. Additionally, all ranges disclosed herein are to be understood to encompass any and all subranges subsumed therein. For example, a range of "1 to 10" includes any and all subranges between (and including) the minimum value of 1 and the maximum value of 10, i.e., any and all subranges having a minimum value of equal to or greater than 1 and a maximum value of equal to or less than 10, e.g., 5.5 to 10.

The disclosure set forth above is not to be interpreted as reflecting an intention that any claim requires more features than those expressly recited in that claim. Rather, as the following claims reflect, inventive aspects lie in a combination of fewer than all features of any single foregoing disclosed embodiment. Thus, the claims following this Detailed Description are hereby expressly incorporated into this Detailed Description, with each claim standing on its own as a separate embodiment. This disclosure includes all permutations of the independent claims with their dependent claims.

The present technology is illustrated, for example, according to various aspects described below as numbered clauses (1, 2, 3, etc.) for convenience. These are provided as examples and do not limit the present technology. It is noted that any of the dependent clauses can be combined in any combination, and placed into a respective independent clause. The other clauses can be presented in a similar manner.

The present technology is illustrated, for example, according to various aspects described below as numbered clauses (1, 2, 3, etc.) for convenience. These are provided as examples and do not limit the present technology. It is noted that any of the dependent clauses may be combined in any combination, and placed into a respective independent clause. The other clauses can be presented in a similar manner.

1. A delivery device configured to deliver an implant to a target vessel of a patient, the delivery device comprising:

an inner shaft defining a lumen extending along a length of the delivery device, wherein the inner shaft comprises an implant region including a recess, and wherein the recess is configured to receive a self-expandable implant configured to expand from a constrained state to an unconstrained state;

an outer shaft surrounding the inner shaft along at least a first portion of the length of the delivery device, wherein the outer shaft is retractable in a proximal direction relative to the inner shaft;

a tip portion distal to the outer shaft and/or the recess, wherein the tip portion extends to a distal terminus of the delivery device and includes a cross-sectional dimension that tapers in a distal direction;

a functional member extending along at least a second portion of the length of the delivery device, wherein the functional member is within the outer shaft and/or radially between the recess and the outer shaft, and wherein the functional member is configured to provide an increased tensile strength to the outer shaft;

a coil extending along at least a third portion of the length of the delivery device, wherein the coil is within the outer shaft and/or radially between the functional member and the outer shaft.

2. The delivery device of any one of the clauses herein, wherein the functional member comprises a braid.

3. The delivery device of any one of the clauses herein, wherein the functional member forms a perimeter around the recess.

4. The delivery device of any one of the clauses herein, wherein the functional member comprises a fiber including a total tensile strength of at least 1.5 pounds.

5. The delivery device of any one of the clauses herein, wherein the functional member comprises a fiber, and wherein the fiber is a string and/or does not entirely surround the outer shaft.

6. The delivery device of any one of the clauses herein, wherein the functional member comprises a fiber, and wherein the fiber is a string and/or does not entirely surround the recess.

7. The delivery device of any one of the clauses herein, wherein the functional member comprises an aramid and/or liquid crystal polymer fiber.

8. The delivery device of any one of the clauses herein, wherein the functional member comprises a fiber that does not entirely surround the outer shaft, the delivery device further comprising a braid within the outer shaft.

9. The delivery device of any one of the clauses herein, wherein the functional member comprises a fiber that does not entirely surround the recess, the delivery device further comprising a braid that forms a perimeter around the recess.

10. The delivery device of any one of the clauses herein, further comprising a hypotube proximal to the implant region and radially inward of the outer shaft, wherein the hypotube comprises stainless steel and/or nitinol.

11. The delivery device of any one of the clauses herein, further comprising a hypotube proximal to the implant region and radially inward of the functional member, wherein the hypotube includes a varying number of slots or fenestrations along the length of the delivery device such that a flexibility of the hypotube increases in the distal direction.

12. The delivery device of any one of the clauses herein, wherein the tip portion has a tip length of at least 1.5 centimeters.

13. The delivery device of any one of the clauses herein, wherein the tip portion has a tip length of at least 1.5 centimeters, a proximal region having a cross-sectional dimension of 1.-2.5 millimeters, and a distal region having a cross-sectional dimension of 0.5-1.5 millimeters.

14. The delivery device of any one of the clauses herein, wherein the tip portion has a tip length of at least 1.5 centimeters, and a majority of the tip region has a cross-sectional dimension less than 2.5 millimeters.

15. The delivery device of any one of the clauses herein, wherein the inner shaft is formed of a first material and the tip portion is formed of a second materials different than the first material.

16. The delivery device of any one of the clauses herein, wherein the inner shaft and the tip portion are formed of a single material and comprise a continuous surface.

17. The delivery device of any one of the clauses herein, wherein the cross-sectional dimension of the tip portion tapers along a majority of a length of the tip portion.

18. The delivery device of any one of the clauses herein, wherein the recess is defined in part by (i) a base recess surface extending along part of the length of the delivery device, (ii) a proximal recess surface angled relative to the base recess surface, and (iii) a distal recess surface angled relative to the base recess surface.

19. The delivery device of any one of the clauses herein, wherein the recess has a length of at least 3 cm, 4 cm, 5 cm, 6 cm, 7 cm, 8 cm, 9 cm, or 10 cm.

20. The delivery device of any one of the clauses herein, wherein the inner shaft or tip portion includes a ledge distal to and extending from the recess, and wherein, when the implant is in the constrained state, a distal end of the outer shaft is over the ledge.

21. The delivery device of any one of the clauses herein, wherein the inner shaft or tip portion includes a ledge distal to and extending from the recess, and wherein, when the implant is in the constrained state, a distal end of the outer shaft overlaps the ledge by at least 2 millimeters or 3 millimeters.

22. The delivery device of any one of the clauses herein, wherein:

the inner shaft or tip portion includes a ledge distal to and extending from the recess, when the implant is in the constrained state, a distal end of the outer shaft is over the ledge, and an outermost region of the outer shaft is longitudinally aligned with and/or adjacent an outermost region of the tip portion.

23 The delivery device of any one of the clauses herein, wherein the inner shaft comprises a proximal inner shaft region proximal to the implant region, and a distal inner shaft region distal to the implant region, wherein a cross-sectional dimension of the implant region is smaller than a cross-sectional dimension of the proximal inner shaft region and the distal inner shaft region.

24. The delivery device of any one of the clauses herein, wherein the delivery device includes an annulus region between the inner shaft and the outer shaft, and wherein the delivery device further comprises a vent extending from the annulus and between the recess and the tip portion.

25 The delivery device of any one of the clauses herein, further comprising a vent extending from the annulus outward through at least a portion of the inner shaft and/or outer shaft, wherein the vent is within and/or distal to the recess of the inner shaft.

26. A delivery device configured to deliver an implant to a target vessel of a patient, the delivery device comprising:

an inner shaft defining a lumen extending along a length of the delivery device, wherein the inner shaft comprises an implant region including a recess configured to receive a self-expandable implant, wherein the recess is defined in part by (i) a base recess surface extending along part of the length of the delivery device, (ii) a proximal recess surface angled relative to the base recess surface, and (iii) a distal recess surface angled at least 90° relative to the base recess surface;

an outer shaft surrounding the inner shaft along at least a first portion of the length of the delivery device, wherein the outer shaft is retractable relative to the inner shaft;

a tip portion distal to the outer shaft and/or the recess, wherein the tip portion a proximal region having a first cross-sectional tip dimension and a distal region having a second cross-sectional tip dimension less than the first cross-sectional tip dimension;

a functional member within the outer shaft and/or outward of the recess, wherein the functional member is configured to provide an increased tensile strength to the outer shaft; and a coil within the outer shaft and/or radially outward of the recess.

27. The delivery device of any one of the clauses herein, wherein the coil includes a first coil portion having a first stiffness, and a second coil portion distal to the first coil portion that has a second stiffness less than the first stiffness.

28. The delivery device of any one of the clauses herein, wherein the coil includes a first coil portion having a first flexibility, and a second coil portion distal to the first coil portion that has a second flexibility more than the first flexibility.

29. The delivery device of any one of the clauses herein, wherein the functional member comprises a braid within the outer shaft, the delivery device further comprising one or more fibers with a total tensile strength of at least 1.5 lbs.

30 The delivery device of any one of the clauses herein, wherein the functional member comprises a braid that forms a perimeter around the recess, the delivery device further comprising a fiber including a total tensile strength of at least 1.5 pounds.

31. The delivery device of any one of the clauses herein, wherein the functional member comprises an aramid and/or liquid crystal polymer fiber.

32 The delivery device of any one of the clauses herein, wherein the recess is at least 3 centimeters or 6 centimeters long and the functional member comprises a fiber that does not entirely surround the outer shaft and/or the recess, the delivery device further comprising:

a braid inward of the coil and/or that forms a perimeter around the recess;

a jacket over the coil; and a hypotube proximal to the implant region and inward of the functional member and/or outer shaft, wherein the hypotube comprises stainless steel and/or nitinol.

33. A method for deploying an implant to a target region of a patient, the method comprising:

inserting a delivery device into the patient, wherein the delivery device comprises— a self-expandable implant configured to expand from a constrained state to an unconstrained state;

an inner shaft defining a lumen extending along a length of the delivery device and including a recess;

an outer shaft surrounding the inner shaft along at least a first portion of the length of the delivery device, wherein the implant is at the recess inward of the outer shaft;

a tapered tip portion distal to the outer shaft and the recess;

a coil within the outer shaft; and a functional member radially inward of the coil;

advancing the delivery device to the target region of the patient;

deploying the implant by retracting the outer shaft relative to the inner shaft, thereby enabling the implant to self-expand; and after deploying the implant, withdrawing the delivery device from the patient.

34. The method of any one of the clauses herein, wherein the target region comprises a venous sinus, transverse sinus, sigmoid sinus, superior sagittal sinus, or jugular vein.

35. The method of any one of the clauses herein, wherein the coil includes a first coil portion having a first stiffness, and a second coil portion distal to the first coil portion that has a second stiffness less than the first stiffness.

36. The method of any one of the clauses herein, wherein the coil includes a first coil portion having a first flexibility, and a second coil portion distal to the first coil portion that has a second flexibility more than the first flexibility.

37. The method of any one of the clauses herein, wherein the functional member comprises a braid that forms a perimeter around the recess and/or is within the outer shaft, the delivery device further comprising a fiber including a total tensile strength of at least 1.5 lbs.

38. The method of any one of the clauses herein, wherein the recess is at least 3 centimeters or 6 centimeters long and the functional member comprises a Vectran fiber that does not entirely surround the recess and/or the outer shaft, the delivery device further comprising:

a braid inward of the coil and/or that forms a perimeter around the recess;

a jacket over the coil; and a hypotube proximal to the implant region and inward of the functional member and/or outer shaft, wherein the hypotube comprises stainless steel and/or nitinol.

39. A delivery device configured to deliver an implant to a target vessel of a patient, the delivery device comprising:

an inner shaft defining a lumen extending along a length of the delivery device, wherein the inner shaft includes a distal inner shaft tip portion having a cross-sectional dimension that tapers in a distal direction;

an outer shaft surrounding the inner shaft along at least a portion of the length, wherein the outer shaft is retractable relative to the inner shaft; and a self-expandable implant radially between the lumen and the outer shaft and proximal to the distal inner shaft tip portion, wherein, in operation when the outer shaft retracts relative to the inner shaft, the implant expands from a constrained state to an unconstrained state.

40. The delivery device of any one of the clauses herein, wherein the implant in the constrained state has a first shape and in the unconstrained state has a second shape different than the first shape.

41. The delivery device of any one of the clauses herein, wherein the implant in the constrained state has a circular or rounded square shape and in the unconstrained state has a non-circular or rounded triangular shape.

42. The delivery device of any one of the clauses herein, wherein the implant comprises a first zone and a second zone distal to the first zone, wherein the first zone includes a first shape and the second zone includes a second shape different than the first shape when expanded in free air or without an externally confining surface.

43. The delivery device of any one of the clauses herein, wherein the implant comprises a first zone and a second zone distal to the first zone, wherein the first zone includes a first radial force and the second zone includes a second radial force different than the first radial force.

44. The delivery device of any one of the clauses herein, wherein the implant comprises a first zone and a second zone distal to the first zone, wherein the first zone includes a first radial force and the second zone includes a second radial force different than the first radial force.

45. The delivery device of any one of the clauses herein, wherein the implant further comprises a plurality of structures and a plurality of connectors each extending between adjacent individual ones of the structures, wherein individual ones of the structures comprise or consist of a continuous filament having multiple turns and forming a predetermined shape.

46. The delivery device of any one of the clauses herein, wherein the implant further comprises a plurality of structures each spaced apart from adjacent structures and connected to adjacent structures via one or more connectors.

47. The delivery device of any one of the clauses herein, wherein the implant further comprises a first zone including a plurality of first structures and a second zone, distal to the first zone, including a plurality of second structures, wherein the first structures are spaced apart from adjacent structures and connected to adjacent structures via one or more connectors, and wherein the second structures are directly coupled to adjacent second structures.

48. The delivery device of any one of the clauses herein, wherein the implant further comprises a plurality of structures connected to one another via one or more connectors, wherein individual ones of the structures have a length of at least 0.5 millimeters (mm), 1 mm, 2 mm, 3 mm, 4 mm, 5 mm, 6 mm, 7 mm, 8 mm, 9 mm, or 10 mm, or within a range of 0.5-10 mm.

49. The delivery device of any one of the clauses herein, wherein the implant further comprises a first structure including a first number of turns and forming a first shape, and a second structure distal to the first structure, wherein the second structure includes a second number of turns different than the first number of turns and/or a second shape different than the first shape.

50. The delivery device of any one of the clauses herein, wherein the implant further comprises a first zone including a plurality of first structures each connected to adjacent first structures via a first number of connectors, and a second zone distal to the first zone, wherein the second zone includes a plurality of second structures each connected to adjacent second structures via a second number of connectors greater than the first number of connectors.

51. The delivery device of any one of the clauses herein, wherein the implant further comprises a first zone including a plurality of first structures each having a first flexibility and a first radially outward force, and a second zone distal to the first zone, wherein the second zone includes a plurality of second structures each having a second flexibility different than the first flexibility and/or a second radially outward force different than the first radially outward force.

52. The delivery device of any one of the clauses herein, wherein the implant further comprises a first zone including a plurality of first structures each defining a ring, wherein the first structures include a primary structure having a first width and a secondary structure, distal to the primary structure, having a second width different than the first width.

53. The delivery device of any one of the clauses herein, wherein the implant further comprises a first zone including a first structure, and a second zone distal to the first zone and including a second structure, wherein the first structure comprises a first number of turns and the second structure comprises a second number of turns different than the first number of turns, and wherein the first structure is directly coupled to the second structure via one or more connectors.

54. The delivery device of any one of the clauses herein, wherein the implant further comprises a first zone including a plurality of first structures, and a second zone distal to the first zone and including a plurality of second structures, wherein individual ones of the first structures comprise a first diameter and individual ones of the second structures comprise a second diameter less than the first diameter.

55. The delivery device of any one of the clauses herein, wherein the implant comprises a braid, and wherein a pitch of the braid varies or decreases along a length of the implant in a distal direction.

56. The delivery device of any one of the clauses herein, where the implant comprises a first zone including structures having filaments and a second zone, distal to the first zone, including a braid.

57. The delivery device of any one of the clauses herein, where the implant comprises a first zone including structures having filaments and a second zone, distal to the first zone, including a braid, and wherein the first zone in the unconstrained state has a first shape and the second zone in the unconstrained state has a second shape different than the first shape.

58. The delivery device of any one of the clauses herein, wherein the implant comprises nitinol (NiTi), nitinol alloy, stainless steel, and/or combinations thereof.

59. The delivery device of any one of the clauses herein, wherein the implant has a length of at least 2 centimeters (cm), 5 cm, 6 cm, 8 cm, 10 cm, 15 cm, 30 cm, or 15 cm, or within a range of 2-15 cm.

60 The delivery device of any one of the clauses herein, wherein the implant in the collapsed state and/or the unconstrained state exerts a radially-outward force of at least 0.001 Newtons (N)/millimeters (mm), 0.005 N/mm, 0.01 N/mm, 0.02 N/mm, 0.05 N/mm, 0.1 N/mm, 0.5 N/mm, 1 N/mm, 2 N/mm, 3 N/mm, or 4 N/mm, or within a range of 0.001-40 N/mm.

61 The delivery device of any one of the clauses herein, wherein the implant has a radially outward force that decreases along a length of the implant in a distal direction.

62. The delivery device of any one of the clauses herein, wherein the inner shaft and the distal inner shaft tip region comprise and/or are made from a single material.

63. The delivery device of any one of the clauses herein, wherein the inner shaft comprises a proximal inner shaft region having a first flexibility and a distal inner shaft region having a second flexibility greater than the first flexibility.

64. The delivery device of any one of the clauses herein, wherein the inner shaft comprises a proximal inner shaft region proximal to the implant, an implant inner shaft region distal to the proximal inner shaft region, and a distal inner shaft region distal to the implant inner shaft region, wherein a cross-sectional dimension or diameter of the implant inner shaft region is smaller than a cross-sectional dimension or diameter of the proximal inner shaft region and/or the distal inner shaft region.

65. The delivery device of any one of the clauses herein, wherein the target vessel comprises a venous sinus, the transverse sinus, the sigmoid sinus, the superior sagittal sinus, or the jugular vein.

I claim:

1. A delivery device configured to deliver an implant to a target vessel of a patient, the delivery device comprising:

an inner shaft defining a lumen extending along a length of the delivery device, wherein the inner shaft comprises (i) an implant region including a surface defining a recess configured to receive a self-expandable implant, and (ii) a first functional member inward of the recess and extending through the implant region, wherein the recess is spaced apart from the first functional member by the surface;

an outer shaft surrounding the inner shaft along at least a first portion of the length of the delivery device, wherein the outer shaft comprises (i) a second functional member outward of the recess and extending along at least a second portion of the length of the delivery device, and (ii) a coil extending along at least a third portion of the length of the delivery device, and wherein the outer shaft is retractable in a proximal direction relative to the inner shaft;

a tip portion distal to the outer shaft and/or the recess, wherein the tip portion extends to a distal terminus of the delivery device and includes a cross-sectional dimension that tapers in a distal direction, and wherein the tip portion defines a distal surface of the recess; and a third functional member extending proximal to the implant region such that the third functional member defines a proximal surface of the recess, wherein the third functional member includes a varying amount of slots or fenestrations along at least a fourth portion of the length of the delivery device such that a flexibility of the third functional member increases in the distal direction.

2. The delivery device of claim 1, wherein the self-expandable implant is configured to expand from a constrained state to an unconstrained state.

3. The delivery device of claim 1, wherein the first functional member provides increased longitudinal stiffness to the inner shaft along at least a portion of the implant region.

4. The delivery device of claim 1, wherein the first functional member extends through the implant region and at least a portion of the tip portion.

5. The delivery device of claim 1, wherein the first functional member extends through the implant region and at least a portion of the tip portion such that a distal end of the first functional member is within the tip portion.

6. The delivery device of claim 1, wherein the first functional member comprises stainless steel and/or nitinol.

7. The delivery device of claim 1, wherein the first functional member comprises a braid that forms a perimeter inward of the recess.

8. The delivery device of claim 1, wherein the second functional member provides increased tensile strength to the outer shaft.

9. The delivery device of claim 1, wherein the coil is outward and/or over the second functional member.

10. The delivery device of claim 1, wherein the second functional member comprises a braid that forms a perimeter outward of the recess.

11. The delivery device of claim 1, wherein the second functional member comprises a fiber, and wherein the fiber is a string and/or does not entirely surround the recess.

12. The delivery device of claim 1, wherein the second functional member comprises an aramid and/or liquid crystal polymer fiber.

13. The delivery device of claim 1, wherein the second functional member is a braid comprising stainless steel, and wherein the coil comprises nitinol and is positioned over the second functional member.

14. The delivery device of claim 1, wherein the outer shaft includes the second functional member and the coil, such that the second functional member and the coil are retractable relative to the inner shaft.

15. The delivery device of claim 1, wherein the outer shaft is configured to withstand a radial outward force between 0.1 N/mm and 10 N/mm.

16. The delivery device of claim 1, wherein:

the inner shaft or the tip portion includes a ledge distal to and extending from the recess, when the implant is in a constrained state, a distal end of the outer shaft is over the ledge, and an outermost region of the outer shaft is longitudinally aligned with an outermost region of the tip portion.

17. The delivery device of claim 1, further comprising a vent extending outward from an annulus between the inner shaft and the outer shaft, through at least a portion of the inner shaft and/or the outer shaft, wherein the vent is within and/or distal to the recess of the inner shaft.

18. The delivery device of claim 1, wherein the tip portion has a tip length of at least 1.5 centimeters, a proximal region having a cross-sectional dimension of 1.0-2.5 millimeters, and a distal region having a cross-sectional dimension of 0.5-1.5 millimeters.

19. The delivery device of claim 1, wherein the inner shaft or the tip portion includes a ledge distal to and extending from the recess, and wherein, when the implant is in a constrained state, a distal end of the outer shaft overlaps the ledge by at least 1 millimeter.

20. The delivery device of claim 1, wherein the delivery device includes a minimum bend radius of at least 7 millimeters.

21. A delivery device configured to deliver an implant to a target vessel of a patient, the delivery device comprising:

an inner shaft defining a lumen extending along a length of the delivery device, wherein the inner shaft comprises (i) an implant region including a recess configured to receive a self-expandable implant, and (ii) a first functional member inward of the recess and extending through the implant region;

an outer shaft surrounding the inner shaft along at least a first portion of the length of the delivery device, wherein the outer shaft comprises (i) a second functional member outward of the recess and extending along at least a second portion of the length of the delivery device, and (ii) a coil extending along at least a third portion of the length of the delivery device, and wherein the outer shaft is retractable in a proximal direction relative to the inner shaft;

a tip portion distal to the outer shaft and/or the implant region, wherein the tip portion extends to a distal terminus of the delivery device and includes a cross-sectional dimension that tapers in a distal direction; and a third functional member proximal to the implant region and including a varying amount of slots or fenestrations along at least a fourth portion of the length of the delivery device such that a flexibility of the third functional member increases in the distal direction, wherein at least a portion of the tip portion and the third functional member define the recess.

22. A delivery device configured to deliver an implant to a target vessel of a patient, the delivery device comprising:

an inner shaft defining a lumen extending along a length of the delivery device, wherein the inner shaft comprises (i) an implant region including a recess configured to receive a self-expandable implant, and (ii) a first functional member inward of the recess and extending through the implant region;

an outer shaft surrounding the inner shaft along at least a first portion of the length of the delivery device, wherein the outer shaft comprises (i) a second functional member outward of the recess and extending along at least a second portion of the length of the delivery device, and (ii) a coil extending along at least a third portion of the length of the delivery device, wherein the outer shaft is retractable in a proximal direction relative to the inner shaft, and wherein the second functional member comprises a fiber that does not entirely surround the recess, and a braid that forms a perimeter outward of the recess; and a tip portion distal to the outer shaft and/or the recess, wherein the tip portion extends to a distal terminus of the delivery device and includes a cross-sectional dimension that tapers in a distal direction.

23. A delivery device configured to deliver an implant to a target vessel of a patient, the delivery device comprising:

an inner shaft defining a lumen extending along a length of the delivery device, wherein the inner shaft comprises (i) an implant region including a recess configured to receive a self-expandable implant, and (ii) a first functional member inward of the recess and extending through the implant region, wherein the first functional member comprises stainless steel and/or nitinol;

an outer shaft surrounding the inner shaft along at least a first portion of the length of the delivery device, wherein the outer shaft comprises (i) a second functional member outward of the recess and extending along at least a second portion of the length of the delivery device, (ii) a coil extending along at least a third portion of the length of the delivery device, (iii) a braid inward of the coil, and (iv) a jacket over the coil, wherein the outer shaft is retractable in a proximal direction relative to the inner shaft, and wherein the second functional member comprises a fiber that does not entirely surround the recess; and a tip portion distal to the outer shaft and/or the recess, wherein the tip portion extends to a distal terminus of the delivery device and includes a cross-sectional dimension that tapers in a distal direction.

* * * * *